(12) United States Patent
Hill et al.

(10) Patent No.: US 12,344,598 B2
(45) Date of Patent: Jul. 1, 2025

(54) BIS(DIAZIRINE) DERIVATIVES AS PHOTO-CROSSLINKER FOR TREATING CORNEAL ECTATIC DISORDERS

(71) Applicant: Avedro, Inc., Waltham, MA (US)

(72) Inventors: Jason Hill, Auburndale, MA (US); Desmond Adler, Bedford, MA (US)

(73) Assignee: Avedro, Inc., Waltham, MA (US)

( * ) Notice: Subject to any disclaimer, the term of this patent is extended or adjusted under 35 U.S.C. 154(b) by 908 days.

(21) Appl. No.: 17/424,413

(22) PCT Filed: Jan. 24, 2020

(86) PCT No.: PCT/US2020/015071
§ 371 (c)(1),
(2) Date: Jul. 20, 2021

(87) PCT Pub. No.: WO2020/154673
PCT Pub. Date: Jul. 30, 2020

(65) Prior Publication Data
US 2022/0106298 A1 Apr. 7, 2022

Related U.S. Application Data

(60) Provisional application No. 62/796,803, filed on Jan. 25, 2019.

(51) Int. Cl.
*A61P 27/10* (2006.01)
*C07D 229/02* (2006.01)
(Continued)

(52) U.S. Cl.
CPC ............ *C07D 403/12* (2013.01); *A61P 27/10* (2018.01); *C07D 229/02* (2013.01); *C07D 401/14* (2013.01); *C07D 403/14* (2013.01)

(58) Field of Classification Search
CPC .. C07D 403/12; C07D 401/14; C07D 403/14; A61P 27/10; A61P 27/00; A61P 27/02;
(Continued)

(56) References Cited

U.S. PATENT DOCUMENTS 3,514,447 A * 5/1970 Church ................ C07D 403/14
544/359
7,073,510 B2 7/2006 Redmond et al.
(Continued)

FOREIGN PATENT DOCUMENTS

| CN | 103384514 A | 11/2013 |
| CN | 106715399 A | 5/2017 |

(Continued)

OTHER PUBLICATIONS

Li et al. "Multivalent Photoaffinity Probe for Labeling Small Molecule Binding Proteins" Bioconj. Chem. 2014, 25, 1172-1180 (Year: 2014).*
(Continued)

*Primary Examiner* — Amanda L. Aguirre
(74) *Attorney, Agent, or Firm* — Knobbe Martens Olson & Bear LLP

(57) ABSTRACT

This disclosure features bis(diazirine) derivatives of the formulae (I) (1-a) or (1-b) that generate cross-linking in the cornea in response to exposure to an electromagnetic irradiation (e.g. UV-light). The compounds are useful, e.g. for treating a subject (e.g. a human) having a disease, disorder or condition in which abnormal shaping of the cornea (e.g. thinning of the cornea, e.g. bilateral thinning of the cornea, e.g. bilateral thinning of the central, paracentral, or peripheral cornea, or steepening (e.g., bulging) of the cornea) contributes to the pathology and/or symptoms, and/or progression of the disease, disorder or condition. Examples of such diseases, disorders or conditions include: (i) corneal ectatic disorders; (ii) vision conditions; and (iii) diseases, disorders, or conditions that are sequela or comorbid with any of the foregoing or any disclosed herein. More particular examples of such diseases, disorders or conditions include keratoconus, keratoglobus, pellucid marginal degeneration, corneal ectasia (e.g. postoperative ectasia, e.g. post-LASIK ectasia), Terrien's marginal degeneration, myopia, hyperopia, astigmatism, irregular astigmatism and presbyopia. In some embodiments, the claimed methods can be performed in the absence of added or supplemental oxygen levels, which can be advantageous in some applications. Preferred exemplary compounds are e.g. bis(diazirine) amino acid derivatives, such as e.g. example 1:

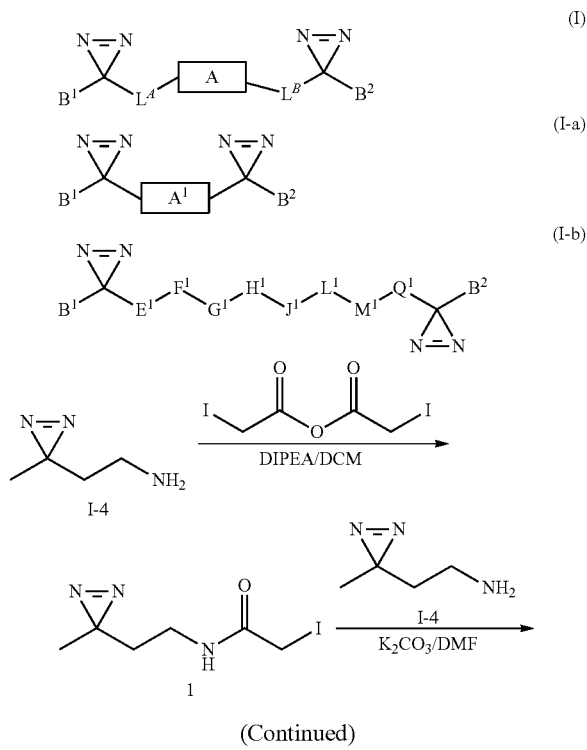

(Continued)

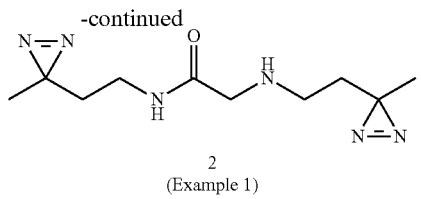

2
(Example 1)

17 Claims, No Drawings

(51) Int. Cl.
 *C07D 401/14* (2006.01)
 *C07D 403/12* (2006.01)
 *C07D 403/14* (2006.01)
(58) Field of Classification Search
 CPC .............. A61K 31/396; A61K 31/4178; A61K
       31/4523; A61K 31/5377; A61K 45/06
 See application file for complete search history.

(56) References Cited

U.S. PATENT DOCUMENTS

| 8,574,277 | B2 | 11/2013 | Muller et al. |
| 2011/0130356 | A1 | 6/2011 | Stefano et al. |
| 2011/0237999 | A1 | 9/2011 | Muller et al. |
| 2012/0215155 | A1 | 8/2012 | Muller et al. |
| 2013/0060187 | A1 | 3/2013 | Friedman et al. |
| 2013/0245536 | A1 | 9/2013 | Friedman et al. |
| 2014/0343480 | A1 | 11/2014 | Kamaev et al. |
| 2015/0017192 | A1* | 1/2015 | Usera .................. C07D 229/02 435/68.1 |
| 2015/0130944 | A1 | 5/2015 | Hsu |
| 2016/0083352 | A1 | 3/2016 | Burgoon et al. |
| 2016/0090016 | A1 | 3/2016 | Williams |
| 2018/0236077 | A1 | 8/2018 | Friedman et al. |

FOREIGN PATENT DOCUMENTS

| CN | 107206003 A | 9/2017 |
| WO | WO 2011/130356 | 10/2011 |
| WO | WO 2012/095877 A | 7/2012 |
| WO | WO 2015/130944 | 9/2015 |
| WO | WO 2016/049123 A1 | 3/2016 |
| WO | WO 2016/090016 | 6/2016 |
| WO | WO 2016/090016 A1 | 6/2016 |
| WO | WO 2017/155580 | 9/2017 |
| WO | WO 2020/012332 | 1/2020 |

OTHER PUBLICATIONS

Shaffer et al. "Efficient Covalent Bond Formation in Gas-Phase Peptide-Peptide Ion Complexes with the Photoleucine Stapler" J. Am. Soc. Mass Spectrom. 2016, 27, 633-645 (Year: 2016).*

Gao et al., "Submicro/nano porous epoxy resin fabricated via UV initiated foaming" Materials Letters (2019) 251:69-72.
Office Action dated Dec. 16, 2023 for CN Application No. 202080024560.4, filed Jan. 24, 2020.
Office Action dated Oct. 3, 2023 for MX Application No. MX/a/2021/008821, filed Jan. 24, 2020.
Office Action drafted Jan. 23, 2024 for JP Application No. 2021-543272, filed Jan. 24, 2020.
Office Action dated Feb. 22, 2024 for MX Application No. MX/a/2021/008821, filed Jan. 24, 2020.
Church et al., "Diazirines. 3. Synthesis of a series of diazirine-containing molecules and their pharmacological evaluation", J. Med. Chem. (1972)j 15(5):514-518.
Feng et al., "Submicro/nano porous epoxy resin fabricated via UV initiated foaming" Materials Letters (2019) 251:69-72.
Kandala et al., "Targeting Translation Activity at the Ribosome Interface with UV-Active Small Molecules" ACS Omega (2019) 4(6):10336-10345.
Li et al., "Multivalent Photoaffinity Probe for Labeling Small Molecule Binding Proteins", Bioconjugate Chem. (2014) 25(6):1172-1180.
Shaffer et al., "Efficient Covalent Bond Formation in Gas-Phase Peptide-Peptide Ion Complexes with the Photoleucine Stapler", J. Am. Soc. Mass Spectrom. (2016) 27(4):633-645.
International Search Report and Written Opinion mailed Apr. 21, 2020 for PCT Application No. PCT/US2020/015071, filed Jan. 24, 2020.
International Preliminary Report on Patentability issued Jul. 27, 2021 for PCT Application No. PCT/US2020/015071, filed Jan. 24, 2020.
Office Action drafted Jul. 11, 2024 for JP Application No. 2021-543272, filed Jan. 24, 2020.
Church et al., "Diazirines. 3. Synthesis of a series of diazirine-containing molecules and their pharmacological evaluation",J. of Med. Chem., 1972, 15:5 514-518.
Gao et al., "Submicro/nano porous epoxy resin fabricated via UV initiated foaming", Materials Letters, May 2019, 251:69-72.
International Preliminary Report on Patentability in International Appln. No. PCT/2020015071, dated Jul. 27, 2021, 10 pages.
International Search Report and Written Opinion in Appl. No. PCT/US2020/015071, dated Apr. 21, 2021, 20 pages.
Kalamajski et al., "The decorin sequence SYIRIADTNIT binds collagen type I," J. Biol. Chem., 2007, 282:16062.
Kandala et al., "Targeting Translation Activity at the Ribosome Interface with UV-Active Small Molecules", ACS Omega, Jun. 2019, 4:10336-10345.
Li et al., "Multivalent Photoaffinity Probe for Labeling Small Molecule Binding Proteins", Bioconjugate Chem., Jun. 2014, 25:6:1172-1180.
Shaffer et al., "Efficient Covalent Bond Formation in Gas-Phase Peptide-Peptide Ion Complexes with the Photoleucine Stapler," Am. Mass. Spectrom., Jan. 2016, 27:4:633-645.
Wollensak et al., "Riboflavin/ultraviolet-a-induced collagen crosslinking for the treatment of keratoconus," Am J Ophthalmol. 2003, 135:620-627.
First Examination Report dated Oct. 23, 2024 for AU Patent Application No. 2020212055, filed Jan. 24, 2020.
Office Action dated Jan. 16, 2025 for CA Application No. 3,127,824, filed Jan. 24, 2020.

* cited by examiner

BIS(DIAZIRINE) DERIVATIVES AS PHOTO-CROSSLINKER FOR TREATING CORNEAL ECTATIC DISORDERS

CROSS REFERENCE TO RELATED APPLICATIONS

This application claims the benefit of U.S. Provisional Application Ser. No. 62/796,803, filed on Jan. 25, 2019, which is incorporated herein by reference in its entirety.

TECHNICAL FIELD

This disclosure features chemical entities (e.g., a compound or a pharmaceutically acceptable salt and/or hydrate and/or prodrug of the compound) that that generates cross-linking in the cornea in response to exposure to an electromagnetic irradiation. This disclosure also features compositions containing the same as well as other methods of using and making the same. The chemical entities are useful, e.g., for treating a subject (e.g., a human) having a disease, disorder, or condition in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. Non-limiting examples of such diseases, disorders, or conditions include: (i) corneal ectatic disorders; (ii) vision conditions; and (iii) diseases, disorders, or conditions that are sequela or comorbid with any of the foregoing or any disclosed herein. More particular non-limiting examples of such diseases, disorders, or conditions include keratoconus, keratoglobus, pellucid marginal degeneration, corneal ectasia (e.g., post-operative ectasia, e.g., post-LASIK ectasia), Terrien's marginal degeneration, myopia, hyperopia, astigmatism, irregular astigmatism, and presbyopia.

BACKGROUND

A variety of eye disorders, such as myopia, keratoconus, and hyperopia, involve abnormal shaping of the cornea. Laser-assisted in-situ keratomileusis (LASIK), for example, is one of a number of corrective treatments that reshape the cornea so that light traveling through the cornea is properly focused onto the retina located in the back of the eye. The success of a particular treatment in addressing abnormal shaping of the cornea depends on the stability of the changes in the corneal structure after the treatment has been applied.

Although treatments may initially achieve desired reshaping of the cornea, the desired effects of reshaping the cornea may be mitigated or reversed at least partially if the collagen fibrils within the cornea continue to change after the desired reshaping has been achieved. For instance, a complication known as post-LASIK ectasia may occur due to the thinning and weakening of the cornea caused by LASIK surgery. In post-LASIK ectasia, the cornea experiences progressive steepening (bulging). To strengthen and stabilize the structure of the cornea after reshaping, some treatments may also initiate cross-linking in the corneal tissue. For example, a photosensitizing agent (e.g., riboflavin) is applied to the cornea as a cross-linking agent. Once the cross-linking agent has been applied to the cornea, the cross-linking agent is activated by a light source (e.g., ultraviolet (UV) light) to cause the cross-linking agent to absorb enough energy to cause the release of free oxygen radicals (e.g., singlet oxygen) and/or other radicals within the cornea. Once released, the radicals form covalent bonds between corneal collagen fibrils and thereby cause the corneal collagen fibrils to cross-link and strengthen and stabilize the structure of the cornea.

Due to the advantageous structural changes caused by the cross-linking agent, the cross-linking agent may be applied as the primary aspect of some treatments. For example, a cross-linking agent may be applied to treat keratoconus. Cross-linking treatments may also be employed to induce refractive changes in the cornea to correct disorders such as myopia, hyperopia, astigmatism, irregular astigmatism, presbyopia, etc.

U.S. Patent Application Publication No. 2011/0237999, filed Mar. 18, 2011; U.S. Patent Application Publication No. 2012/0215155, filed Apr. 3, 2012; U.S. Patent Application No. 2014/0343480, filed May 19, 2014; U.S. Patent Application No. 2013/0060187, filed Oct. 31, 2012; International Patent Application Publication No. 2011/130356, filed Apr. 13, 2011; International Patent Application Publication No. 2015/130944, filed Feb. 26, 2015; and International Patent Application No. 2016/090016, filed Dec. 2, 2015 described systems and compositions (e.g., ophthalmic solutions of riboflavin or riboflavin phosphate phosphate) for generating cross-linking activity in the cornea of an eye in treatment of eye disorders e.g., keratoconus (e.g., progressive keratoconus) or corneal ectasia following refractive surgery with or without the removal of corneal epithelium cells. PHOTREXA® VISCOUS (riboflavin 5'-phosphate in 20% dextran ophthalmic solution) 0.146% and PHOTREXA® (riboflavin 5'-phosphate ophthalmic solution) 0.146% are photo enhancers indicated for use with the KXL™ System in corneal collagen cross-linking for the treatment of progressive keratoconus.

U.S. Patent Application Publication No. 20160083352 disclosed diazirine compounds as photocrosslinkers for use e.g., in electronic and optoelectronic devices.

SUMMARY

This disclosure features chemical entities (e.g., a compound or a pharmaceutically acceptable salt and/or hydrate and/or prodrug of the compound) that that generates cross-linking in the cornea in response to exposure to an electromagnetic irradiation. This disclosure also features compositions containing the same as well as other methods of using and making the same. The chemical entities are useful, e.g., for treating a subject (e.g., a human) having a disease, disorder, or condition in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. Non-limiting examples of such diseases, disorders, or conditions include: (i) corneal ectatic disorders; (ii) vision conditions; and (iii) diseases, disorders, or conditions that are sequela or comorbid with any of the foregoing or any disclosed herein. More particular non-limiting examples of such diseases, disorders, or conditions include keratoconus, keratoglobus, pellucid marginal degeneration, corneal ectasia (e.g., post-operative ectasia, e.g., post-LASIK ectasia), Terrien's marginal degeneration, myopia, hyperopia, astigmatism, irregular astigmatism, and presbyopia. In some embodiments, the claimed methods can be performed in the absence of added or supplemental oxygen levels, which can be advantageous in some applications.

In one aspect, the featured chemical entities include compounds of Formula I, or a pharmaceutically acceptable salt thereof:

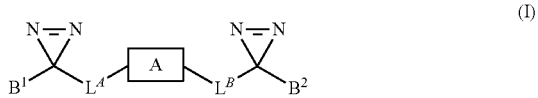

wherein $A^1$, $B^1$, and $B^2$ are as defined herein.

In one aspect, the featured chemical entities include compounds of Formula I, or a pharmaceutically acceptable salt thereof:

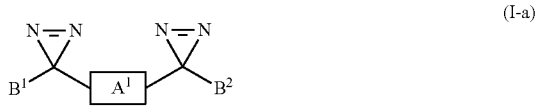

wherein $A^1$, $B^1$, and $B^2$ are as defined herein.

In one aspect, the featured chemical entities include compounds of Formula I, or a pharmaceutically acceptable salt thereof:

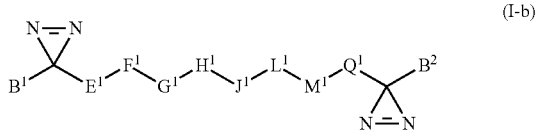

wherein $E^1$, $F^1$, $G^1$, $H^1$, $J^1$, $L^1$, $M^1$, $Q^1$, $B^1$, and $B^2$ are as defined herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for generating cross-linking in a cornea are featured that include contacting the cornea with a chemical entity described herein (e.g., a compound described generically or specifically herein or a pharmaceutically acceptable salt thereof or compositions containing the same); and applying an electromagnetic radiation to the cornea. Such methods can include, e.g., administering the chemical entity to a cornea of an eye in a subject (e.g., a human) having a disease, disorder, or condition in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition (e.g., keratoconus, keratoglobus, pellucid marginal degeneration, corneal ectasia (e.g., post-operative ectasia, e.g., post-LASIK ectasia), Terrien's marginal degeneration, myopia, hyperopia, astigmatism, irregular astigmatism, and presbyopia); and apply an electromagnetic radiation to the cornea. Methods can include, but are not limited to, providing refractive correction to a cornea (e.g., by imparting mechanical stiffness) and strengthen and stabilize the structure of a cornea.

In another aspect, methods of treatment of a disease, disorder, or condition are featured in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. The methods include administering a chemical entity described herein (e.g., a compound described generically or specifically herein, a pharmaceutically acceptable salt thereof or compositions containing the same) in an amount effective to treat the disease, disorder, or condition.

In a further aspect, methods of treatment of a disease, disorder, or condition are featured in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. The methods include administering to a cornea of an eye in a subject in need of such treatment an effective amount of a chemical entity described herein (e.g., a compound described generically or specifically herein, a pharmaceutically acceptable salt thereof, or compositions containing the same); and applying an electromagnetic radiation to the cornea.

A non-limiting example of such diseases, disorders, and conditions is a corneal ectatic disorder. In certain embodiments, the corneal ectatic disorder is keratoconus. In certain embodiments, the corneal ectatic disorder is keratoglobus. In certain embodiments, the corneal ectatic disorder is pellucid marginal degeneration. In certain embodiments, the corneal ectatic disorder is corneal ectasia (e.g., post-operative ectasia, e.g., post-LASIK ectasia). In certain embodiments, the corneal ectatic disorder is Terrien's marginal degeneration.

Another non-limiting example of such diseases, disorders, and conditions is a vision condition. In certain embodiments, the vision condition is myopia. In certain embodiments, the vision condition is hyperopia. In certain embodiments, the vision condition is myopia. In certain embodiments, the vision condition is hyperopia. In certain embodiments, the vision condition is astigmatism. In certain embodiments, the vision condition is irregular astigmatism. In certain embodiments, the vision condition is presbyopia.

Embodiments can include one of more of the following advantageous properties.

In some embodiments, the claimed methods can be performed in the absence of added or supplemental oxygen levels, which can be advantageous in some applications.

In some embodiments, chemical entities and compositions described herein can be applied to a cornea without prior removal of the corneal epithelial cells, thereby resulting in improved patient comfort.

In some embodiments, the chemical entities and compositions described herein can undergo cross-linking in the cornea using relatively short durations of electromagnetic radiation.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of a chemical entity (e.g., a compound described generically or specifically herein, a pharmaceutically acceptable salt thereof, or compositions containing the same) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 21st ed.; Lippincott Williams & Wilkins: Philadelphia, PA, 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, FL, 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid: organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "haloalkoxy" refers to an —O-haloalkyl radical (e.g., —OCF$_3$).

The term "alkylene" refers to a branched or unbranched divalent alkyl (e.g., —CH$_2$—).

The term "arylene" and the like refer to divalent forms of the ring system, here divalent aryl.

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyridazine, pyrimidine, pyrazine, [1,2,3]triazine, [1,2,4]triazine, [1,3,5]triazine, indole, isoindole, benzofuran, benzothiophene [1,3]benzoxazole, [1,3]benzothiazole, benzoimidazole, indazole, quinoline, isoquinoline, cinnoline, quinazoline, quinoxaline, phthalazine, different naphthyridines, e.g. [1,8]naphthyridine, different thienopyridines, e.g. thieno[2,3-b]pyridine and purine.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the description below and in the accompanying Appendix, which is expressly considered part of this disclosure. Other features and advantages will also be apparent from the claims.

DETAILED DESCRIPTION

This disclosure features chemical entities (e.g., a compound or a pharmaceutically acceptable salt and/or hydrate and/or prodrug of the compound) that that generates cross-linking in the cornea in response to exposure to an electromagnetic irradiation. This disclosure also features compositions containing the same as well as other methods of using and making the same. The chemical entities are useful, e.g., for treating a subject (e.g., a human) having a disease, disorder, or condition in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. Non-limiting examples of such diseases, disorders, or conditions include: (i) corneal ectatic disorders; (ii) vision conditions; and (iii) diseases, disorders, or conditions that are sequela or comorbid with any of the foregoing or any disclosed herein. More particular non-limiting examples of such diseases, disorders, or conditions include keratoconus, keratoglobus, pellucid marginal degeneration, corneal ectasia (e.g., post-operative ectasia, e.g., post-LASIK ectasia), Terrien's marginal degeneration, myopia, hyperopia, astigmatism, irregular astigmatism, and presbyopia. In some embodiments, the claimed methods can be performed in the absence of added or supplemental oxygen levels, which can be advantageous in some applications.

Formula (I) Compounds

In one aspect, this disclosure features compounds of Formula (I):

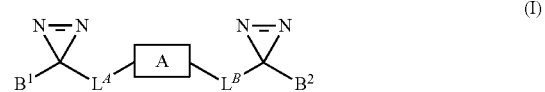

or a pharmaceutically acceptable salt thereof,
wherein:
each of $L^A$ and $L^B$ is independently $C_1$-$C_5$ alkylene, which is optionally substituted with from 1-3 $R^a$;
A is a moiety that enhances delivery of the compound to corneal stroma (e.g., through an intact corneal epithelium) and/or enhances binding of the compound to corneal collagen;
each of $B^1$ and $B^2$ is independently —$Z^1$—$Z^2$—$Z^3$, wherein:
$Z^1$ is $C_{1-3}$ alkylene, which is optionally substituted with from 1-4 $R^a$;
$Z^2$ is a bond, —N($R^d$)—, —O—, or —S—; and
$Z^3$ is halo, H, or $C_{1-7}$ alkyl, which is optionally substituted with from 1-4 $R^a$;
each occurrence of $R^a$ is independently selected from the group consisting of: —OH; —SH; —F; —Cl; —Br; —NR$^e$R$^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$(NR'R''); —S(O)$_{1-2}$($C_{1-4}$ alkyl); cyano; —NR'C(=NR')NR'R''; and $C_{3-6}$ cycloalkyl optionally substituted with from 1-4 independently selected $R^b$;
each occurrence of $R^b$ is independently selected from the group consisting of: —OH; —SH; —F; —Cl; —Br; —NR$^e$R$^f$; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R"); oxo; —S(O)$_{1-2}$(NR'R"); —S(O)$_{0-2}$(C$_{1-4}$ alkyl); cyano; —NR'C(=NR')NR'R"; and C$_{3-6}$ cycloalkyl optionally substituted with from 1-4 independently selected C$_{1-4}$ alkyl;

each occurrence of R$^d$ is selected from the group consisting of: H, C$_{1-6}$ alkyl; C$_{3-6}$ cycloalkyl; —C(O)(C$_{1-4}$ alkyl); —C(O)O(C$_{1-4}$ alkyl); —CON(R')(R"); —S(O)$_{1-2}$(NR'R"); —S(O)$_{1-2}$(C$_{1-4}$ alkyl); —OH; and C$_{1-4}$ alkoxy;

each occurrence of R$^e$ and R$^f$ is independently selected from the group consisting of: H; C$_{1-6}$ alkyl; C$_{3-6}$ cycloalkyl; —C(O)(C$_{1-4}$ alkyl); —C(O)O(C$_{1-4}$ alkyl); —CON(R')(R"); —S(O)$_{1-2}$(NR'R"); —S(O)$_{1-2}$(C$_{1-4}$ alkyl); —OH; and C$_{1-4}$ alkoxy; and each occurrence of R' and R" is independently selected from the group consisting of: H and C$_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and C$_{1-3}$ alkyl; and (b) from 0-3 ring heteroatoms (in addition to the nitrogen atom attached to R' and R"), which are each independently selected from the group consisting of N(R$^d$), O, and S.

Variable A

In some embodiments of Formula (I), A is a moiety that enhances delivery of the compound to corneal stroma (e.g., through an intact corneal epithelium) and/or enhances binding of the compound to corneal collagen; In some embodiments of Formula (I), A is a moiety that enhances delivery of the compound to corneal stroma through an intact corneal epithelium and/or enhances binding of the compound to corneal collagen.

In some embodiments of Formula (I), A is a moiety (e.g., a small molecule moiety) that is able to penetrate corneal epithelium cells.

In some embodiments, A is a peptide moiety.

In certain embodiments, A is attached to L$^A$ at the N-terminus and to L$^B$ at the C-terminus. In certain other embodiments of Formula (I), A is attached to L$^A$ at the C-terminus and to L$^B$ at the N-terminus.

In certain embodiments, A is a peptide moiety taken from a decorin sequence that binds collagen. In certain embodiments of the foregoing, A is a peptide moiety taken from a decorin sequence that binds collagen type I (e.g., A is a peptide moiety taken from the decorin sequence SYIRIADTNIT reported in J. Biol. Chem. 2007, 282, 16062, which is incorporated in its entirety herein by reference). As a non-limiting example of the foregoing embodiments, A can comprise a peptide moiety of the sequence RIAD.

In certain embodiments, A is a peptide moiety taken from an asporin sequence (e.g., A is a peptide moiety taken from the asporin sequence HIRIAEAKLT reported in J. Biol. Chem. 2007, 282, 16062, which is incorporated in its entirety herein by reference). As a non-limiting example of the foregoing embodiments, A can be a peptide moiety of the sequence RIAE.

In certain embodiments, A is a peptide moiety taken from a biglycan sequence (e.g., A is a peptide moiety taken from the asporin sequence NYLRISEAKLT reported in J. Biol. Chem. 2007, 282, 16062, which is incorporated in its entirety herein by reference.

In certain embodiments, A is a moiety that binds lumican and/or fibromodulin.

Variables L$^A$ and L$^B$

In some embodiments of Formula (I), each of L$^A$ and L$^B$ is independently C$_1$-C$_3$ alkylene, which is optionally substituted with from 1-3 R$^a$.

In certain embodiments of the foregoing, each of L$^A$ and L$^B$ is independently C$_1$-C$_3$ alkylene, which is optionally substituted with from 1 R$^a$.

As a non-limiting example of the foregoing embodiments, each of L$^A$ and L$^B$ can be independently unsubstituted C$_1$-C$_3$ alkylene (e.g., unsubstituted C$_{2-3}$ alkylene; e.g., unsubstituted ethylene or propylene).

Variables B$^1$ and B$^2$

In some embodiments of Formula (I), each of B$^1$ and B$^2$ is independently —Z$^1$—Z$^3$ (i.e., Z$^2$ is a bond).

In some embodiments of Formula (I), Z$^3$ is H, halo, or C$_{1-3}$ alkyl.

In some embodiments of Formula (I), Z$^3$ is H or C$_{1-3}$ alkyl (e.g., Z$^3$ can be H).

In some embodiments of Formula (I), Z$^3$ is halo (e.g., Z$^3$ can be F).

In some embodiments of Formula (I), Z$^1$ is C$_{1-3}$ alkylene which is optionally substituted with 1-3 independently selected R$^a$ (e.g., Z$^1$ can be methylene, CHF, or CF$_2$).

In certain embodiments, Z$^1$ is unsubstituted C$_{1-3}$ alkylene (e.g., CH$_2$).

In certain embodiments, Z$^1$ is unsubstituted C$_{1-3}$ alkylene; and Z$^3$ is H.

In certain embodiments, Z$^1$ is C$_{1-3}$ alkylene substituted with from 1-2 independently selected halo (e.g., F).

In certain embodiments, each of B$^1$ and B$^2$ is independently selected from CH$_3$, CHR$^a$, CH(R$^a$)$_2$, and C(R$^a$)$_2$-halo.

As non-limiting examples of the foregoing embodiments, each of B$^1$ and B$^2$ can be independently CH$_3$, CHF$_2$, CH$_2$F, and CF$_3$ (e.g., CH$_3$).

Formula (I-a) Compounds

In another aspect, this disclosure features compounds of Formula (I-a):

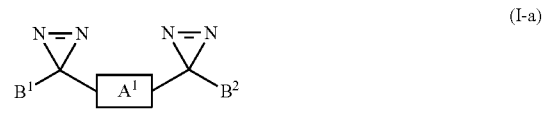

(I-a)

wherein A$^1$ is a C$_2$-C$_{20}$ alkylene, which is interrupted with from 1-10 (e.g., 1-5, 1-4, 1-3, 1-2, 1) R$^1$;

each of B$^1$ and B$^2$ is independently —Z$^1$—Z$^2$—Z$^3$, wherein:

Z$^1$ is C$_{1-3}$ alkylene, which is optionally substituted with from 1-4 R$^a$;

Z$^2$ is a bond, —N(R$^d$)—, —O—, or —S—; and

Z$^3$ is halo, H or C$_{1-7}$ alkyl, which is optionally substituted with from 1-4 R$^a$;

each occurrence of R$^1$ is a divalent group that independently selected from:

—N(R$^{d1}$)—

—N(R$^3$)—;

—O—;

S(O)$_p$, wherein p is 0, 1, or 2;

C(=O);

C(=S);

CHR$^2$;

C(R$^2$)$_2$;

—C(=O)CH(R$^2$)N(R$^{d1}$)—; and

—C(=O)CH(R$^2$)CH$_2$N(R$^{d1}$)—;

each occurrence of $R^2$ is independently selected from the group consisting of:

(i) $R^a$;

(ii) $C_1$-$C_6$ alkyl, which is optionally substituted with 1-3 $R^a$;

(iii) $L^2$-heterocyclyl, wherein the heterocyclyl includes from 3-10 ring atoms, wherein from 1-3 ring atoms are heteroatoms, each independently selected from the group consisting of N($R^d$), O, and S, and wherein one or more of the heterocyclyl ring carbon atoms are optionally substituted with from 1-4 independently selected $R^b$, (iv) $L^2$-$C_6$-$C_{10}$ aryl, which is optionally substituted with from 1-4 $R^c$;

(v) $L^2$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$; and (vi) H; or (vii) $R^2$ and $R^{d1}$, in the —C(═O)CH($R^2$) N($R^{d1}$)— group, combine to form a ring including from 5-8 ring atoms, wherein the ring includes: (a) from 3-6 ring carbon atoms (in addition to CH($R^2$)), each of which is substituted with from 1-2 substituents independently selected from H and $C_{1-3}$ alkyl; and (b) from 0-3 ring heteroatoms (in addition to the nitrogen atom attached to $R^{d1}$), which are each independently selected from the group consisting of N($R^{d1}$), O, and S;

each occurrence of $R^3$ is independently selected from the group consisting of:

(i) $C_1$-$C_6$ alkyl, which is optionally substituted with 1-3 $R^a$;

(ii) $L^3$-heterocyclyl, wherein the heterocyclyl includes from 3-10 ring atoms, wherein from 1-3 ring atoms are heteroatoms, each independently selected from the group consisting of N($R^d$), O, and S, and wherein one or more of the heterocyclyl ring carbon atoms are optionally substituted with from 1-4 independently selected $R^b$, (iii) $L^3$-$C_6$-$C_{10}$ aryl, which is optionally substituted with from 1-4 $R^c$; and (iv) $L^3$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$;

each occurrence of $R^a$ is independently selected from the group consisting of: —OH; —SH; —F; —Cl; —Br; —NR$^e$R$^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R''); —S(O)$_{1-2}$(NR'R''); —S(O)$_{0-2}$($C_{1-4}$ alkyl); cyano; —NR'C(═NR')NR'R''; and $C_{3-6}$ cycloalkyl optionally substituted with from 1-4 independently selected $R^b$;

each occurrence of $R^b$ is independently selected from the group consisting of: —OH; —SH; —F; —Cl; —Br; —NR$^e$R$^f$; $C_{1-4}$ alkyl; $C_{1-4}$ haloalkyl; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R''); oxo; —S(O)$_{1-2}$(NR'R''); —S(O)$_{0-2}$($C_{1-4}$ alkyl); cyano; —NR'C(═NR')NR'R''; and $C_{3-6}$ cycloalkyl optionally substituted with from 1-4 independently selected $C_{1-4}$ alkyl;

each occurrence of $R^c$ is independently selected from the group consisting of: —OH; —SH; —F; —Cl; —Br; —NR$^e$R$^f$; $C_{1-4}$ alkyl; $C_{1-4}$ haloalkyl; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R''); —S(O)$_{1-2}$(NR'R''); —S(O)$_{0-2}$($C_{1-4}$ alkyl); cyano; —NR'C(═NR')NR'R''; and $C_{3-6}$ cycloalkyl optionally substituted with from 1-4 independently selected $C_{1-4}$ alkyl;

each occurrence of $R^d$ is selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; and each occurrence of R' and R'' is independently selected from the group consisting of: H and $C_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N($R^d$), O, and S;

each occurrence of $R^{d1}$ is selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; or $R^2$ and $R^{d1}$, in the —C(═O)CH($R^2$) N($R^{d1}$)— group, combine to form a ring including from 5-8 ring atoms as defined above;

and each of $L^2$ and $L^3$ in each occurrence is independently a bond or a $C_1$-$C_6$ alkylene optionally substituted with 1-3 substituents independently selected from oxo and $R^a$.

Variable $A^1$

In some embodiments of Formula (I-a), $A^1$ is a $C_4$-$C_6$ alkylene, which is interrupted with from 1-4 (e.g., 1, 2-3, 3-4, 2, 3, or 4) independently selected $R^1$.

In certain embodiments, $A^1$ is a $C_4$-$C_6$ alkylene, which is interrupted with from 1-4 (e.g., 1, 2-3, 3-4, 2, 3, or 4) independently selected $R^1$.

In certain embodiments, $A^1$ is interrupted with 1 independently selected $R^1$.

In certain embodiments, $A^1$ is interrupted with from 2-3 (e.g., 2 or 3) independently selected $R^1$.

In certain embodiments, $A^1$ is interrupted with from 3-4 (e.g., 3 or 4) independently selected $R^1$.

In certain embodiments, $A^1$ is interrupted with from 1-3 independently selected $R^1$.

In certain embodiments, $A^1$ is interrupted with from 2-4 independently selected $R^1$.

Variable $R^1$

In some embodiments of Formula (I-a), one $R^1$ is independently —C(═O)CH($R^2$)N($R^{d1}$)— or —N($R^3$)— (e.g., one $R^1$ is —C(═O)CH($R^2$)N($R^{d1}$)—; or one $R^1$ is —N($R^3$)—).

In certain embodiments of the foregoing, each of the other $R^1$ groups is independently selected from the group consisting of: —N($R^{d1}$)—, (C=O), —O—, S(O)P, —C(=O)CH($R^2$)N($R^{d1}$)—, and —C(=O)CH($R^2$)CH$_2$N($R^{d1}$)—.

As non-limiting examples of the foregoing embodiments, each of the other $R^1$ groups can be independently selected from the group consisting of: —N(H)—, (C=O), —O—, S(O)$_2$, —C(=O)CH($R^2$)N(H)—, and —C(=O)CH$_2$CH$_2$N(H)—.

Variables $R^2$ and $R^3$

In some embodiments of Formula (I-a), $R^2$ is H.

In some embodiments of Formula (I-a), $R^2$ is $C_1$-$C_6$ alkyl, which is optionally substituted with 1-3 $R^a$.

In certain embodiments, $R^2$ is $C_1$-$C_4$ alkyl, which is optionally substituted with 1-2 $R^a$ (e.g., $C_1$-$C_4$ alkyl substituted with 1 $R^a$).

In certain embodiments of foregoing (when $R^2$ is $C_1$-$C_4$ alkyl, which is optionally substituted with 1-2 $R^a$ (e.g., $C_1$-$C_4$ alkyl substituted with 1 $R^a$)), each $R^a$ is independently selected from: —OH; —SH; —NR$^e$R$^f$; —C(=O)O($C_{1-4}$ alkyl); —C(=O)OH; —CON(R')(R''); —S(O)$_{1-2}$(NR'R''); —S(O)$_{0-2}$($C_{1-4}$ alkyl); cyano; and —NR'C(=NR')NR'R''.

As non-limiting examples of the foregoing embodiments, each $R^a$ can be independently selected from: —NH$_2$, —OH, —SH, —SMe, —NH(C=NH)NH$_2$, CO$_2$H, and CO$_2$NH$_2$ (e.g., each $R^a$ can be independently selected from —NH$_2$, —OH, —NH(C=NH)NH$_2$, CO$_2$H, and CO$_2$NH$_2$).

In some embodiments of Formula (I-a), $R^2$ is:

$L^2$-$C_6$-$C_{10}$ aryl, which is optionally substituted with from 1-4 $R^e$; or $L^2$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$.

In certain embodiments, $R^2$ is $L^2$-phenyl, wherein the phenyl is optionally substituted with from 1-2 $R^c$.

In certain embodiments, $R^2$ is $L^2$-heteroaryl, wherein the heteroaryl includes from 5-9 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-2 independently selected $R^c$.

As non-limiting examples of the foregoing embodiments, $R^2$ can be $L^2$-indolyl or $L^2$-imidazolyl, wherein the indolyl or imidazolyl is optionally substituted with from 1-2 independently selected $R^c$.

In certain embodiments of the foregoing (when $R^2$ is $L^2$-$C_6$-$C_{10}$ aryl, which is optionally substituted with from 1-4 $R^c$; or $L^2$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$), each $R^c$ is independently selected from —OH; —SH; —F; —Cl; —Br; —NR$^e$R$^f$; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)OH; —CON(R')(R''); —S(O)$_{1-2}$(NR'R''); —S(O)$_{0-2}$($C_{1-4}$ alkyl); cyano; — and $C_{3-6}$ cycloalkyl optionally substituted with from 1-4 independently selected $C_{1-4}$ alkyl.

As non-limiting examples of the foregoing embodiments, each $R^c$ can be independently selected from —OH, F, —NR$^e$R$^f$, $C_{1-4}$ alkyl; and $C_{1-4}$ haloalkyl (e.g., $R^c$ is OH).

In certain embodiments, $L^2$ is a $C_{1-6}$ (e.g., $C_{1-4}$) alkylene optionally substituted with 1-3 $R^a$ (e.g., unsubstituted).

In some embodiments of Formula (I-a), each occurrence of $R^2$ independently is selected from:

H;

$C_1$-$C_6$ alkyl optionally substituted with 1-2 substituents selected from —NH$_2$, —OH, —SH, —SMe, —NH(C=NH)NH$_2$, CO$_2$H, and CO$_2$NH$_2$;

($C_1$-$C_6$ alkylene)-phenyl, optionally substituted with 1-2 —OH;

($C_1$-$C_6$ alkylene)-indolyl; and ($C_1$-$C_6$ alkylene)-imidazolyl; or $R^2$ and $R^{d1}$, in the —CH($R^2$)N($R^{d1}$)— group, combine to form a pyrrolidine ring.

In certain embodiments, each occurrence of $R^2$ is independently selected from:

H;

$C_1$-$C_6$ alkyl optionally substituted with 1-2 substituents selected from —NH$_2$, —OH, —NH(C=NH)NH$_2$, CO$_2$H, and CO$_2$NH$_2$; and ($C_1$-$C_6$ alkylene)-imidazolyl.

As non-limiting examples of the foregoing embodiments, each occurrence of $R^2$ can be independently selected from:

H;

[Chemical structures shown: various side chain groups including alkyl-NH$_2$ chains, guanidino groups (HN=C(NH$_2$)NH—), CONH$_2$, CO$_2$H, OH, and imidazolyl side chains]

In some embodiments of Formula (I-a), each occurrence of $R^3$ is independently selected from:

$C_1$-$C_6$ alkyl optionally substituted with 1-2 substituents selected from —NH$_2$, —OH, —SH, —SMe, —NH(C=NH)NH$_2$, CO$_2$H, and CO$_2$NH$_2$;

($C_1$-$C_6$ alkylene)-phenyl, optionally substituted with 1-2 —OH;

($C_1$-$C_6$ alkylene)-indolyl; and ($C_1$-$C_6$ alkylene)-imidazolyl.

In some embodiments of Formula (I-a), $R^3$ is $C_1$-$C_6$ alkyl, which is optionally substituted with 1-3 $R^a$.

In certain embodiments, $R^3$ is $C_1$-$C_4$ alkyl, which is optionally substituted with 1-2 $R^a$ (e.g., $C_1$-$C_4$ alkyl substituted with 1 $R^a$).

In certain embodiments of foregoing (when $R^3$ is $C_1$-$C_4$ alkyl, which is optionally substituted with 1-2 $R^a$ (e.g., $C_1$-$C_4$ alkyl substituted with 1 $R^a$)), each $R^a$ is independently selected from: —OH; —SH; —NR$^e$R$^f$; —C(=O)O($C_{1-4}$ alkyl); —C(=O)OH; —CON(R')(R''); —S(O)$_{1-2}$(NR'R''); —S(O)$_{0-2}$($C_{1-4}$ alkyl); cyano; and —NR'C(=NR')NR'R''.

As non-limiting examples of the foregoing embodiments, each $R^a$ can be independently selected from: —NH$_2$, —OH, —SH, —SMe, —NH(C=NH)NH$_2$, CO$_2$H, and CO$_2$NH$_2$ (e.g., each $R^a$ can be independently selected from —NH$_2$, —OH, —NH(C=NH)NH$_2$, CO$_2$H, and CO$_2$NH$_2$; e.g., each $R^a$ can be independently selected from —NH$_2$ and CO$_2$H).

In some embodiments of Formula (I-a), $R^3$ is $L^3$-$C_6$-$C_{10}$ aryl, which is optionally substituted with from 1-4 $R^e$; or $L^3$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$.

In certain embodiments, $R^3$ is $L^3$-phenyl, wherein the phenyl is optionally substituted with 1-2 $R^c$.

In certain embodiments, $R^3$ is $L^3$-heteroaryl, wherein the heteroaryl includes from 5-8 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-2 independently selected $R^c$.

As non-limiting examples of the foregoing embodiments, $R^3$ can be $L^3$-indolyl or $L^3$-imidazolyl, wherein the indolyl or imidazolyl is optionally substituted with from 1-2 independently selected $R^c$.

In certain embodiments of the foregoing (when $R^3$ is $L^2$-$C_6$-$C_{10}$ aryl, which is optionally substituted with from 1-4 $R^c$ or $L^3$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$), each $R^c$ is independently selected from —OH; —SH; —F; —Cl; —Br; —NR$^e$R$^f$; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)OH; —CON(R')(R''); —S(O)$_{1-2}$(NR'R''); —S(O)$_{0-2}$($C_{1-4}$ alkyl); cyano; — and $C_{3-6}$ cycloalkyl optionally substituted with from 1-4 independently selected $C_{1-4}$ alkyl.

As non-limiting examples of the foregoing embodiments, each $R^c$ can be independently selected from —OH, F, —NR$^e$R$^f$, $C_{1-4}$ alkyl; and $C_{1-4}$ haloalkyl (e.g., $R^c$ is OH).

In certain embodiments, $L^3$ is a $C_{1-6}$ (e.g., $C_{1-4}$) alkylene optionally substituted with 1-3 $R^a$ (e.g., unsubstituted).

In certain embodiments, $L^3$ is a $C_{1-6}$ (e.g., $C_{1-4}$) alkylene substituted with one oxo. As a non-limiting example of the foregoing, $L^3$ can be

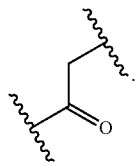 [SMILES: *CC(*)=O]

In certain embodiments, $L^3$ is a bond.

In certain embodiments, each occurrence of $R^3$ is independently selected from:

$C_1$-$C_6$ alkyl optionally substituted with 1-2 substituents selected from —NH$_2$, —OH, —NH(C=NH)NH$_2$, CO$_2$H, and CO$_2$NH$_2$; and ($C_1$-$C_6$ alkylene)-imidazolyl.

As non-limiting examples of the foregoing embodiments, each occurrence of $R^3$ can be independently selected from:

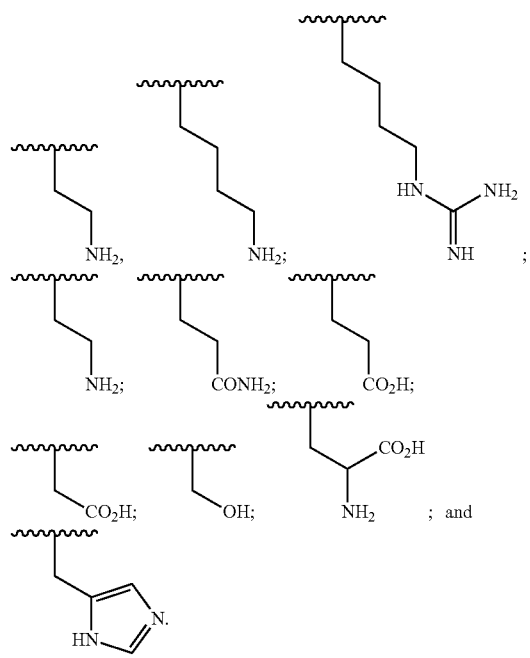

In certain embodiments, each occurrence of $R^3$ is independently selected from: $C_1$-$C_6$ alkyl optionally substituted with 1-2 substituents selected from —NH$_2$, —OH, —NH(C=NH)NH$_2$, CO$_2$H, and CO$_2$NH$_2$.

As non-limiting examples of the foregoing embodiments, each occurrence of $R^3$ can be independently selected from:

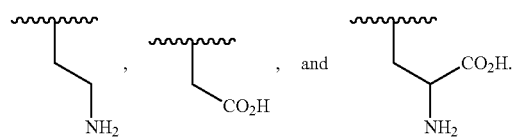

In some embodiments, each occurrence of $R^3$ is independently selected from: $L^3$-heterocyclyl, wherein the heterocyclyl includes from 3-10 ring atoms, wherein from 1-3 ring atoms are heteroatoms, each independently selected from the group consisting of N($R^d$), O, and S, and wherein one or more of the heterocyclyl ring carbon atoms are optionally substituted with from 1-4 independently selected $R^b$.

In certain embodiments, each occurrence of $R^3$ is independently selected from: $L^3$-heterocyclyl, wherein the heterocyclyl includes from 4-6 (e.g., 5-6) ring atoms, wherein from 1-3 ring atoms are heteroatoms, each independently selected from the group consisting of N($R^d$), O, and S, and wherein one or more of the heterocyclyl ring carbon atoms are optionally substituted with from 1-2 independently selected $R^b$ (e.g., heterocyclyl can be pyrrolidinyl, piperidinyl, or morpholinyl).

In certain of these embodiments, $L^3$ is a bond.

In certain embodiments (when each occurrence of $R^3$ is independently selected from: $L^3$-heterocyclyl, wherein the heterocyclyl includes from 3-10 ring atoms, wherein from 1-3 ring atoms are heteroatoms, each independently selected from the group consisting of $N(R^d)$, O, and S, and wherein one or more of the heterocyclyl ring carbon atoms are optionally substituted with from 1-4 independently selected $R^b$), $L^3$ is $C_{1-6}$ alkyl optionally substituted with from 1-3 independently selected $R^a$ (e.g., unsubstituted).

In certain embodiments (when each occurrence of $R^3$ is independently selected from: $L^3$-heterocyclyl, wherein the heterocyclyl includes from 3-10 ring atoms, wherein from 1-3 ring atoms are heteroatoms, each independently selected from the group consisting of $N(R^d)$, O, and S, and wherein one or more of the heterocyclyl ring carbon atoms are optionally substituted with from 1-4 independently selected $R^b$), $L^3$ is a $C_{1-6}$ (e.g., $C_{1-4}$) alkylene substituted with one oxo (e.g., can be

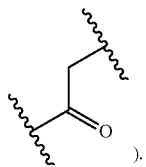 [SMILES: *CC(*)=O]
).

As non-limiting examples, $R^3$ can be selected from:

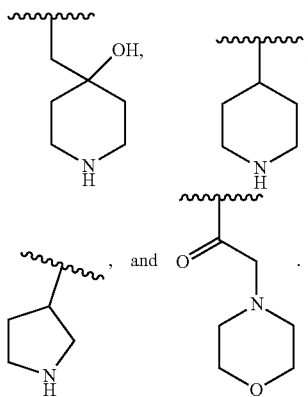

Variables $B^1$ and $B^2$

In some embodiments of Formula (I-a), each of $B^1$ and $B^2$ is independently —$Z^1$—$Z^3$ (i.e., $Z^2$ is a bond).

In some embodiments of Formula (I-a), $Z^3$ is H, halo, or $C_{1-3}$ alkyl.

In some embodiments of Formula (I-a), $Z^3$ is H or $C_{1-3}$ alkyl (e.g., $Z^3$ can be H).

In some embodiments of Formula (I-a), $Z^3$ is halo (e.g., $Z^3$ can be F).

In some embodiments of Formula (I-a), $Z^1$ is $C_{1-3}$ alkylene which is optionally substituted with 1-3 independently selected $R^a$ (e.g., $Z^1$ can be methylene, CHF, or $CF_2$).

In certain embodiments, $Z^1$ is unsubstituted $C_{1-3}$ alkylene (e.g., $CH_2$).

In certain embodiments, $Z^1$ is unsubstituted $C_{1-3}$ alkylene; and $Z^3$ is H.

In certain embodiments, Z is $C_{1-3}$ alkylene substituted with from 1-2 independently selected halo (e.g., F).

In certain embodiments, each of $B^1$ and $B^2$ is independently selected from $CH_3$, $CHR^a$, $CH(R^a)_2$, and $C(R^a)_2$-halo.

As non-limiting examples of the foregoing embodiments, each of $B^1$ and $B^2$ can be independently $CH_3$, $CHF_2$, $CH_2F$, or $CF_3$ (e.g., $CH_3$).

Variable $R^{d1}$

In some embodiments of Formula (I-a), each occurrence of $R^{d1}$ is independently selected from the group consisting of: each occurrence of $R^{d1}$ is selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); and —S(O)$_{1-2}$($C_{1-4}$ alkyl); or $R^2$ and $R^{d1}$, in the —C(=O)CH($R^2$) N($R^{d1}$)— group, combine to form a ring including from 5-8 ring atoms as defined above.

In certain embodiments, each occurrence of $R^{d1}$ is independently selected from the group consisting of: H, $C_{1-6}$ alkyl; and $C_{3-6}$ cycloalkyl.

In certain embodiments, each occurrence of $R^{d1}$ is H.

Formula (I-b) Compounds

In another aspect, this disclosure features a compound of Formula (I-b):

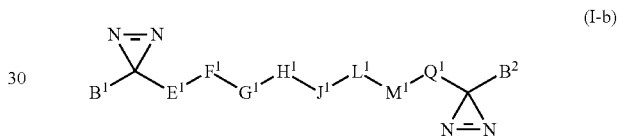

(I-b)

or a pharmaceutically acceptable salt thereof,
wherein
each of $B^1$ and $B^2$ is independently —$Z^1$—$Z^2$—$Z^3$, wherein:
$Z^1$ is $C_{1-3}$ alkylene, which is optionally substituted with from 1-4 $R^a$;
$Z^2$ is a bond, —N($R^d$)—, —O—, or —S—; and
$Z^3$ is H, halo, or $C_{1-7}$ alkyl, which is optionally substituted with from 1-4 $R^a$;
each of $E^1$, $F^1$, $G^1$, $H^1$, $J^1$, $L^1$, $M^1$, and $Q^1$ is independently selected from:
a bond;
$C_1$-$C_6$ alkylene, which is optionally substituted with 1-3 $R^a$; and
$R^1$;
wherein each occurrence of $R^1$ is independently selected from the group consisting of:
—N($R^{d1}$)—
—N($R^3$)—;
—O—;
S(O)$_p$, wherein p is 0, 1, or 2;
C(=O);
C(=S);
CHR$^2$;
C($R^2$)$_2$
—C(=O)CH($R^2$)N($R^{d1}$)—; and
—C(=O)CH($R^2$)CH$_2$N($R^{d1}$)—;
provided that at least one of $E^1$ and $F^1$ is $C_1$-$C_6$ alkylene, which is optionally substituted with 1-3 $R^a$; and provided that from 1-4 of $F^1$, $G^1$, $H^1$, $J^1$, $L^1$, and $M^1$ are each an independently selected $R^1$;

each occurrence of $R^2$ is independently selected from the group consisting of:
(i) $R^a$;
(ii) $C_1$-$C_6$ alkyl, which is optionally substituted with 1-3 $R^a$;
(iii) $L^2$-heterocyclyl, wherein the heterocyclyl includes from 3-10 ring atoms, wherein from 1-3 ring atoms are heteroatoms, each independently selected from the group consisting of $N(R^d)$, O, and S; and wherein one or more of the heterocyclyl ring carbon atoms are optionally substituted with from 1-4 independently selected $R^b$,
(iv) $L^2$-$C_6$-$C_{10}$ aryl, which is optionally substituted with from 1-4 $R^c$;
(v) $L^2$-heteroaryl, wherein the heteroaryl includes from 5-10 ring atoms, wherein from 1-4 ring atoms are heteroatoms, each independently selected from the group consisting of N, $N(R^d)$, O, and S, and wherein one or more of the heteroaryl ring carbon atoms are optionally substituted with from 1-4 independently selected $R^c$; and
(vi) H; or
(vii) $R^2$ and $R^{d1}$, in the —C(=O)CH($R^2$) $N(R^{d1})$— group, combine to form a ring including from 5-8 ring atoms, wherein the ring includes: (a) from 3-6 ring carbon atoms (in addition to CH($R^2$)), each of which is substituted with from 1-2 substituents independently selected from H and $C_{1-3}$ alkyl; and (b) from 0-3 ring heteroatoms (in addition to the nitrogen atom attached to $R^{d1}$), which are each independently selected from the group consisting of $N(R^{d1})$, O, and S;

each occurrence of $R^3$ is independently selected from the group consisting of:
(i) $C_1$-$C_6$ alkyl, which is optionally substituted with 1-3 $R^a$;
(ii) $L^3$-heterocyclyl, wherein the heterocyclyl includes from 3-10 ring atoms, wherein from 1-3 ring atoms are heteroatoms, each independently selected from the group consisting of $N(R^d)$, O, and S, and wherein one or more of the heterocyclyl ring carbon atoms are optionally substituted with from 1-4 independently selected $R^b$,
(iii) $L^3$-$C_6$-$C_{10}$ aryl, which is optionally substituted with from 1-4 $R^c$; and
(iv) $L^3$-heteroaryl, wherein the heteroaryl includes from 5-10 ring atoms, wherein from 1-4 ring atoms are heteroatoms, each independently selected from the group consisting of N, $N(R^d)$, O, and S, and wherein one or more of the heteroaryl ring carbon atoms are optionally substituted with from 1-4 independently selected $R^c$;

each occurrence of $R^a$ is independently selected from the group consisting of: —OH; —SH; —F; —Cl; —Br; —$NR^eR^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$(NR'R''); —S(O)$_{0-2}$($C_{1-4}$ alkyl); cyano; —NR'C(=NR')NR'R''; and $C_{3-6}$ cycloalkyl optionally substituted with from 1-4 independently selected $R^b$;

each occurrence of $R^b$ is independently selected from the group consisting of: —OH; —SH; —F; —Cl; —Br; —$NR^eR^f$; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); oxo; —S(O)$_{1-2}$(NR'R''); —S(O)$_{0-2}$($C_{1-4}$ alkyl); cyano; —NR'C(=NR')NR'R''; and $C_{3-6}$ cycloalkyl optionally substituted with from 1-4 independently selected $C_{1-4}$ alkyl;

each occurrence of $R^c$ is independently selected from the group consisting of: —OH; —SH; —F; —Cl; —Br; —$NR^eR^f$; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$(NR'R''); —S(O)$_{0-2}$($C_{1-4}$ alkyl); cyano; —NR'C(=NR')NR'R''; and $C_{3-6}$ cycloalkyl optionally substituted with from 1-4 independently selected $C_{1-4}$ alkyl;

each occurrence of $R^d$ is selected from the group consisting of: H $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; and each occurrence of R' and R'' is independently selected from the group consisting of: H and $C_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of $N(R^d)$, O, and S.

each occurrence of $R^{d1}$ is selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); —S(O)$_{1-2}$($C_{1-4}$ alkyl); —OH; and $C_{1-4}$ alkoxy; or $R^2$ and $R^{d1}$, in the —C(=O)CH($R^2$) $N(R^{d1})$— group, combine to form a ring including from 5-8 ring atoms as defined above;
and
each of $L^2$ and $L^3$ in each occurrence is independently a bond or a $C_1$-$C_6$ alkylene optionally substituted with 1-3 substituents independently selected from oxo and $R^a$.

In some embodiments of Formula (I-b), from 1-4 of $F^1$, $G^1$, $H^1$, $J^1$, $L^1$, and $M^1$ are each an independently selected $R^1$.

In certain embodiments, from 1-3 (e.g., from 2-3) of $F^1$, $G^1$, $H^1$, $J^1$, $L^1$, and $M^1$ are each an independently selected $R^1$.

In certain embodiments of the foregoing, from 1-2 (e.g., 1 or 2) of $F^1$, $G^1$, $H^1$, $J^1$, $L^1$, and $M^1$ are each an independently selected $R^1$.

In certain embodiments of the foregoing, from 2-3 (e.g., 2 or 3) of $F^1$, $G^1$, $H^1$, $J^1$, $L^1$, and $M^1$ are each an independently selected $R^1$.

In certain embodiments of the foregoing, from 2-4 (e.g., 2, 3, or 4) of $F^1$, $G^1$, $H^1$, $J^1$, $L^1$, and $M^1$ are each an independently selected $R^1$.

Variables $H^1$ and $J^1$

In some embodiments of Formula (I-b), each of $H^1$ and $J^1$ is independently selected from the group consisting of:
a bond;
$C_1$-$C_6$ alkylene, which is optionally substituted with 1-3 $R^a$;
—$N(R^{d1})$—
—$N(R^3)$—;
—O—;
$S(O)_p$, wherein p is 0, 1, or 2;
C(=O);
C(=S);

CHR$^2$;
—C(=O)CH(R$^2$)N(R$^{d1}$)—; and
—C(=O)CH(R$^2$)CH$_2$N(R$^{d1}$)—.

In certain embodiments, each of H$^1$ and J$^1$ is independently selected from the group consisting of:
a bond;
—N(R$^{d1}$)—
—O—;
S(O)$_p$, wherein p is 0, 1, or 2;
C(=O);
C(=S);
CHR$^2$;
—C(=O)CH(R$^2$)N(R$^{d1}$)—; and
—C(=O)CH(R$^2$)CH$_2$N(R$^{d1}$)—.

In some embodiments of Formula (I-b), one of H$^1$ and J$^1$ is independently —C(=O)CH(R$^2$)N(R$^{d1}$)— (e.g., J$^1$ is —C(=O)CH(R$^2$)N(R$^{d1}$)—)

In certain embodiments of the foregoing, the other one of H$^1$ and J$^1$ is independently selected from the group consisting of:
a bond;
—N(R$^{d1}$)—,
—O—
S(O)$_p$, wherein p is 0, 1, or 2;
C(=O);
C(=S);
CHR$^2$;
—C(=O)CH(R$^2$)N(R$^{d1}$)—; and
—C(=O)CH(R$^2$)CH$_2$N(R$^{d1}$)—.

In certain embodiments of the foregoing (when one of H$^1$ and J$^1$ is independently —C(=O)CH(R$^2$)N(R$^{d1}$)— (e.g., J$^1$ is —C(=O)CH(R$^2$)N(R$^{d1}$)—)), the other one of H$^1$ and J$^1$ is independently selected from a bond, —N(R$^{d1}$)—, and —O— (e.g., H$^1$ can be a bond; or H$^1$ can be —N(R$^{d1}$) (e.g., —N(H)—)).

In some embodiments of Formula (I-b), one of H$^1$ and J$^1$ is independently —N(R$^3$)— or —N(R$^{d1}$)—. In certain embodiments of the foregoing, one of H$^1$ and J$^1$ is independently —N(R$^3$)—.

In certain embodiments of the foregoing (when one of H$^1$ and J$^1$ is independently —N(R$^3$)— or —N(R$^{d1}$)—), the other one of H$^1$ and J$^1$ is independently selected from:
bond;
—O—;
S(O)$_p$, wherein p is 0, 1, or 2;
C(=O);
C(=S);
CHR$^2$;
—C(=O)CH(R$^2$)N(R$^{d1}$)—; and
—C(=O)CH(R$^2$)CH$_2$N(R$^{d1}$)—.

As non-limiting examples of the foregoing embodiments, when one of H$^1$ and J$^1$ is independently —N(R$^3$)— or —N(R$^{d1}$)—, the other one of H$^1$ and J$^1$ can be a bond or C(=O).

Variables E$^1$ and Q$^1$

In some embodiments of Formula (I-b), each of E$^1$ and Q$^1$ is an independently selected C$_1$-C$_6$ alkylene, which is optionally substituted with 1-3 R$^a$.

In certain embodiments of the foregoing, each of E$^1$ and Q$^1$ is an independently selected C$_1$-C$_4$ alkylene which is optionally substituted with 1-3 R$^a$.

As a non-limiting example of the foregoing embodiments, each of E$^1$ and Q$^1$ can be an independently selected C$_2$-C$_4$ alkylene (e.g., C$_2$-C$_3$ alkylene, e.g., C$_2$ alkylene) which is unsubstituted.

Variable F$^1$

In some embodiments of Formula (I-b), F$^1$ is selected from the group consisting of:
a bond;
C$_1$-C$_6$ alkylene, which is optionally substituted with 1-3 R$^a$;
—N(R$^{d1}$)—;
—N(R$^3$)—;
—O—;
S(O)$_p$, wherein p is 0, 1, or 2;
C(=O);
C(=S);
CHR$^2$;
—C(=O)CH(R$^2$)N(R$^{d1}$)—; and
—C(=O)CH(R$^2$)CH$_2$N(R$^{d1}$)—.

In certain embodiments, F$^1$ is selected from a bond, —N(R$^{d1}$)— (e.g., —N(H)—), —O—, and —S—.

In certain embodiments, F$^1$ is a bond.
In certain embodiments, F$^1$ is —N(R$^{d1}$)— (e.g., —N(H)—),
In certain embodiments, F$^1$ is —O—.
In certain embodiments, F$^1$ is —S—.

Variable G$^1$

In some embodiments of Formula (I-b), G$^1$ is selected from the group consisting of:
bond;
C$_1$-C$_6$ alkylene, which is optionally substituted with 1-3 R$^a$;
—N(R$^{d1}$)—
—N(R$^3$)—;
—O—;
S(O)$_p$, wherein p is 0, 1, or 2;
C(=O);
C(=S);
CHR$^2$;
—C(=O)CH(R$^2$)N(R$^{d1}$)—; and
—C(=O)CH(R$^2$)CH$_2$N(R$^{d1}$)—.

In certain embodiments, G$^1$ is selected from the group consisting of:
bond;
—O—;
S(O)$_p$, wherein p is 0, 1, or 2;
C(=O);
C(=S);
CHR$^2$;
—C(=O)CH(R$^2$)N(R$^{d1}$)—; and
—C(=O)CH(R$^2$)CH$_2$N(R$^{d1}$)—.

In certain embodiments, G$^1$ is a bond.
In certain embodiments, G$^1$ is S(O)$_p$, wherein p=1 or 2 (e.g., p=2).

Variable M$^1$

In some embodiments of Formula (I-b), M$^1$ is selected from the group consisting of:
a bond;
C$_1$-C$_6$ alkylene, which is optionally substituted with 1-3 R$^a$;
—N(R$^{d1}$)—;
—N(R$^3$)—;
—O—;
S(O)$_p$, wherein p is 0, 1, or 2;
C(=O);
C(=S);
CHR$^2$;
—C(=O)CH(R$^2$)N(R$^{d1}$)—; and
—C(=O)CH(R$^2$)CH$_2$N(R$^{d1}$)—.

In certain embodiments, $M^1$ is selected from the group consisting of:
bond;
—O—;
$S(O)_p$, wherein p is 0, 1, or 2;
C(=O);
C(=S);
$CHR^2$;
—C(=O)CH($R^2$)N($R^{d1}$)—; and
—C(=O)CH($R^2$)$CH_2$N($R^{d1}$)—.

In certain embodiments, $M^1$ is a bond.

Variable $L^1$

In some embodiments of Formula (I-b), $L^1$ is selected from the group consisting of:
a bond;
$C_1$-$C_6$ alkylene, which is optionally substituted with 1-3 $R^a$;
—N($R^{d1}$)—
—N($R^3$)—;
—O—;
$S(O)_p$, wherein p is 0, 1, or 2;
C(=O);
C(=S);
$CHR^2$;
—C(=O)CH($R^2$)N($R^{d1}$)—; and
—C(=O)CH($R^2$)$CH_2$N($R^{d1}$)—.

In certain embodiments, $L^1$ is selected from the group consisting of:
bond;
—O—;
$S(O)_p$, wherein p is 0, 1, or 2;
C(=O);
C(=S);
$CHR^2$;
—C(=O)CH($R^2$)N($R^{d1}$)—; and
—C(=O)CH($R^2$)$CH_2$N($R^{d1}$)—.

In certain embodiments, $L^1$ is a bond.

In certain embodiments, $L^1$ is —C(=O)CH($R^2$)($CH_2$)N($R^{d1}$)— (e.g., $R^2$=H).

In certain embodiments, $L^1$ is C(=O).

In certain embodiments, $L^1$ is —C(=O)CH($R^2$)N($R^{d1}$)—.

Variables $R^2$ and $R^3$

In some embodiments of Formula (I-b), $R^2$ is H.

In some embodiments of Formula (I-b), $R^2$ is $C_1$-$C_6$ alkyl, which is optionally substituted with 1-3 $R^a$.

In certain embodiments, $R^2$ is $C_1$-$C_4$ alkyl, which is optionally substituted with 1-2 $R^a$ (e.g., $C_1$-$C_4$ alkyl substituted with 1 $R^a$).

In certain embodiments of foregoing (when $R^2$ is $C_1$-$C_4$ alkyl, which is optionally substituted with 1-2 $R^a$ (e.g., $C_1$-$C_4$ alkyl substituted with 1 $R^a$)), each $R^a$ is independently selected from: —OH; —SH; —NR$^e$R$^f$; —C(=O)O($C_{1-4}$ alkyl); —C(=O)OH; —CON(R')(R''); —S(O)$_{1-2}$(NR'R''); —S(O)$_{0-2}$($C_{1-4}$ alkyl); cyano; and —NR'C(=NR')NR'R''.

As non-limiting examples of the foregoing embodiments, each $R^a$ can be independently selected from: —$NH_2$, —OH, —SH, —SMe, —NH(C=NH)$NH_2$, $CO_2H$, and $CO_2NH_2$ (e.g., each $R^a$ can be independently selected from —$NH_2$, —OH, —NH(C=NH)$NH_2$, $CO_2H$, and $CO_2NH_2$).

In some embodiments of Formula (I-b), $R^2$ is $L^2$-$C_6$-$C_{10}$ aryl, which is optionally substituted with from 1-4 $R^e$; or
$L^2$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$.

In certain embodiments, $R^2$ is $L^2$-phenyl, wherein the phenyl is optionally substituted with 1-2 $R^c$.

In certain embodiments, $R^2$ is $L^2$-heteroaryl, wherein the heteroaryl includes from 5-8 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-2 independently selected $R^c$.

As non-limiting examples of the foregoing embodiments, $R^2$ can be $L^2$-indolyl or $L^2$-imidazolyl, wherein the indolyl or imidazolyl is optionally substituted with from 1-2 independently selected $R^c$.

In certain embodiments of the foregoing (when $R^2$ is $L^2$-$C_6$-$C_{10}$ aryl, which is optionally substituted with from 1-4 $R^c$ or $L^2$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$), each $R^c$ is independently selected from —OH; —SH; —F; —Cl; —Br; —NR$^e$R$^f$; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)OH; —CON(R')(R''); —S(O)$_{1-2}$(NR'R''); —S(O)$_{0-2}$($C_{1-4}$ alkyl); cyano; — and $C_{3-6}$ cycloalkyl optionally substituted with from 1-4 independently selected $C_{1-4}$ alkyl.

As non-limiting examples of the foregoing embodiments, each $R^c$ can be independently selected from —OH, F, —NR$^e$R$^f$, $C_{1-4}$ alkyl; and $C_{1-4}$ haloalkyl (e.g., $R^c$ is OH).

In certain embodiments, $L^2$ is a $C_{1-6}$ (e.g., $C_{1-4}$) alkylene optionally substituted with 1-3 $R^a$ (e.g., unsubstituted).

In some embodiments of Formula (I-b), each occurrence of $R^2$ independently is selected from:
H;
$C_1$-$C_6$ alkyl optionally substituted with 1-2 substituents selected from —$NH_2$, —OH, —SH, —SMe, —NH(C=NH)$NH_2$, $CO_2H$, and $CO_2NH_2$;
($C_1$-$C_6$ alkylene)-phenyl, optionally substituted with 1-2 —OH;
($C_1$-$C_6$ alkylene)-indolyl; and
($C_1$-$C_6$ alkylene)-imidazolyl; or
$R^2$ and $R^{d1}$, in the —CH($R^2$)N($R^{d1}$)— group, combine to form a pyrrolidine ring.

In certain embodiments, each occurrence of $R^2$ is independently selected from:
H;
$C_1$-$C_6$ alkyl optionally substituted with 1-2 substituents selected from —$NH_2$, —OH, —NH(C=NH)$NH_2$, $CO_2H$, and $CO_2NH_2$; and
($C_1$-$C_6$ alkylene)-imidazolyl.

As non-limiting examples of the foregoing embodiments, each occurrence of $R^2$ can be independently selected from:
H;

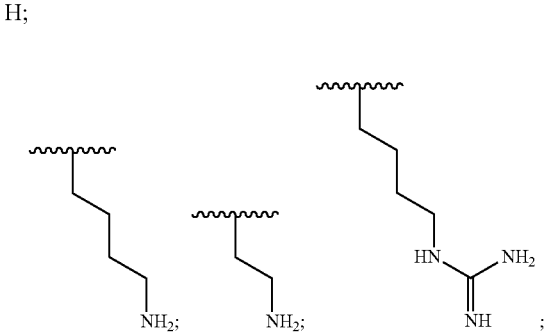

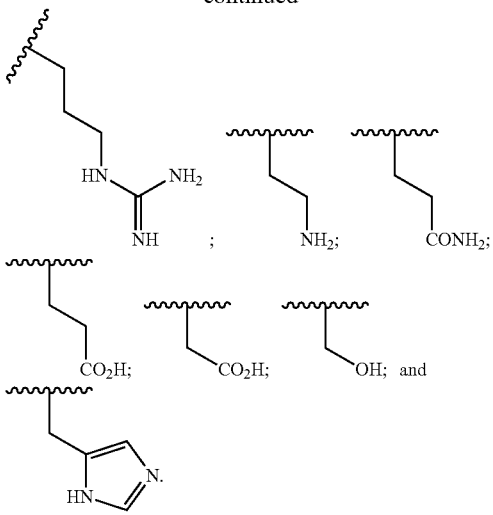

In some embodiments of Formula (I-b), each occurrence of $R^3$ is independently selected from:
- $C_1$-$C_6$ alkyl optionally substituted with 1-2 substituents selected from —$NH_2$, —OH, —SH, —SMe, —NH(C=NH)$NH_2$, $CO_2H$, and $CO_2NH_2$;
- ($C_1$-$C_6$ alkylene)-phenyl, optionally substituted with 1-2 —OH;
- ($C_1$-$C_6$ alkylene)-indolyl; and
- ($C_1$-$C_6$ alkylene)-imidazolyl.

In some embodiments of Formula (I-b), $R^3$ is $C_1$-$C_6$ alkyl, which is optionally substituted with 1-3 $R^a$.

In certain embodiments, $R^3$ is $C_1$-$C_4$ alkyl, which is optionally substituted with 1-2 $R^a$ (e.g., $C_1$-$C_4$ alkyl substituted with 1 $R^a$).

In certain embodiments of foregoing (when $R^3$ is $C_1$-$C_4$ alkyl, which is optionally substituted with 1-2 $R^a$ (e.g., $C_1$-$C_4$ alkyl substituted with 1 $R^a$)), each $R^a$ is independently selected from: —OH; —SH; —$NR^eR^f$; —C(=O)O($C_{1-4}$ alkyl); —C(=O)OH; —CON(R')(R''); —S(O)$_{1-2}$(NR'R''); —S(O)$_{0-2}$($C_{1-4}$ alkyl); cyano; and —NR'C(=NR')NR'R''.

As non-limiting examples of the foregoing embodiments, each $R^a$ can be independently selected from: —$NH_2$, —OH, —SH, —SMe, —NH(C=NH)$NH_2$, $CO_2H$, and $CO_2NH_2$ (e.g., each $R^a$ can be independently selected from —$NH_2$, —OH, —NH(C=NH)$NH_2$, $CO_2H$, and $CO_2NH_2$; e.g., each $R^a$ can be independently selected from —$NH_2$ and $CO_2H$).

In some embodiments of Formula (I-b), $R^3$ is $L^3$-$C_6$-$C_{10}$ aryl, which is optionally substituted with from 1-4 $R^e$; or $L^3$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$.

In certain embodiments, $R^3$ is $L^3$-phenyl, wherein the phenyl is optionally substituted with 1-2 $R^c$.

In certain embodiments, $R^3$ is $L^3$-heteroaryl, wherein the heteroaryl includes from 5-8 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-2 independently selected $R^c$.

As non-limiting examples of the foregoing embodiments, $R^3$ can be $L^3$-indolyl or $L^3$-imidazolyl, wherein the indolyl or imidazolyl is optionally substituted with from 1-2 independently selected $R^c$.

In certain embodiments of the foregoing (when $R^3$ is $L^2$-$C_6$-$C_{10}$ aryl, which is optionally substituted with from 1-4 $R^c$ or $L^3$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$), each $R^c$ is independently selected from —OH; —SH; —F; —Cl; —Br; —$NR^eR^f$; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)OH; —CON(R')(R''); —S(O)$_{1-2}$(NR'R''); —S(O)$_{0-2}$($C_{1-4}$ alkyl); cyano; — and $C_{3-6}$ cycloalkyl optionally substituted with from 1-4 independently selected $C_{1-4}$ alkyl.

As non-limiting examples of the foregoing embodiments, each $R^c$ can be independently selected from —OH, F, —$NR^eR^f$, $C_{1-4}$ alkyl; and $C_{1-4}$ haloalkyl (e.g., $R^c$ is OH).

In certain embodiments, $L^3$ is a $C_{1-6}$ (e.g., $C_{1-4}$) optionally substituted with 1-3 $R^a$ (e.g., unsubstituted).

In certain embodiments, $L^3$ is a $C_{1-6}$ (e.g., $C_{1-4}$) alkylene substituted with one oxo. As a non-limiting example of the foregoing, $L^3$ can be

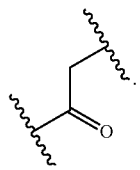 [SMILES: *CC(*)=O]

In certain embodiments, $L^3$ is a bond.

In certain embodiments, each occurrence of $R^3$ is independently selected from:
- $C_1$-$C_6$ alkyl optionally substituted with 1-2 substituents selected from —$NH_2$, —OH, —NH(C=NH)$NH_2$, $CO_2H$, and $CO_2NH_2$; and
- ($C_1$-$C_6$ alkylene)-imidazolyl.

As non-limiting examples of the foregoing embodiments, each occurrence of $R^3$ can be independently selected from:

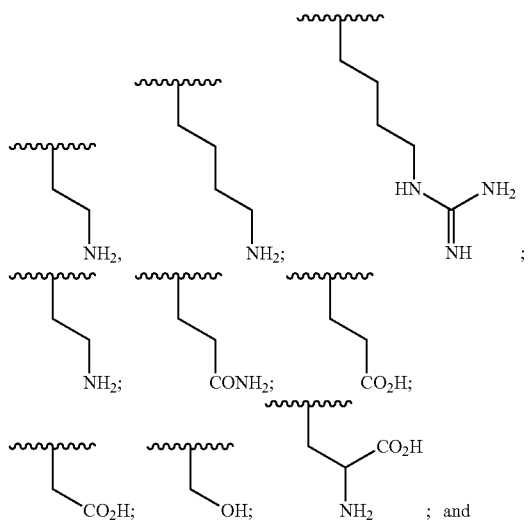

-continued

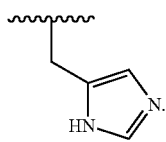

In certain embodiments, each occurrence of $R^3$ is independently selected from: $C_1$-$C_6$ alkyl optionally substituted with 1-2 substituents selected from —$NH_2$, —OH, —NH(C=NH)$NH_2$, $CO_2H$, and $CO_2NH_2$.

As non-limiting examples of the foregoing embodiments, each occurrence of $R^3$ can be independently selected from:

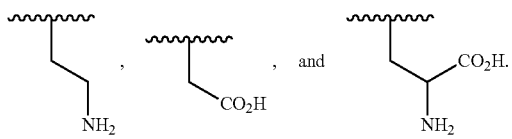

In some embodiments, each occurrence of $R^3$ is independently selected from: $L^3$-heterocyclyl, wherein the heterocyclyl includes from 3-10 ring atoms, wherein from 1-3 ring atoms are heteroatoms, each independently selected from the group consisting of $N(R^d)$, O, and S, and wherein one or more of the heterocyclyl ring carbon atoms are optionally substituted with from 1-4 independently selected $R^b$.

In certain embodiments, each occurrence of $R^3$ is independently selected from: $L^3$-heterocyclyl, wherein the heterocyclyl includes from 4-6 (e.g., 5-6) ring atoms, wherein from 1-3 ring atoms are heteroatoms, each independently selected from the group consisting of $N(R^d)$, O, and S, and wherein one or more of the heterocyclyl ring carbon atoms are optionally substituted with from 1-2 independently selected $R^b$ (e.g., heterocyclyl can be pyrrolidinyl, piperidinyl, or morpholinyl).

In certain embodiments (when each occurrence of $R^3$ is independently selected from: $L^3$-heterocyclyl, wherein the heterocyclyl includes from 3-10 ring atoms, wherein from 1-3 ring atoms are heteroatoms, each independently selected from the group consisting of $N(R^d)$, O, and S, and wherein one or more of the heterocyclyl ring carbon atoms are optionally substituted with from 1-4 independently selected $R^b$), $L^3$ is $C_{1-6}$ alkyl optionally substituted with from 1-3 independently selected $R^a$ (e.g., unsubstituted).

In certain embodiments (when each occurrence of $R^3$ is independently selected from: $L^3$-heterocyclyl, wherein the heterocyclyl includes from 3-10 ring atoms, wherein from 1-3 ring atoms are heteroatoms, each independently selected from the group consisting of $N(R^d)$, O, and S, and wherein one or more of the heterocyclyl ring carbon atoms are optionally substituted with from 1-4 independently selected $R^b$), $L^3$ is a $C_{1-6}$ (e.g., $C_{1-4}$) alkylene substituted with one oxo (e.g., can be

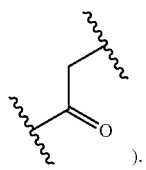).

As non-limiting examples, $R^3$ can be selected from:

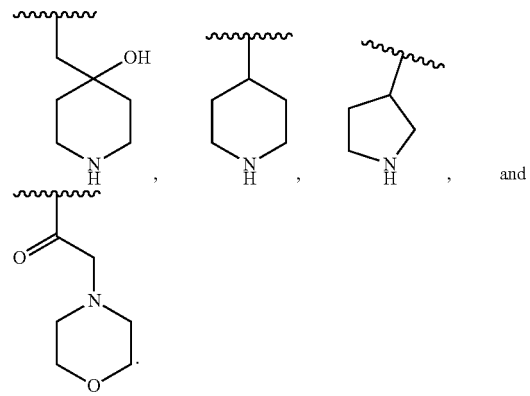

and

Variable $R^{d1}$

In some embodiments of Formula (I-b), each occurrence of $R^{d1}$ is independently selected from the group consisting of: each occurrence of $R^{d1}$ is selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); and —S(O)$_{1-2}$($C_{1-4}$ alkyl); or $R^2$ and $R^{d1}$, in the —C(=O)CH($R^2$) N($R^{d1}$)— group, combine to form a ring including from 5-8 ring atoms as defined above.

In certain embodiments, each occurrence of $R^{d1}$ is independently selected from the group consisting of: H, $C_{1-6}$ alkyl; and $C_{3-6}$ cycloalkyl.

In certain embodiments, each occurrence of $R^{d1}$ is H.

Variables $B^1$ and $B^2$

In some embodiments of Formula (I-b), each of $B^1$ and $B^2$ is independently —$Z^1$—$Z^3$ (i.e., $Z^2$ is a bond).

In some embodiments of Formula (I-b), $Z^3$ is H, halo, or $C_{1-3}$ alkyl.

In some embodiments of Formula (I-b), $Z^3$ is H or $C_{1-3}$ alkyl (e.g., $Z^3$ can be H).

In some embodiments of Formula (I-b), $Z^3$ is halo (e.g., $Z^3$ can be F).

In some embodiments of Formula (I-b), $Z^1$ is $C_{1-3}$ alkylene which is optionally substituted with 1-3 independently selected $R^a$ (e.g., $Z^1$ can be methylene, CHF, or $CF_2$).

In certain embodiments, $Z^1$ is unsubstituted $C_{1-3}$ alkylene (e.g., $CH_2$).

In certain embodiments, $Z^1$ is unsubstituted $C_{1-3}$ alkylene; and $Z^3$ is H.

In certain embodiments, $Z^1$ is $C_{1-3}$ alkylene substituted with from 1-2 independently selected halo (e.g., F).

In certain embodiments, each of $B^1$ and $B^2$ is independently selected from $CH_3$, $CHR^a$, $CH(R^a)_2$, and $C(R^a)_2$-halo.

As non-limiting examples of the foregoing embodiments, each of $B^1$ and $B^2$ can be independently $CH_3$, $CHF_2$, $CH_2F$, or $CF_3$.

Non-Limiting Combinations of Formula (I-b)

1

In some embodiments of Formula (I-b), one of $H^1$ or $J^1$ is —C(=O)CH($R^2$)N($R^{d1}$)—; and each of $E^1$ and $Q^1$ is an independently selected $C_1$-$C_6$ alkylene, which is optionally substituted with 1-3 $R^a$ (e.g., $C_{2-4}$ alkylene, e.g., unsubstituted $C_{2-4}$ alkylene).

In certain embodiments of the foregoing, $F^1$ is —N($R^{d1}$)— (e.g., —N(H)—), —O—, or —S—).

In certain embodiments of [1], a compound of Formula (I-b) is a compound Formula (II):

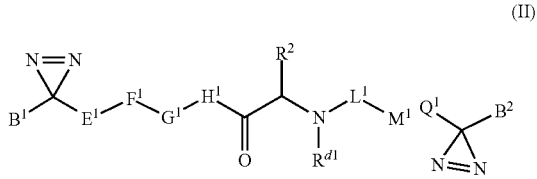
(II)

or a pharmaceutically acceptable salt thereof,
wherein:
each of $E^1$ and $Q^1$ is an independently selected $C_1$-$C_6$ alkylene (e.g., $C_{2-4}$ alkylene, e.g., unsubstituted $C_{2-4}$ alkylene), which is optionally substituted with 1-3 $R^a$;
$F^1$ is —$N(R^{d1})$— (e.g., —$N(H)$—), —O—, or —S—; and
each of $H^1$, $G^1$, $L^1$, and $M^1$ is independently selected from:
a bond;
—$N(R^{d1})$—,
—O—;
$S(O)_p$, wherein p is 0, 1, or 2;
$C(=O)$;
$C(=S)$;
$CHR^2$;
—$C(=O)CH(R^2)N(R^{d1})$—; and
—$C(=O)CH(R^2)CH_2N(R^{d1})$—.

1-1

In some embodiments of Formula (II), each of $L^1$ and $M^1$ is a bond.

In some embodiments of Formula (II), each of $G^1$ and $H^1$ is a bond.

In some embodiments of Formula (II), $F^1$ is —$N(R^d)$— (e.g., NH).

In certain embodiments, the compound of Formula II is a compound of Formula (II-a).

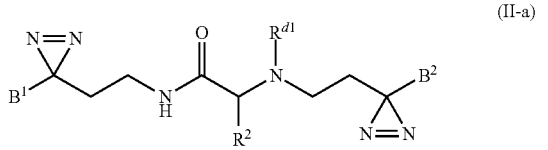
(II-a)

or a pharmaceutically acceptable salt thereof.

1-2

In some embodiments of Formula (II), $G^1$ is $S(O)_p$; and p is 1 or 2.

In certain embodiments of the foregoing (when $G^1$ is $S(O)_p$; and p is 1 or 2 in Formula II), $F^1$ is —O—.

In certain embodiments (when $G^1$ is $S(O)_p$; p is 1 or 2 in Formula II; and/or $F^1$ is —O—. O—), $H^1$ is —$N(R^{d1})$— (e.g., NH).

In certain embodiments, the compound of Formula (II) is a compound of Formula (II-b):

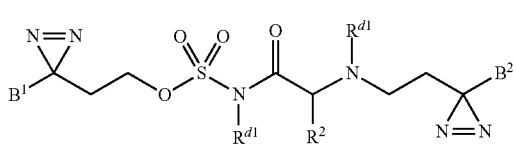
(II-b)

or a pharmaceutically acceptable salt thereof.

1-3

In some embodiments of Formula (II), $L^1$ is —$C(=O)CH(R^2)(CH_2)N(R^{d1})$—.

In certain embodiments of the foregoing (when $L^1$ is —$C(=O)CH(R^2)(CH_2)N(R^{d1})$— in Formula (II)), each of $M^1$, $G^1$ and $H^1$ is a bond.

In certain embodiments of the foregoing (when $L^1$ is —$C(=O)CH(R^2)(CH_2)N(R^{d1})$— in Formula II; and/or each of $M^1$, $G^1$ and $H^1$ is a bond in Formula (II)), $F^1$ is —O— or —$N(R^{d1})$— (e.g., —$N(H)$—).

In certain embodiments, the compound of Formula (II) is a compound of Formula (II-c1) or (II-c2):

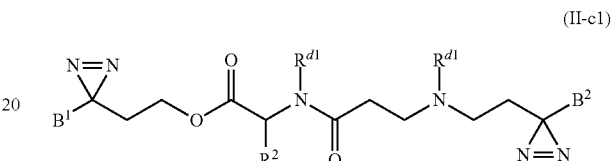
(II-c1)

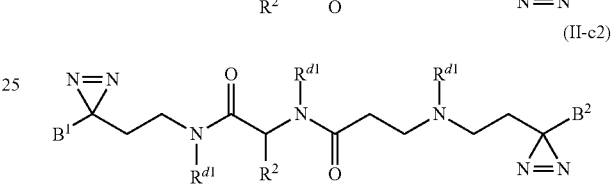
(II-c2)

or a pharmaceutically acceptable salt thereof.

1-4

In some embodiments of Formula (II), $L^1$ is $C(=O)$.

In certain embodiments of the foregoing (when $L^1$ is $C(=O)$ in Formula (II)), each of $M^1$, $G^1$ and $H^1$ is a bond.

In certain embodiments of the foregoing (when $L^1$ is $C(=O)$ in Formula (II); and/or each of $M^1$, $G^1$ and $H^1$ is a bond in Formula (II)), $F^1$ is —O— or —$N(R^{d1})$—.

In certain embodiments, the compound of Formula (II) is a compound of Formula (II-d):

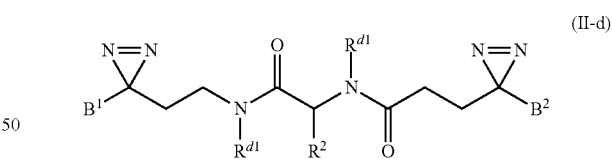
(II-d)

or a pharmaceutically acceptable salt thereof.

1-5

In some embodiments of Formula (II), $L^1$ is —$C(=O)CH(R^2)N(R^{d1})$—.

In certain embodiments of the foregoing, each of $M^1$, $G^1$ and $H^1$ is a bond.

In certain embodiments (e.g., when $L^1$ is —$C(=O)CH(R^2)N(R^{d1})$— and/or each of $M^1$, $G^1$ and $H^1$ is a bond), $F^1$ is is —O— or —$N(R^{d1})$— (e.g., —$N(H)$—).

In embodiments, the compound of Formula (II) is of Formula (II-e):

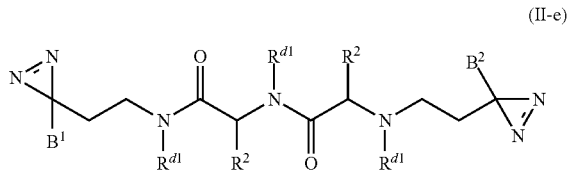

(II-e)

or a pharmaceutically acceptable salt thereof.

As a non-limiting example of the foregoing embodiments, the compound has the following formula:

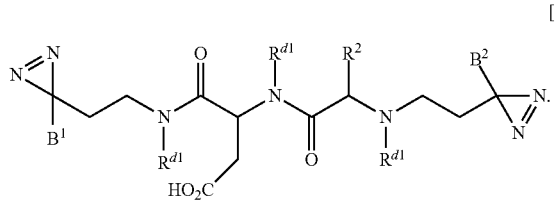

[2]

In some embodiments of Formula (I-b), one of $H^1$ and $J^1$ is —N($R^3$)— or —N($R^{d1}$)— (e.g., one of $H^1$ and $J^1$ is —N($R^3$)).

In certain embodiments of the foregoing, a compound of Formula (I-b) is a compound of Formula (III):

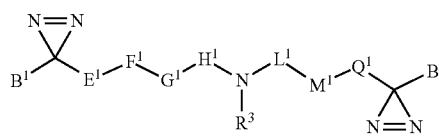

(III)

or a pharmaceutically acceptable salt thereof.

In certain embodiments of Formula (III), each of $E^1$ and $Q^1$ is an independently selected $C_1$-$C_6$ alkylene (e.g., $C_2$-$C_4$ alkylene, $C_2$-$C_3$ alkylene, $C_2$ alkylene, e.g. unsubstituted $C_2$ alkylene), which is optionally substituted with 1-3 $R^a$.

In certain embodiments of the foregoing, each of $F^1$ and $M^1$ is a bond.

In certain embodiments, each of $G^1$ and $L^1$ is independently selected from:
bond;
—O—;
S(O)$_p$, wherein p is 0, 1, or 2;
C(=O);
C(=S);
CHR$^2$;
—C(=O)CH($R^2$)N($R^{d1}$)—; and
—C(=O)CH($R^2$)CH$_2$N($R^{d1}$)—.

As non-limiting examples of the foregoing embodiments, each of $G^1$ and $L^1$ is a bond.

In certain embodiments of the foregoing of [2], $H^1$ is a bond.

In certain embodiments of the foregoing of [2], $H^1$ is (C=O).

In certain embodiments of [1] (including [1-1]-[1-4]) and [2], each occurrence of $R^2$ is as defined in claims 40-42.

In certain embodiments of [1] (including [1-1]-[1-4]) and [2], each occurrence of $R^2$ independently is selected from:
H;
$C_1$-$C_6$ alkyl optionally substituted with 1-2 substituents selected from —NH$_2$, —OH, —SH, —SMe, —NH(C=NH)NH$_2$, CO$_2$H, and CO$_2$NH$_2$;
($C_1$-$C_6$ alkylene)-phenyl, optionally substituted with 1-2 —OH;
($C_1$-$C_6$ alkylene)-indolyl; and
($C_1$-$C_6$ alkylene)-imidazolyl; or
$R^2$ and $R^{d1}$, in the —CH($R^2$)N($R^{d1}$)— group, combine to form a pyrrolidine ring.

In certain embodiments of [1] (including [1-1]-[1-4]) and [2], each occurrence of $R^2$ is independently selected from:
H;
$C_1$-$C_6$ alkyl optionally substituted with 1-2 substituents selected from —NH$_2$, —OH, —NH(C=NH)NH$_2$, CO$_2$H, and CO$_2$NH$_2$; and
($C_1$-$C_6$ alkylene)-imidazolyl.

In certain embodiments of [1] (including [1-1]-[1-4]) and [2], each occurrence of $R^2$ is independently selected from:
H;

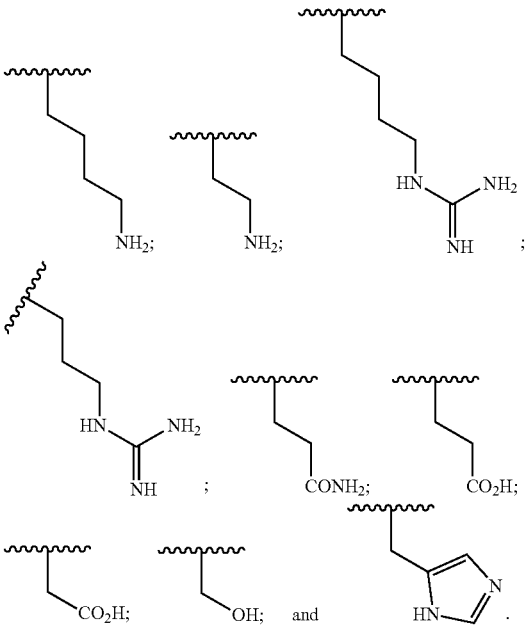

In certain embodiments of [1] (including [1-1]-[1-4]) and [2], each occurrence of $R^3$ is as defined in claims 43-45.

In certain embodiments of [1] (including [1-1]-[1-4]) and [2], each occurrence of $R^3$ is independently selected from:
$C_1$-$C_6$ alkyl optionally substituted with 1-2 substituents selected from —NH$_2$, —OH, —SH, —SMe, —NH(C=NH)NH$_2$, CO$_2$H, and CO$_2$NH$_2$;
($C_1$-$C_6$ alkylene)-phenyl, optionally substituted with 1-2 —OH;
($C_1$-$C_6$ alkylene)-indolyl; and
($C_1$-$C_6$ alkylene)-imidazolyl.

In certain embodiments of [1] (including [1-1]-[1-4]) and [2], each occurrence of $R^3$ is independently selected from:
$C_1$-$C_6$ alkyl optionally substituted with 1-2 substituents selected from —NH$_2$, —OH, —NH(C=NH)NH$_2$, CO$_2$H, and CO$_2$NH$_2$; and
($C_1$-$C_6$ alkylene)-imidazolyl.

In certain embodiments of [1] (including [1-1]-[1-4]) and [2], each occurrence of $R^3$ is independently selected from:

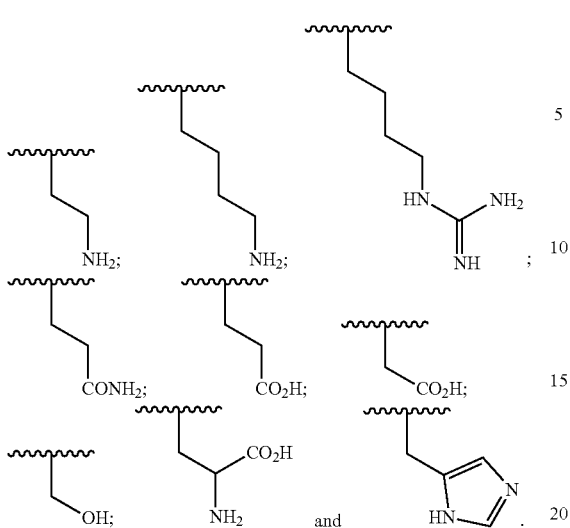

As a non-limiting example of the foregoing embodiments, each occurrence of $R^3$ can be independently selected from the group consisting of:

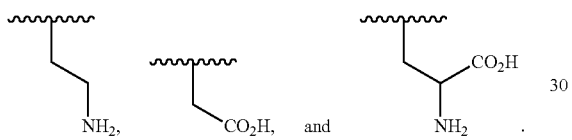

In certain embodiments of [1] (including [1-1]-[1-4]) and [2], each occurrence of $R^3$ is independently selected from: $L^3$-heterocyclyl, wherein the heterocyclyl includes from 3-10 ring atoms, wherein from 1-3 ring atoms are heteroatoms, each independently selected from the group consisting of $N(R^d)$, O, and S, and wherein one or more of the heterocyclyl ring carbon atoms are optionally substituted with from 1-4 independently selected $R^b$.

In certain embodiments of [1] (including [1-1]-[1-4]) and [2], each occurrence of $R^3$ is independently selected from: $L^3$-heterocyclyl, wherein the heterocyclyl includes from 4-6 (e.g., 5-6) ring atoms, wherein from 1-3 ring atoms are heteroatoms, each independently selected from the group consisting of $N(R^d)$, O, and S, and wherein one or more of the heterocyclyl ring carbon atoms are optionally substituted with from 1-2 independently selected $R^b$ (e.g., heterocyclyl can be pyrrolidinyl, piperidinyl, or morpholinyl).

In certain embodiments of [1] (including [1-1]-[1-4]) and [2] (when $R^3$ is: $L^3$-heterocyclyl), $L^3$ is a bond. In certain other embodiments, $L^3$ is $C_{1-6}$ alkyl optionally substituted with from 1-3 independently selected $R^a$ (e.g., unsubstituted). In certain embodiments of [1] (including [1-1]-[1-4]) and [2] (when $R^3$ is: $L^3$-heterocyclyl), $L^3$ is $C_{1-6}$ (e.g., $C_{1-4}$) alkylene substituted with one oxo (e.g., can be

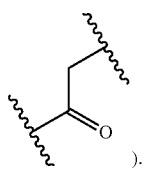).

In certain embodiments of [1] (including [1-1]-[1-4]) and [2] (when $R^3$ is: $L^3$-heterocyclyl), $R^3$ is selected from:

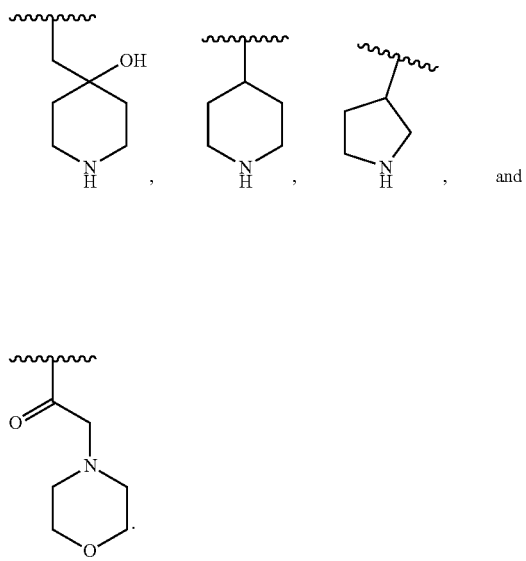

In certain embodiments of [1] (including [1-1]-[1-4]) and [2], each of $B^1$ and $B^2$ is as defined in claims 53-57.

In certain embodiments of [1] (including [1-1]-[1-4]) and [2], each of $B^1$ and $B^2$ is independently —$Z^1$—$Z^3$ (i.e., $Z^2$ is a bond).

In certain embodiments of [1] (including [1-1]-[1-4]) and [2], $Z^3$ is H, halo, or $C_{1-3}$ alkyl. In certain embodiments of [1] (including [1-1]-[1-4]) and [2], $Z^1$ is $C_{1-3}$ alkylene optionally substituted with from 1-3 independently selected $R^a$.

In certain embodiments of [1] (including [1-1]-[1-4]) and [2], each of $B^1$ and $B^2$ is independently selected from $CH_3$, $CHR^a$, $CH(R^a)_2$, and $C(R^a)_2$ halo.

In certain embodiments of [1] (including [1-1]-[1-4]) and [2], each of $B^1$ and $B^2$ is independently selected from $CH_3$, $CHF_2$, $CH_2F$, and $CF_3$.

In certain embodiments of [1] (including [1-1]-[1-4]) and [2], each occurrence of $R^{d1}$ is as defined in claims 58-60.

In certain embodiments of [1] (including [1-1]-[1-4]) and [2], each occurrence of $R^{d1}$ is independently selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R')(R''); —S(O)$_{1-2}$(NR'R''); and —S(O)$_{1-2}$($C_{1-4}$ alkyl); or $R^2$ and $R^{d1}$, in the —C(=O)CH($R^2$) N($R^{d1}$)— group, combine to form a ring including from 5-8 ring atoms as defined above.

In certain embodiments of [1] (including [1-1]-[1-4]) and [2], each occurrence of $R^{d1}$ is independently selected from the group consisting of: H, $C_{1-6}$ alkyl; and $C_{3-6}$ cycloalkyl. As a non-limiting example of the foregoing embodiments, each $R^{d1}$ can be H.

In some embodiments, the compound is selected from Table-A1, below:

TABLE A-1

| Example # | Compound | Name/ID # |
|---|---|---|
| 1 | | Compound 2 |
| 2 | | Compound 6 |
| 3 | | Compound 10 |
| 4 | | Compound 14 |
| 5 | | Compound 18 |
| 6 | | Compound 25 |
| 7 | | Compound 29 |

TABLE A-1-continued
| Example # | Compound | Name/ID # |
|---|---|---|
| 8 | 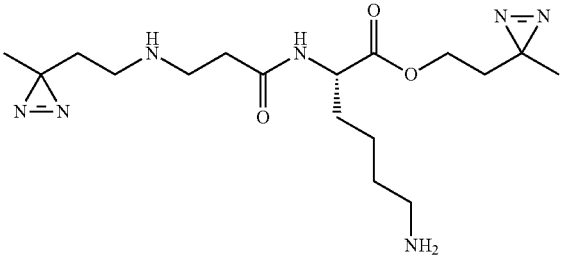 | Compound 33 |
| 9 | 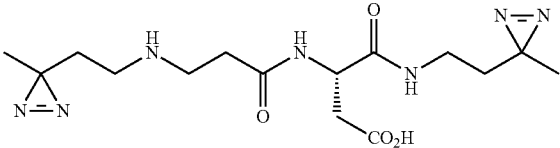 | Compound 37 |
| 10 | 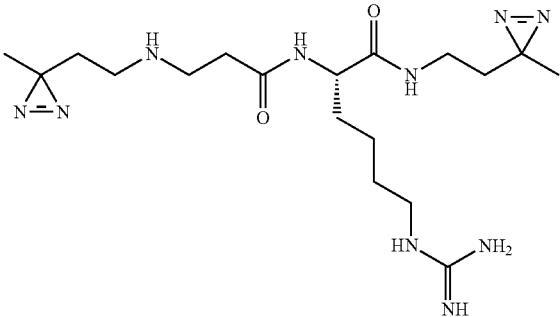 | Compound 43 |
| 11 | 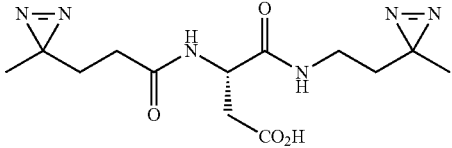 | Compound 45 |
| 12 | 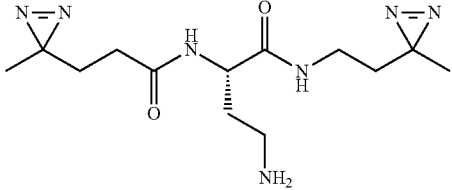 | Compound 49 |
| 13 | 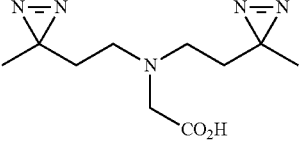 | Compound 52 |
| 14 | 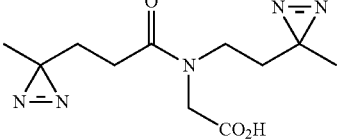 | Compound 54 |

TABLE A-1-continued

| Example # | Compound | Name/ID # |
|---|---|---|
| 15 | | Compound 57 |
| 16 | | Compound 60 |
| 17 | | Compound 64 |
| 18 | | Compound 68 |
| 19 | | Compound 73 |
| 20 | | Compound 75 |
| 21 | | Compound 78 |

TABLE A-1-continued

| Example # | Compound | Name/ID # |
|---|---|---|
| 22 | (structure) | Compound 81 |
| 23 | (structure) | Compound 84 | or a pharmaceutically acceptable salt thereof.

Pharmaceutical Compositions and Administration

General

In some embodiments, a chemical entity (e.g., a compound or a pharmaceutically acceptable salt and/or hydrate and/or prodrug of the compound) that generates cross-linking in the cornea in response to exposure to photoactivating light is administered as a pharmaceutical composition that includes the chemical entity and one or more pharmaceutically acceptable excipients, and optionally one or more additional therapeutic agents as described herein.

In some embodiments, the pharmaceutical composition is as described in U.S. 2018/0236077 which is incorporated herein by reference in its entirety.

In some embodiments, the chemical entities described herein can be administered in combination with one or more delivery agents. Delivery agents include, but are not limited to, anesthetic agents, analgesic agents, tonicity agents, shear-thinning, viscosity-increasing agents, surfactants (e.g., ionic surfactants or non-ionic surfactants), or chelating agents. Non-limiting examples of anesthetic agents may include pilocarpine, proparacaine, tetracaine, or oxybuprocaine. Non-limiting examples of analgesic agents include menthol, benzyl alcohol, or phenylethyl alcohol. Non-limiting examples of tonicity agents include glycerin, propylene glycol, polyethylene glycol (PEG)-8, ethanol, benzyl alcohol, phenylethyl alcohol, or triacetin. Non-limiting examples of shear-thinning, viscosity-increasing agents include carbomer, polycarbophil, gellan gum, xanthan gum, carboxymethyl cellulose sodium, or sodium hyaluronate. Non-limiting examples of ionic surfactants include benzalkonium chloride. Non-limiting examples of non-ionic surfactants include poloxamer 407, tetronic 1107, tetronic 1304, polysorbate 80, polyethylene glycol (PEG)-40 hydrogenated castor oil, lecithin, polysorbate 60, polyethylene glycol (PEG)-35 castor oil, tocophersolan (TPGS), nonoxynol-9, or tyloxapol. Non-limiting examples of chelating agents include ethylenediaminetetraacetic acid (EDTA) or citrate.

In some embodiments, the chemical entities described herein can be administered in combination with one or more preparatory formulations to an epithelium of a cornea. In certain embodiments, the preparatory formulations increase a permeability of the epithelium of the cornea. As non-limiting examples of the foregoing, preparatory formulations can include one or more of: zinc metalloproteinase, copper metalloproteinase, papain, bromelain, actinidin, ficain, N-acetylcysteine, ambroxol, carbocisteine, or erdosteine. In certain embodiments, the one or more preparatory formulations can further include one or more anesthetic agents (e.g., pilocarpine, proparacaine, tetracaine, or oxybuprocaine).

In some embodiments, the chemical entities described herein can be administered in combination with one or more enhancement formulations which are configured to one or more of: (i) remove the one or more therapeutic formulations from the epithelium of the cornea without diluting the one or more therapeutic agents delivered to the stroma; (ii) close tight junctions of the epithelium to control hydration of the cornea; (iii) promote oxidation for the one or more therapeutic agents delivered to the stroma; or (iv) further deliver the one or more therapeutic formulations from the epithelium to the stroma. As non-limiting examples of the foregoing, the enhancement formulations may include one or more of: divalent metal salts, one or more pro-oxidants, or one or more glycosaminoglycans.

In some embodiments, the chemical entities described herein can be administered in combination with one or more post-treatment formulations in response to applying the one or more enhancement formulations, and the one or more post-treatment formulations may include at least one of one or more divalent metal salts, one or more viscosity agents, one or more glycosaminoglycans, or one or more antibiotics.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, UK. 2012).

Routes of Administration and Composition Components

Compositions can be prepared as liquid solutions or suspensions; solid forms suitable for use to prepare solutions or suspensions upon the addition of a liquid prior to administration can also be prepared; and the preparations can also be emulsified. The preparation of such formulations will be known to those of skill in the art in light of the present disclosure.

Compositions can be administered topically (e.g., intraocularly as a topical instillation).

The pharmaceutical forms suitable for intraocular use include sterile aqueous solutions (e.g., buffers, e.g., citrate buffers; e.g., ophthalmic solutions, e.g., 20% dextran ophthalmic solution) or dispersions; formulations including sesame oil, peanut oil, or aqueous propylene glycol; and sterile powders for the extemporaneous preparation of sterile solutions or dispersions. In general, the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the compositions can be brought about by the use in the compositions of agents delaying absorption, for example, aluminum monostearate and gelatin.

Sterile solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile solutions, the preferred methods of preparation are vacuum-drying and freeze-drying techniques, which yield a powder of the active ingredient, plus any additional desired ingredient from a previously sterile-filtered solution thereof.

In certain embodiments the excipients are sterile and generally free of undesirable matter. These compositions can be sterilized by conventional, well-known sterilization techniques. For various oral dosage form excipients such as tablets and capsules, sterility is not required. The USP/NF standard is usually sufficient.

Ocular compositions can include, without limitation, one or more of any of the following: dextran, viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In certain embodiments, the compounds and compositions disclosed herein can be applied to a cornea of an eye using an applicator. Non-limiting examples of applicators can include eyedropper or syringe.

In certain embodiments, the compounds and compositions described herein can be administered in a formulation that allows the compound of composition to pass through the corneal epithelium to underlying regions in the corneal stroma. In other embodiments, the corneal epithelium may be removed or otherwise incised to allow the compound or compositions provided herein to be applied more directly to the underlying tissue.

Accordingly, in some embodiments the compounds and compositions described herein are directly applied to the cornea (e.g., without removing or otherwise incising corneal epithelium). In other embodiments, the corneal epithelium is be removed or otherwise incised before the compounds and compositions described herein are applied.

Dosages

The dosages may be varied depending on the requirement of the patient, the severity of the condition being treated and the particular compound being employed. Proper dosage for a particular situation can be determined by one skilled in the medical arts. In some cases, the total dosage may be divided and administered in portions throughout the procedure or by means providing continuous delivery.

In some embodiments, the composition is a solution (e.g., buffers, e.g., citrate buffers; e.g., ophthalmic solutions, e.g., 20% dextran ophthalmic solution) that comprises from 0.01-100 mg/mL of a chemical entity described herein (e.g., from 0.02-50 mg/mL, from 0.04-25 mg/mL, from 0.08-12.5 mg/mL, from 0.16-6.25 mg/mL, from 0.2-5 mg/mL). In certain embodiments of the foregoing, a unit dosage is from 0.001-1 mL (e.g., from 0.002-0.5 mL, from 0.010-0.25 mL, e.g., from 0.020-0.1 mL).

In some embodiments, the composition is a solution (e.g., buffers, e.g., citrate buffers; e.g., ophthalmic solutions, e.g., 20% dextran ophthalmic solution) that comprises from 0.001%-20% of a chemical entity described herein (e.g., from 0.002%-10%, from 0.004%-5%, from 0.008%-2.5%). In certain embodiments of the foregoing, a unit dosage is from 0.001-1 mL (e.g., from 0.002-0.5 mL, from 0.010-0.25 mL, e.g., from 0.020-0.2 mL).

Regimens

The foregoing dosages can be administered periodically for a specific duration of time. In some embodiments, a unit dosage can be administered every 1-1200 seconds (e.g., every 2-300 seconds, every 2-150 seconds, every 5-150 seconds, every 5-100 seconds, every 5-10 seconds, every 10-150 seconds, every 50-150 seconds). In certain embodiments of the foregoing, the dosages are administered over a period of from 1-1200 minutes (e.g., from 1-600 minutes, from 5-120 minutes, from 10-120 minutes).

Methods of Treatment

General

This disclosure features methods for treating a subject (e.g., a human) having a disease, disorder, or condition in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. In certain embodiments, the methods described herein can include or further include treating one or more conditions associated, co-morbid or sequela with any one or more of the conditions described herein.

In some embodiments, the method further comprises identifying the subject.

In certain embodiments, the chemical entities described herein provide refractive correction to the cornea (e.g., by imparting mechanical stiffness). In certain embodiments, the chemical entities described herein strengthen and stabilize the structure of the cornea.

In certain embodiments, the chemical entities described herein can be used for vision correction.

Method

In some embodiments, the method comprises administering a compound disclosed herein or a pharmaceutical composition thereof to a cornea of an eye in a subject in need thereof; and applying an electromagnetic radiation (e.g., a light) to the cornea, thereby generating cross-linking in the cornea.

In certain embodiments of the foregoing, the method comprises administering a compound disclosed herein or a pharmaceutical composition thereof to the stroma of the cornea of a subject in need thereof.

In certain embodiments, the compound disclosed herein or a pharmaceutical composition thereof is administered to the cornea without removing corneal epithelial cells.

In some embodiments, the claimed methods can be performed in the absence of added or supplemental oxygen levels, which can be advantageous in some applications.

In other embodiments, the method further comprises increasing or decreasing the concentration of $O_2$ at the cornea during irradiation.

In certain embodiments, the method further comprises administering to the cornea one or more delivery agents, wherein the one or more delivery agents are as described elsewhere herein.

In certain embodiments, the method further comprises administering to a subject in need thereof (e.g., the cornea of a subject in need thereof) one or more preparatory formulations that increases a permeability of the epithelium of the cornea, wherein the one or more preparatory formulations are as described elsewhere herein.

In certain embodiments, the method further comprises administering to the epithelium of the cornea one or more enhancement formulations, wherein the one or more enhancement formulations configured to one or more of:

(i) remove the one or more therapeutic formulations from the epithelium of the cornea without diluting the one or more therapeutic agents delivered to the stroma;

(ii) close tight junctions of the epithelium to control hydration of the cornea;

(iii) promote oxidation for the one or more therapeutic agents delivered to the stroma; or (iv) further deliver the one or more therapeutic formulations from the epithelium to the stroma, wherein the one or more enhancement formulations are as described elsewhere herein.

In certain embodiments, the method further comprises administering to the subject in need thereof one or more post-treatment formulations in response to applying one or more enhancement formulations, wherein the one or more enhancement formulations are as described elsewhere herein.

Electromagnetic Radiation

In some embodiments, the electromagnetic radiation applied to the cornea of an eye in a subject in need thereof is a light radiation. In certain embodiments, the light radiation has appropriate wavelength, energy, and duration, to cause a compound described herein to undergo a reaction (e.g., photoinduced electron transfer and/or fragmentation), thereby allowing cross-linking.

In some embodiments, wavelength of light can be chosen so that it corresponds to or encompasses the absorption of the compounds described herein, and reaches the area of the tissue that has been contacted with the compounds described herein, e.g., penetrates into the region where the compound described herein presents.

In some embodiments, the energy of the electromagnetic radiation applied is less than 2000 $J/cm^2$. In certain embodiments of the foregoing, the electromagnetic energy applied is between 1 and 500 $J/cm^2$. The total dose of energy absorbed in the cornea can be described as an effective dose, which is an amount of energy absorbed through an area of the corneal epithelium. For example the effective dose for a region of the corneal surface can be, for example, between 5 $J/cm^2$ and 20 $J/cm^2$ or 30 $J/cm^2$ (e.g., 5.4 $J/cm^2$).

In some embodiments, the electromagnetic radiation is applied at an irradiance of about 0.1-100 $mW/cm^2$ (e.g., 1-100 $mW/cm^2$). In certain embodiments, the electromagnetic radiation is applied at an irradiance of about 1-5 $mW/cm^2$ (e.g., 3 $mW/cm^2$).

In some embodiments, the electromagnetic radiation has wavelengths within the visible, infrared, or ultraviolet spectra. In some embodiments, the electromagnetic radiation includes radiations of wavelengths from about 300 nm to about 800 nm (e.g., from 300 nm to 700 nm). In certain embodiments, the electromagnetic radiation includes ultraviolet A (UVA) light (e.g., of wavelength between 350 and 380 nm e.g., 360-370 nm, e.g., 365 nm).

In certain embodiments, the electromagnetic radiation includes a visible wavelength (e.g., of wavelength between 400 nm and 550 nm, e.g., approximately 452 nm). In some embodiments, the electromagnetic radiation is laser radiation. In certain embodiments, the laser radiation is applied at an average power of 1-100 mW.

In some embodiments, the duration of radiation is between 30 seconds to 1 hour. In certain embodiments, the duration of irradiation is between 1 minute to 1 hr (e.g., 30 minutes).

In some embodiments, the cornea of an eye can be more broadly treated with a compound or composition described herein; and the radiation can be selectively directed to regions of the treated cornea according to a particular pattern.

In certain embodiments, the electromagnetic radiation may be directed and focused with one or more mirrors or lenses to a particular pattern on the cornea (e.g., at particular focal planes within the cornea, e.g., at particular depths in the underlying region wherein cross-linking activity is desired).

In some embodiments, specific regimes of electromagnetic radiation can be modulated to achieve a desired degree of cross-linking in the selected regions of the cornea. For example, electromagnetic radiation may be delivered according to any combination of: wavelength, bandwidth, intensity, power, location, depth of penetration, and/or duration of treatment (the duration of the exposure cycle, the dark cycle, and the ratio of the exposure cycle to the dark cycle duration).

In some embodiments, the electromagnetic irradiation is delivered using a system that comprises a digital micromirror device (DMD) to modulate the application of electromagnetic radiation spatially and temporally. In certain embodiments of the foregoing, light is projected in a precise spatial pattern that is created by microscopically small mirrors laid out in a matrix on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes as described above. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Additionally, pre-clinical patient information may be combined with finite element biomechanical computer modeling to create patient specific pre-treatment plans.

In some embodiments, the electromagnetic radiation is delivered using multiphoton excitation microscopy. In particular, rather than delivering a single photon of a particular wavelength to the cornea, multiple photons of longer wavelengths, i.e., lower energy, are delivered that combine to initiate the cross-linking. Advantageously, longer wavelengths are scattered within the cornea to a lesser degree than shorter wavelengths, which allows longer wavelengths of light to penetrate the cornea more efficiently than shorter wavelength light. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules of the compounds or compositions disclosed herein to generate the photochemical kinetic reactions described further below. When a compound disclosed herein simultaneously absorbs both photons, it absorbs enough energy to release reactive radicals in the corneal tissue. Embodiments may also utilize lower energy photons such that a molecule of a compound disclosed herein must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

In some embodiments, the electromagnetic radiation is applied continuously (continuous wave (CW)) or as pulsed radiation. In certain embodiments, this selection has an effect on the amount, the rate, and the extent of cross-linking. In certain embodiments, when the electromagnetic radiation light is applied as pulsed radiation, the duration of the exposure cycle, the dark cycle, and the ratio of the exposure cycle to the dark cycle duration have an effect on the resulting corneal stiffening. Pulsed radiation can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 0.1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

In some embodiments, pulsed radiation can be delivered by employing a DMD, electronically turning the light source 110 on and off, and/or using a mechanical or optoelectronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for example, may involve combinations of myopia, hyperopia, astigmatism, irregular astigmatism, presbyopia and complex corneal refractive surface corrections because of ophthalmic conditions such as keratoconus, pellucid marginal disease, post-lasik ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Examples of systems and methods for delivering electromagnetic radiation are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

Oxygen

In some embodiments, the claimed methods can be performed in the absence of added or supplemental oxygen levels, which can be advantageous in some applications. In other embodiments, the claimed methods can be performed in the presence of added or supplemental oxygen levels, As described herein, the claimed methods can further include administering one or more additional therapeutic agents (agents other than the compounds of formula I as described herein), in which the use of added or supplemental oxygen levels can be beneficial.

In some embodiments, the concentration of $O_2$ is increased or decreased (e.g., increased) actively during irradiation to control the rate of cross-linking. Oxygen may be applied during the cross-linking treatments in a number of different ways. In some embodiments, a pharmaceutical composition comprising compounds described herein can be supersaturated with $O_2$. Thus, when the compound described herein is applied to the eye, a higher concentration of $O_2$ is delivered directly into the cornea with the riboflavin and affects the reactions involving $O_2$ when the riboflavin is exposed to the electromagnetic radiation. According to another approach, a steady state of $O_2$ (at a selected concentration, e.g., >21%) may be maintained at the surface of the cornea to expose the cornea to a selected amount of $O_2$ and cause $O_2$ to enter the cornea. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference.

Accordingly, in some embodiments, the method may further include applying a selected concentration of oxygen to the eye, where the selected concentration is greater than a concentration of oxygen in atmosphere.

Indications

In some embodiments, the condition, disease or disorder is an ophthalmic disorder.

In some embodiments, the ophthalmic disorder involves reduced corneal rigidity.

Ectatic Disorder

In certain embodiments, the condition, disease or disorder is a corneal ectatic disorder. Non-limiting examples of ectatic disorders include keratoconus (e.g., keratoconus with nipple cones, oval cones, or globus cones; e.g., progressive keratoconus), keratoglobus, pellucid marginal degeneration, corneal ectasia (e.g., post-operative ectasia, e.g., post-LASIK ectasia), and Terrien's marginal degeneration.

In certain embodiments, the condition, disease or disorder is a corneal ectatic disorder developed following a refractive surgical procedure (e.g., post-operative corneal ectasis). Non-limiting examples of refractive surgical procedures include radial keratotomy (RK), photorefractive keratectomy (PRK), or laser in-situ keratomileusis (LASIK).

In certain embodiments, the condition, disease or disorder is bacterial keratitis.

Vision Conditions

In some embodiments, the disease, condition or disorder is myopia, hyperopia, astigmatism, irregular astigmatism, presbyopia.

In some embodiments, the ophthalmic disorder is cataract (e.g., nuclear, cortical, posterior, secondary, traumatic, or radiation cataract) or a lens disorder.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the compound described herein can be administered in combination with one or more of additional therapeutic agents. Representative additional therapeutic agents include, but are not limited to, therapeutic agents for inflammation, cataracts, lens disorder, or ectatic disorders, including but not limited to keratoconus (e.g., keratoconus with nipple cones, oval cones, or globus cones), keratoglobus, pellucid marginal degeneration, corneal ectasia (e.g., post-operative ectasia, e.g., post-LASIK ectasia), and Terrien's marginal degeneration.

In some embodiments, the one or more additional therapeutic agents include those useful, e.g., as cross-linking agents, including those described in U.S. Provisional Patent Application, filed on even date herewith, entitled Compounds and Compositions for Eye Treatment, and assigned 62/775,305.

In some embodiments, the one or more additional therapeutic agents include those useful, e.g., as cross-linking agents, including those described in U.S. Patent Application Publication No. 2014/0343480, filed on May 19, 2014, which is incorporated in its entirety by reference herein. Non-limiting examples include:

riboflavin (e.g., riboflavin or riboflavin phosphate);
2,3-butandione;
folic acid;
quinoxalines (e.g., Olaquidox);
quinolines (e.g., chloroquinine, hydroxychloroquinine, and quinine);
dibucaine;
methotrexate;
menadione; and
verteporfin and derivatives thereof.

Additional non-limiting examples of cross-linking agents can include photosensitizers such as Rose Bengal, methylene blue, and N-hydroxypyridine-2-(1H)-thione. Further non-limiting examples of cross-linking agents can also include photosensitizers such as Photofrin™, synthetic diporphyrins and dichlorins, phthalocyanines with or without metal substituents, chloroaluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series (e.g., protoporphyrin I through protoporphyrin IX, coproporphyrins, uroporphyrins, mesoporphyrins, hematoporphyrins and sapphyrins), chlorins, chlorine6, mono-1-aspartyl derivative of chlorine6, di-1-aspartyl derivative of chlorine6, tin (IV) chlorine6, meta-tetrahydroxphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, chlorophylis, bacteriochlorophyll A, anthracenediones, anthrapyrazoles, aminoanthraquinone, phenoxazine dyes, thiazines, methylene blue, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid, benzonaphthoporphyrazines, cationic imminium salts, tetracyclines, lutetium texaphyrin, texaphyrin, tin-etio-purpurin, porphycenes, benzophenothiazinium, xanthenes, rose bengal, eosin, erythrosin, cyanines, merocyanine 540, selenium substitued cyanines, flavins, riboflavin, proflavin, quinones, anthraquinones, benzoquinones, naphthaldiimides, naphthalimides, victoria blue, toluidine blue, dianthroquinones (e.g., hypericin), fullerenes, rhodamines and photosensitive derivatives thereof.

In some embodiments, the one or more additional agents include metals (including elemental and ionic forms) (e.g., metal salts, e.g., divalent metal salts). Non-limiting examples include:

iron (e.g., iron (II), e.g., $FeSO_4$) (in certain embodiments, the iron additive may be dissolved in the citrate buffer);
copper;
manganese;
chromium;
vanadium;
aluminum;
cobalt;
mercury;
cadmium;
nickel; and
arsenic;
optionally in combination with hydrogen peroxide.

In some embodiments, the one or more additional therapeutic agents include those useful, e.g., as anesthetic agents. Non-limiting examples include: pilocarpine, proparacaine, tetracaine, or oxybuprocaine.

In some embodiments, the one or more additional therapeutic agents include those useful, e.g., as analgesic agents. Non-limiting examples include: menthol, benzyl alcohol, or phenylethyl alcohol.

In some embodiments, the one or more additional therapeutic agents include those useful, e.g., for increasing a permeability of the epithelium of the cornea. Non-limiting examples include: zinc metalloproteinase, copper metalloproteinase, papain, bromelain, actinidin, ficain, N-acetylcysteine, ambroxol, carbocisteine, or erdosteine.

In some embodiments, the one or more additional therapeutic agents include those useful, e.g., as therapeutics for cataract and/or lens disorders.

In some embodiments, the one or more additional therapeutic agents include those useful, e.g., as antibiotics.

In some embodiments, the one or more additional therapeutic agents include those useful, e.g., in gene therapy.

In some embodiments, the one or more additional therapeutic regimens include therapeutic regimens for inflammation, cataracts, lens disorder, or ectatic disorders, including but not limited to keratoconus (e.g., keratoconus with nipple cones, oval cones, or globus cones), keratoglobus, pellucid marginal degeneration, corneal ectasia (e.g., post-operative ectasia, e.g., post-LASIK ectasia), and Terrien's marginal degeneration.

In some embodiments, the one or more additional therapeutic regimens include therapeutic regimens for myopia, hyperopia, astigmatism, irregular astigmatism, and presbyopia.

In some embodiments, the one or more additional therapeutic regimens include ophthalmic surgical procedures. Non-limiting examples include:
corneal transplant surgery;
cataract surgery;
laser surgery;
keratoplasty (e.g., penetrating keratoplasty or lamellar keratoplasty);
refractive surgery (e.g., keratotomy (RK), photorefractive keratectomy (PRK), or laser in-situ keratomileusis (LASIK));
cornea reshaping; and
treatment of corneal laceration.

Additional non-limiting examples of the one or more additional therapeutic regiments include contact lens therapy, amniotic membrane therapy, LASIK therapy, and administration of antibiotics.

Compound Preparation and Biological Assays

As can be appreciated by the skilled artisan, methods of synthesizing the compounds of the formulae herein will be evident to those of ordinary skill in the art.

Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and R G M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In some embodiments, intermediates useful for preparing the compounds described herein can be prepared using the chemistries delineated in any one or more of the following schemes and non-limiting examples.

Compound Preparation

Abbreviations

| | |
|---|---|
| tBu | tert-butyl |
| DCM | dichloromethane |
| DIPEA | diisopropylethylamine |
| DMF | dimethylformamide |
| EDCI | N-(3-Dimethylaminopropyl)-N'-ethylcarbodiimide |
| EtOAc | ethyl acetate |
| Fmoc | fluorenylmethyloxycarbonyl |
| Gln | glutamine |
| Glu | glutamic acid |
| HATU | N-[(Dimethylamino)-1H-1,2,3-triazolo-[4,5-b]pyridin-1-ylmethylene]-N-methylmethanaminium hexafluorophosphate N-oxide |
| His | histidine |
| HOBT | hydroxybenzotriazole |
| HPLC | high performance liquid chromatography |
| MeCN | acetonitrile |
| NMR | nuclear magnetic resonance |
| PE | petroleum ether |
| Pbf | 2,2,4,6,7-Pentamethyldihydrobenzofuran-5-sulfonyl |
| PyBop | benzotriazol-1-yl-oxytripyrrolidinophosphonium |

-continued

| | |
|---|---|
| | hexafluorophosphate |
| Rt | retention time |
| Ser | serine |
| TEA | triethylamine |
| TFA | trifluoroacetic acid |
| THF | tetrahydrofuran |
| Tri | trityl |
| Ts (e.g., in TsCl or TsOH) | p-toluenesulfonyl |
| UV | ultraviolet |

Synthetic Examples

Synthesis of Intermediates I-1, I-2, I-3 and I-4

Intermediates I-1, I-2, I-3 and I-4 were synthesized according to the scheme below:

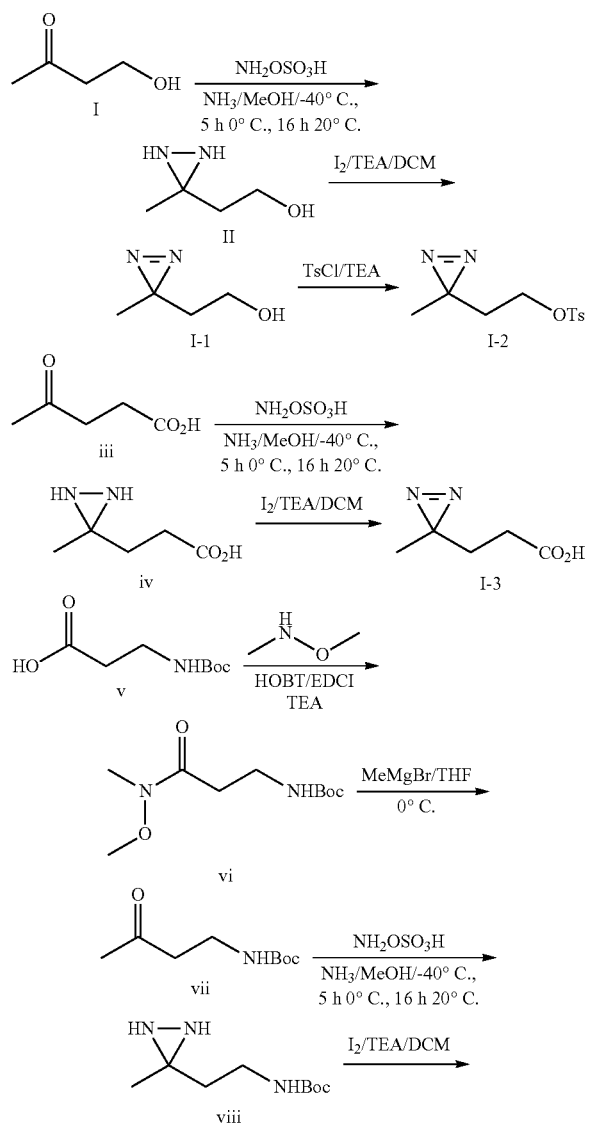

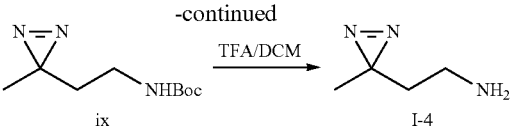

Compound ii

A solution of hydroxylamine-O-sulfonic acid (96.27 g, 851 mmol) in dry methanol (200 mL) was added dropwise to a stirred solution of 4-hydroxybutan-2-one (i) (50 g, 567 mmol) in 7M ammonia in methanol (500 mL) at −40° C. under a nitrogen atmosphere. The resulting mixture was stirred at 0° C. for at least 5 hours, then overnight at 20° C. The mixture was filtered through Celite™ and the solvent removed under reduced pressure to yield compound (ii) which was used directly in the next step without further purification.

ESI-MS m/z=103.2 [M+H]$^+$.

Intermediate I-1

Iodine (86.4 g, 340 mmol) was added slowly to compound (ii) (340 mmol) and triethylamine (94.73 mL, 680 mmol) in DCM (1 L) protected from light, until the appearance of a persistent orange-brown coloration. The resulting mixture was stirred at 20° C. for 2 hours. The mixture was subsequently washed with saturated brine and the solvent removed under reduced pressure. The residue was purified by silica gel chromatography, elution gradient 0 to 30% EtOAc in petroleum ether to afford Intermediate (I-1) (13 g) as a yellow liquid.

$^1$H NMR: (400 MHz, Chloroform-d) δ, ppm 3.55 (t, J=6.3 Hz, 2H), 1.65 (t, J=6.3 Hz, 2H), 1.51 (s, 1H), 1.09 (s, 3H).

Intermediate I-2

To a solution of intermediate (I-1) (3 g, 30 mmol) in DCM (30 mL) was added tosyl chloride (6.1 g, 36 mmol). The mixture was stirred at 0° C. and triethylamine (6.06 g, 60 mmol) was added dropwise. The mixture was warmed to room temperature and stirred for an additional 5 h protected from light. The mixture was subsequently washed with saturated brine, the organic layers concentrated and evaporated under reduced pressure. The residue was purified by silica gel chromatography to give intermediate (I-2) (5.9 g) as a colorless oil.

$^1$H NMR: (400 MHz, Chloroform-d) δ, ppm 7.89-7.76 (m, 2H), 7.46-7.34 (m, 2H), 3.97 (t, J=6.4 Hz, 2H), 2.47 (s, 3H), 1.69 (t, J=6.4 Hz, 2H), 1.02 (s, 3H).

Compound iv

A solution of hydroxylamine-O-sulfonic acid (43.83 g, 387.54 mmol) in dry methanol (200 mL) was added dropwise to a stirred solution of 4-oxopentanoic acid (iii) (30 g, 258.36 mmol) in 7M ammonia in methanol (400 mL) at −40° C. under a nitrogen atmosphere. The resulting mixture was stirred at 0° C. for at least 5 hours, then overnight at 20° C. The mixture was filtered through Celite™ and the solvent removed under reduced pressure to yield compound (iv) which was used directly in the next step without further purification.

ESI-MS m/z=131.1 [M+H]$^+$.

Intermediate I-3

To a protected from light 0° C. stirred solution of compound (iv) (40 g, 307.35 mmol) in DCM (400 mL) was added TEA (62.20 g, 614.69 mmol) and iodine (78.01 g, 307.35 mmol) in portions. The resulting mixture was stirred for 2 h at 20° C., washed with saturated brine (400 mL) and the solvent removed under reduced pressure. The residue was purified by silica gel column chromatography, elution gradient 20 to 40% EtOAc in petroleum ether to afford intermediate (I-3) (15.1 g) as a yellow oil.

Compound vi

To a stirred solution of 3-[[(tert-butoxy)carbonyl]amino]propanoic acid (v) (60 g, 317.11 mmol), N-methoxy-methylamine hydrochloride (37.12 g, 380.53 mmol) and TEA (80.22 g, 792.77 mmol) in DMF was added HOBT (47.13 g, 348.82 mmol) and EDCl (121.58 g, 634.21 mmol) in portions at 0° C. The mixture was stirred for 5 h at 20° C. before being diluted with water (2 L). The resulting mixture was extracted with EtOAc (3×800 mL). and the combined organic layers washed with water (3×800 mL), saturated brine (1 L), and dried over anhydrous $Na_2SO_4$. After filtration, the filtrate was concentrated under reduced pressure and the residue purified by silica chromatography, elution gradient 0 to 30% EtOAc in petroleum ether to afford compound (vi) (63.5 g) as a light yellow oil.

ESI-MS m/z=233.2 $[M+H]^+$.

Compound vii

Methylmagnesium bromide 1M in THF (328 mL, 328.07 mmol) was added dropwise to a 0° C. stirred solution of compound (vi) (63.5 g, 273.38 mmol) in THF (1 L) under an argon atmosphere. The mixture was stirred for 5 h at 0° C. before being quenched with aqueous $NH_4C_1$ (1 L) and extracted with EtOAc (3×800 mL). The combined organic layers were washed with water (3×1 L), saturated brine (1 L) and dried over anhydrous $Na_2SO_4$. After filtration, the filtrate was concentrated under reduced pressure. The residue was purified by silica gel column chromatography, elution gradient 0-15% EtOAc in petroleum ether to afford compound (vii) (24.8 g) as a colorless oil.

ESI-MS m/z=233.2 $[M+2Na]^+$.

$^1$HNMR: (400 MHz, DMSO-$d^6$) δ, ppm 1.37-1.42 (m, 10H), 2.08-2.09 (d, 3H), 2.50-2.57 (m, 2H), 3.08-3.13 (m, 2H), 6.75 (s, 1H).

Compound viii

A solution of hydroxylamine-O-sulfonic acid (29.96 g, 264.90 mmol) in dry methanol was added dropwise to a stirred solution of compound (vii) (24.8 g, 132.45 mmol) in 7M ammonia in methanol (300 mL) at −40° C. under a nitrogen atmosphere. The resulting mixture was stirred at 0° C. for at least 5 hours, then overnight at 20° C. The mixture was filtered through Celite™ and the solvent removed under reduced pressure to yield compound (viii) which was used directly in the next step without further purification.

ESI-MS m/z=202.3 $[M+H]^+$.

Compound ix

To a protected from light 0° C. stirred solution of compound (viii) (30 g, 149.05 mmol) in DCM (300 mL) was added TEA (30.17 g, 298.11 mmol) and iodine (37.83 g, 149.05 mmol) in portions. The resulting mixture was stirred for 2 h at 20° C., washed with saturated brine (300 mL), dried over anhydrous $Na_2SO_4$. After filtration, the filtrate was concentrated under reduced pressure and the residue purified by silica gel chromatography, elution gradient 0 to 30% EtOAc in petroleum ether to afford compound (ix) (13 g) as a yellow oil.

ESI-MS m/z=200.2 $[M+H]^+$ $^1$H NMR: (400 MHz, Chloroform-d) δ, ppm 1.05 (s, 3H), 1.45 (s, 9H), 1.58 (q, 2H), 3.05 (s, 2H), 4.60 (s, 1H).

Intermediate I-4

To a stirred 0° C. solution of compound (ix) (5 g, 25.09 mmol) in DCM (30 mL) was added TFA (15 mL). The mixture was stirred for 2 h at 20° C. before being concentrated under reduced pressure to give intermediate (I-4) trifluoroacetate salt which was used in the following procedures without any further purification.

ESI-MS m/z=197.3 $[M+H]^+$.

Synthesis of Compound 2 (Example 1)

Example 1 was synthesized according to the scheme below:

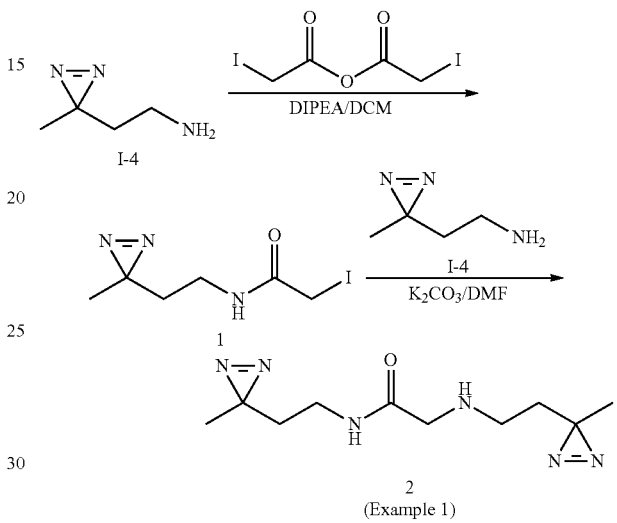

2
(Example 1)

Compound 1

To a solution of intermediate (I-4) obtained from compound (ix) (900 mg, 4.5 mmol) in in DCM (20 mL) was added 2-iodoacetic anhydride (354 mg, 6.75 mmol), and DIPEA (1.74 g, 13.5 mmol) in one portion. The mixture was stirred at room temperature for 3 h protected from light, quenched with saturated ammonium chloride and extracted with EtOAc. The combined organic layers were washed with saturated brine and dried over anhydrous sodium sulfate. The solvent was evaporated under reduced pressure to give compound (1) (1.38 g) as a yellow oil.

m/z (ES+), $[M+H]^+$=268.

Compound 2 (Example 1)

A mixture of compound (1) (1.38 g), intermediate (I-4) (5 mmol) and potassium carbonate (2.78 g) in DMF (20 mL) was stirred at room temperature for 5 h protected from light. The mixture was diluted with EtOAc (100 mL) and washed with saturated brine and water. The organic layer was dried over anhydrous sodium sulfate and concentrated under reduced pressure. The residue was purified by preparative HPLC Column: XBridge Shield RP18 OBD Column 19×250 mm, 10 µm; Mobile Phase A: 0.05% TFA in water, Mobile Phase B: MeCN; Flow rate: 25 mL/min; Gradient: 2% B to 17% B in 7 min; 254/220 nm; Rt: 3.81 min to give compound (2) (Example 1) (173.5 mg) as a yellow solid.

m/z (ES+), $[M+H]^+$=239

$^1$H NMR: (300 MHz, Methanol-d4) δ, ppm, 3.82 (t, J=2.3 Hz, 2H), 3.23 (t, J=7.3 Hz, 2H), 3.15-2.95 (m, 2H), 1.76 (td, J=8.4, 2.3 Hz, 2H), 1.69-1.50 (m, 2H), 1.15-0.97 (m, 6H).

Synthesis of Compound 6 (Example 2)

Example 2 was synthesized according to the scheme below:

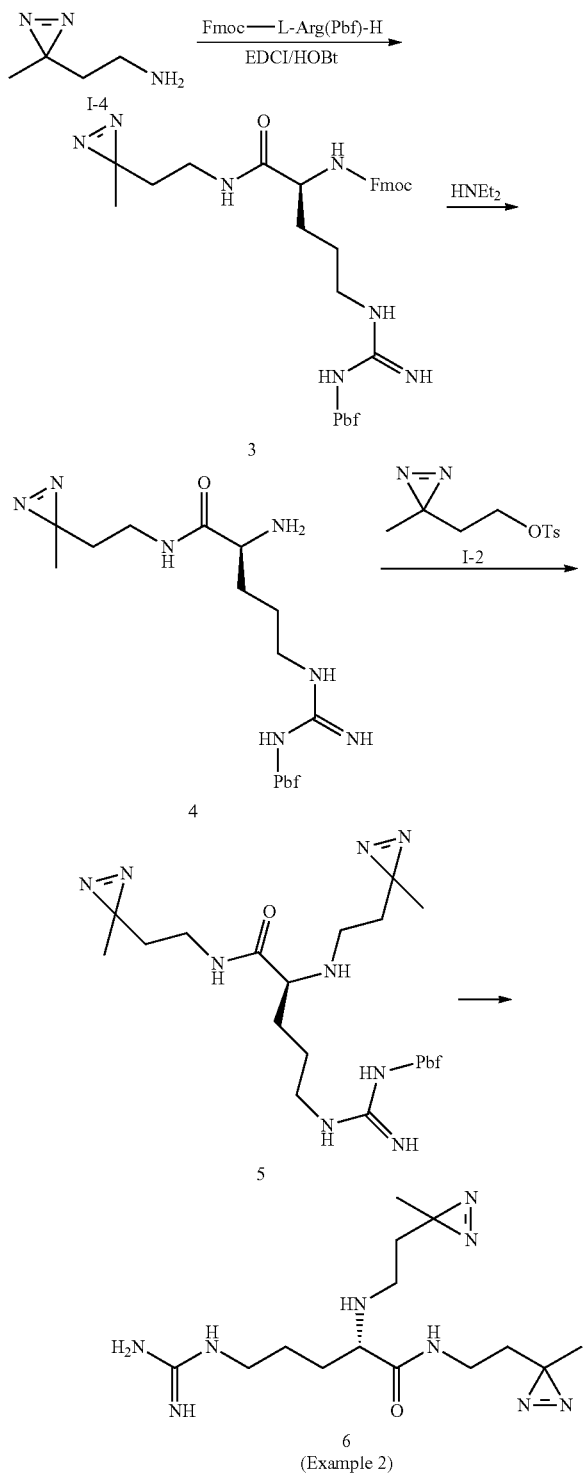

L-Arg(Pbf)-H (1.6 g, 2.5 mmol), HOBT (407 mg, 3 mmol) and EDCI (0.86 g, 5 mmol) in DMF (20 mL).

The mixture was stirred at room temperature for 3 h with the exclusion of light, then quenched with water and extracted with EtOAc. The organic layer was washed with saturated brine, dried over anhydrous sodium sulfate and concentrated under reduced pressure. The residue was purified using silica gel chromatography to give compound (3) (1.2 g) as a yellow oil.

m/z (ES+), [M+H]$^+$=730.

Compound 4

Compound (3) (1.2 g, 1.65 mmol) was added to 10% diethylamine in THF (15 mL) and stirred at room temperature for 2 h protected from light. The mixture was concentrated under reduced pressure to yield compound (4) which was used in the next step without further purification.

m/z (ES+), [M+H]$^+$=508.

Compound 5

A mixture of compound (4) obtained from compound (3) (1.2 g, 1.65 mmol), intermediate (I-2) (627.38 mg, 2.47 mmol) and potassium carbonate (458.7 mg, 3.3 mmol) in DMF (15 mL) was stirred at 55° C. for 10 h protected from light. The mixture was diluted with ethyl acetate (50 mL) and washed with saturated brine and water. The organic layer was dried over anhydrous sodium sulfate and concentrated under reduced pressure. The residue was purified using silica gel chromatography to give compound (5) (300 mg) as a yellow oil.

m/z (ES+), [M+H]$^+$=590.

Compound 6 (Example 2)

To a stirred solution of compound (5) (300 mg, 0.51 mmol) in DCM (10 mL) at 0° C. was added TFA (5 mL). The mixture was stirred at 0° C. for 2 h followed by room temperature for 2 h while protected from light. The mixture was concentrated under reduced pressure and the residue purified using preparative HPLC, column: Atlantis Prep T3 OBD Column 19×150 mm 5 μm; Mobile Phase A: Water (0.05% TFA), mobile Phase B: MeCN; Flow rate: 20 mL/min; Gradient: 14% B to 14% B in 10 min; 254/220 nm; Rt: 8.12 min gave compound (6) (Example 2) (40.8 mg) as colorless oil after freeze-drying.

m/z (ES+), [M+H]$^+$=339

$^1$H NMR: (300 MHz, Methanol-d4) δ, ppm, 3.80 (t, J=6.4 Hz, 1H), 3.25 (d, J=5.7 Hz, 5H), 2.99 (d, J=9.4 Hz, 2H), 1.94 (dd, J=10.6, 5.7 Hz, 2H), 1.68 (ddq, J=28.6, 15.3, 8.2, 6.3 Hz, 6H), 1.07 (d, J=1.1 Hz, 6H).

Synthesis of Compound 10 (Example 3)

Example 3 was synthesized according to the scheme below:

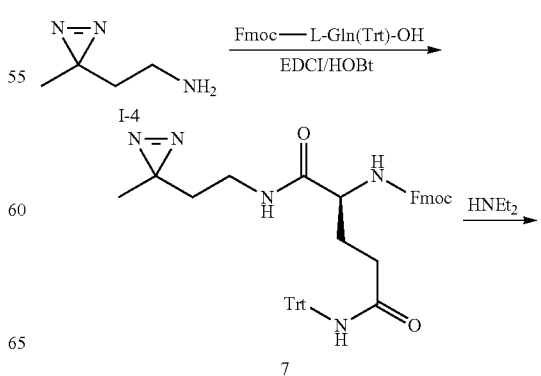

Compound 3

DIPEA (0.96 g, 7.5 mmol) was added dropwise to a stirred room temperature solution of intermediate (I-4) obtained from compound (ix) (500 mg, 2.5 mmol), Fmoc-

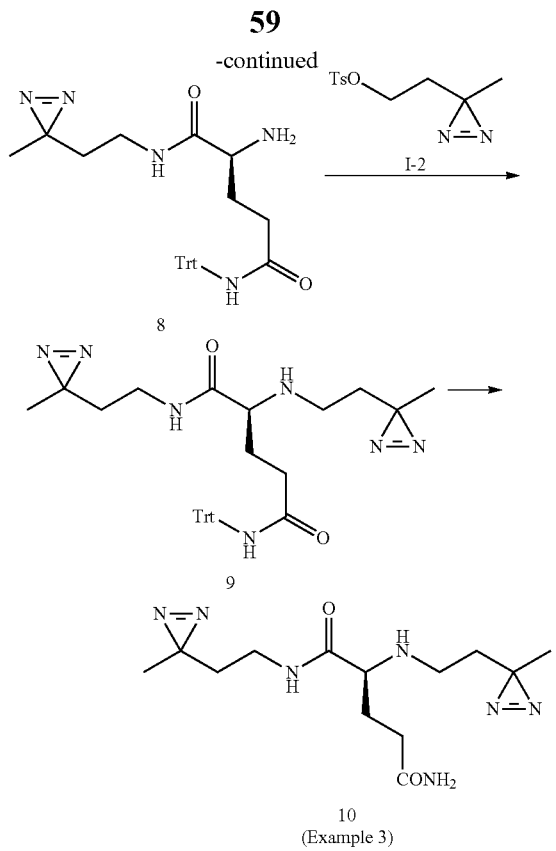

8

9

10
(Example 3)

Compound 7

DIPEA (0.96 g, 7.5 mmol) was added dropwise to a stirred room temperature solution of intermediate (I-4) obtained from compound (ix) (500 mg, 2.5 mmol), Fmoc-L-Gln(Trt)-OH (1.53 g, 2.5 mmol), HOBt (407 mg, 3 mmol) and EDCI (0.86 g, 5 mmol) in DMF (20 mL). The mixture was stirred at room temperature for 3 h with the exclusion of light, then quenched with water and extracted with EtOAc. The organic layer was washed with saturated brine, dried over anhydrous sodium sulfate and concentrated under reduced pressure. The residue was purified using silica gel chromatography to give compound (7) (1.37 g) as a yellow oil.

m/z (ES+), [M+H]$^+$=692.

Compound 8

Compound (7) (1.37 g, 2.92 mmol) was added to 10% diethylamine in THF (15 mL) and stirred at room temperature for 2 h protected from light. The mixture was concentrated under reduced pressure and the residue purified using silica gel chromatography to obtain compound (8) (680 mg) as a yellow solid.

m/z (ES+), [M+H]$^+$=470.

Compound 9

A mixture of compound (8) (680 mg, 1.45 mmol), intermediate (I-2) (551 mg, 2.17 mmol) and potassium carbonate (403.1 mg, 2.9 mmol) in DMF (15 mL) was stirred at 55° C. for 10 h protected from light. The mixture was diluted with ethyl acetate (50 mL) and washed with saturated brine and water. The organic layer was dried over anhydrous sodium sulfate and concentrated under reduced pressure to give compound (9) as a yellow oil which was used directly in the next step without further purification.

m/z (ES+), [M+H]$^+$=590.

Compound 10 (Example 3)

To a stirred solution of compound (9) from the previous step in DCM (10 mL) at 0° C. was added TFA (5 mL). The mixture was stirred at 0° C. for 2 h followed by room temperature for 2 h while protected from light. The mixture was concentrated under reduced pressure and the residue purified using preparative HPLC, column: SunFire C18 OBD Column, 100 Å, 5 μm, 19 mm×250 mm; Mobile Phase A: Water (0.05% TFA), Mobile Phase B: MeCN; Flow rate: 25 mL/min; Gradient: 10% B to 30% B in 10 min; 254/220 nm; Rt: 8.76 min to obtain compound (10) (Example 3) (39 mg) as a colorless oil after freeze-drying.

m/z (ES+), [M+H]$^+$=310

$^1$H NMR: (400 MHz, Methanol-d4) δ, ppm, 3.84 (t, J=6.0 Hz, 1H), 3.26 (td, J=6.8, 3.5 Hz, 2H), 3.00 (td, J=7.5, 3.5 Hz, 2H), 2.54 (q, J=6.5 Hz, 2H), 2.21-2.10 (m, 2H), 1.82-1.72 (m, 2H), 1.72-1.51 (m, 2H), 1.09 (d, J=6.7 Hz, 5H).

Synthesis of Compound 14 (Example 4)

Example 4 was synthesized according to the scheme below:

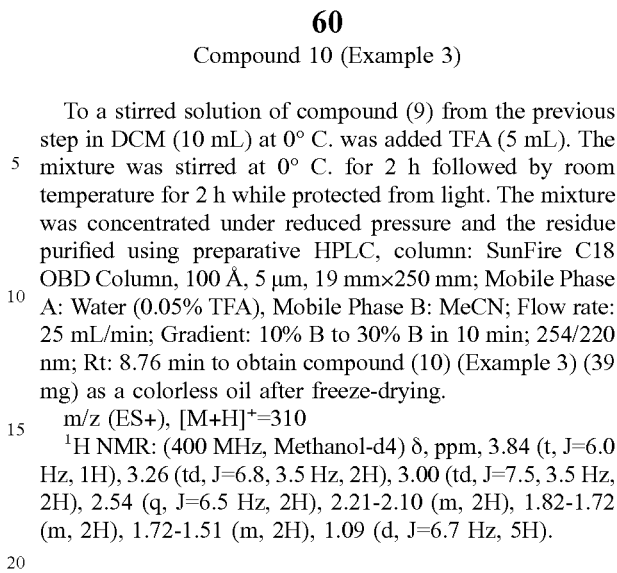

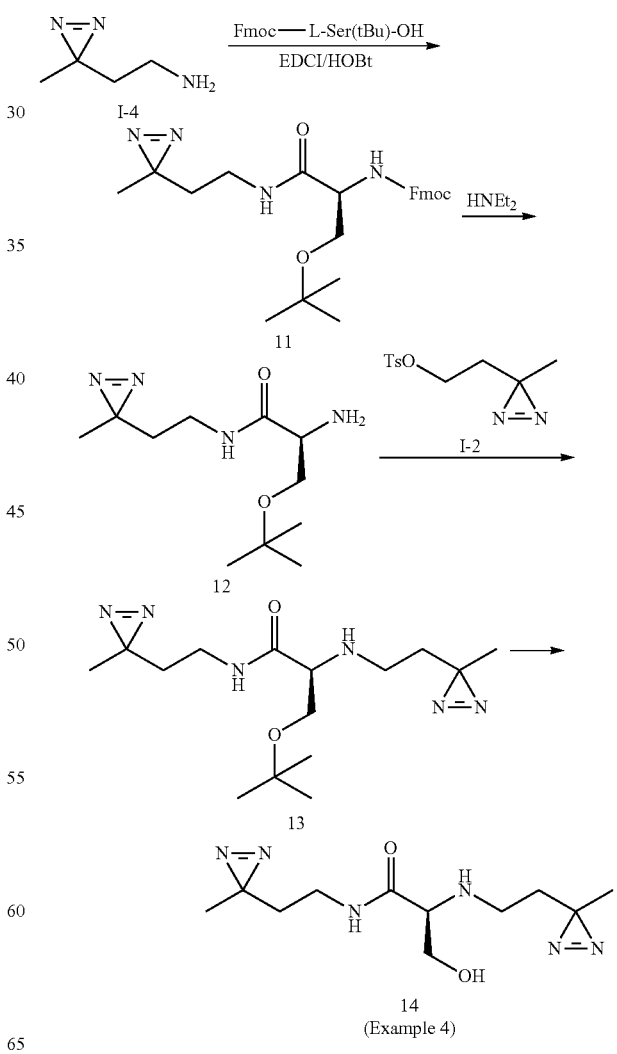

14
(Example 4)

Compound 11

DIPEA (0.96 g, 7.5 mmol) was added dropwise to a stirred room temperature solution of intermediate (I-4) obtained from compound (ix) (500 mg, 2.5 mmol), Fmoc-L-Ser(tBu)-OH (960 mg, 2.5 mmol), HOBt (407 mg, 3 mmol) and EDCI (0.86 g, 5 mmol) in DMF (10 mL). The mixture was stirred at room temperature for 3 h with the exclusion of light, then quenched with water and extracted with EtOAc. The organic layer was washed with saturated brine, dried over anhydrous sodium sulfate and concentrated under reduced pressure to give compound (11) as a yellow oil which was used in the next step without further purification.

m/z (ES+), [M+H]$^+$=465.

Compound 12

Compound (11) obtained from the previous step was added to 10% diethylamine in THF (15 mL) and stirred at room temperature for 2 h protected from light. The mixture was concentrated under reduced pressure and the residue purified using silica gel chromatography to obtain compound (12) (480 mg) as a yellow solid.

m/z (ES+), [M+H]$^+$=243.

Compound 13

A mixture of compound (12) (480 mg, 1.98 mmol), intermediate (I-2) (757 mg, 2.98 mmol) and potassium carbonate (550.4 mg, 3.96 mmol) in DMF (15 mL) was stirred at 55° C. for 10 h protected from light. The mixture was diluted with ethyl acetate (50 mL) and washed with saturated brine and water. The organic layer was dried over anhydrous sodium sulfate and concentrated under reduced pressure to give compound (13) which was used directly in the next step without further purification.

m/z (ES+), [M+H]$^+$=324.

Compound 14 (Example 4)

To a stirred solution of compound (13) from the previous step in DCM (10 mL) at 0° C. was added TFA (5 mL). The mixture was stirred at 0° C. for 2 h followed by room temperature for 2 h while protected from light. The mixture was concentrated under reduced pressure and the residue purified using preparative HPLC, column: SunFire C18 OBD Prep Column, 100 Å, 5 μm, 19 mm×250 mm; mobile Phase A: Water (0.05% TFA), Mobile Phase B: MeCN; Flow rate: 25 mL/min; Gradient: 10% B to 30% B in 10 min; 254/220 nm; Rt: 8.38 min to give compound (14) (Example 4) (71 mg) as a colorless oil after freeze-drying.

m/z (ES+), [M+H]$^+$=310

$^1$H NMR: (400 MHz, Methanol-d4) δ, ppm, 4.02 (q, J=7.1 Hz, 1H), 3.95-3.85 (m, 2H), 3.31-3.17 (m, 2H), 3.06 (dd, J=9.6, 7.3 Hz, 2H), 1.85-1.71 (m, 2H), 1.71-1.53 (m, 2H), 1.08 (d, J=7.0 Hz, 6H).

Synthesis of Compound 18 (Example 5)

Example 5 was synthesized according to the scheme below:

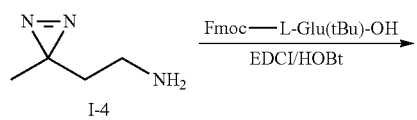

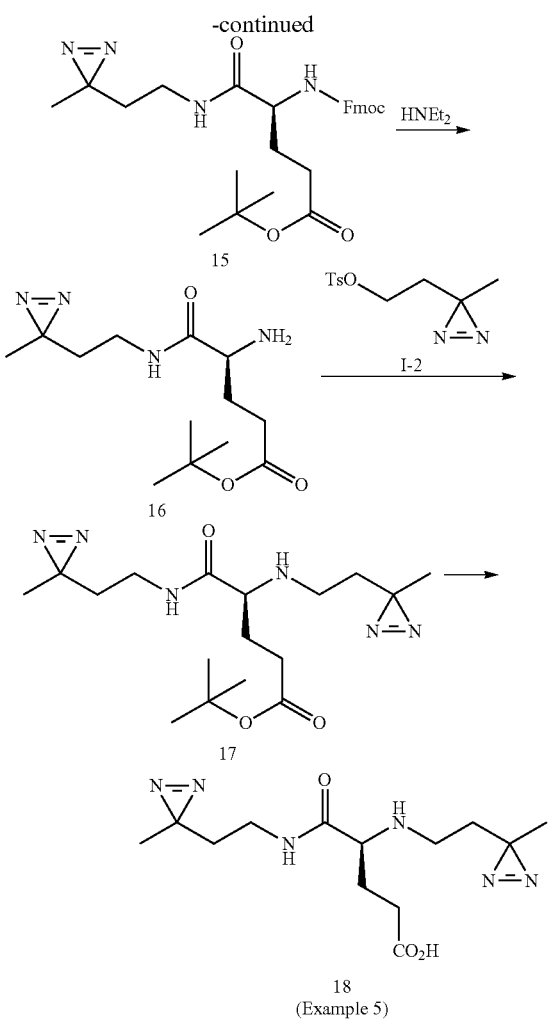

Compound 15

DIPEA (0.96 g, 7.5 mmol) was added dropwise to a stirred room temperature solution of intermediate (I-4) obtained from compound (ix) (500 mg, 2.5 mmol), Fmoc-L-Glu(tBu)-OH·H$_2$O (1.06 g, 2.5 mmol), HOBt (407 mg, 3 mmol) and EDCI (0.86 g, 5 mmol) in DMF (10 mL). The mixture was stirred at room temperature for 3 h with the exclusion of light, then quenched with water and extracted with EtOAc. The organic layer was washed with saturated brine, dried over anhydrous sodium sulfate and concentrated under reduced pressure. The residue was purified using silica gel chromatography to give compound (15) (520 mg) as a yellow oil.

m/z (ES+), [M+H]$^+$=507.

Compound 16

Compound (15) (520 mg, 1.03 mmol) was added to 10% diethylamine in THF (15 mL) and stirred at room temperature for 2 h protected from light. The mixture was concentrated under reduced pressure to give compound (16) which was used in the next step without further purification.

m/z (ES+), [M+H]$^+$=285.

Compound 17

A mixture of compound (16) obtained from the previous step, intermediate (I-2) (381 mg, 1.5 mmol) and potassium carbonate (278.1 mg, 2 mmol) in DMF (15 mL) was stirred at 55° C. for 10 h protected from light. The mixture was diluted with ethyl acetate (50 mL) and washed with saturated brine and water. The organic layer was dried over anhydrous sodium sulfate and concentrated under reduced pressure. The residue was purified using silica gel chromatography to obtain to give compound (17) (150 mg) as a yellow oil.

m/z (ES+), [M+H]$^+$=367.

Compound 18 (Example 5)

To a stirred solution of compound (17) (150 mg, 0.51 mmol) in DCM (10 mL) at 0° C. was added TFA (5 mL). The mixture was stirred at 0° C. for 2 h followed by room temperature for 2 h while protected from light. The mixture was concentrated under reduced pressure and the residue purified using preparative HPLC, column: Atlantis Prep T3 OBD Column 19×150 mm 5 µm; Mobile Phase A: Water (0.05% TFA), Mobile Phase B: MeCN; Flow rate: 20 mL/min; Gradient: 20% B to 20% B in 8 min; 254/220 nm; Rt: 7.57 min. To give compound (18) (Example 5) (11.3 mg) as a colorless oil after freeze-drying.

m/z (ES+), [M+H]$^+$=311

$^1$H NMR: (300 MHz, Methanol-d4) δ, ppm, 3.84 (t, J=6.2 Hz, 1H), 3.26 (d, J=6.9 Hz, 3H), 3.07-2.94 (m, 2H), 2.52 (td, J=7.2, 3.2 Hz, 2H), 2.18 (dd, J=8.8, 5.6 Hz, 2H), 1.83-1.69 (m, 2H), 1.63 (dt, J=13.3, 6.5 Hz, 2H), 1.13-1.04 (m, 6H).

Synthesis of Compound 25 (Example 6)

Example 6 was synthesized according to the scheme below:

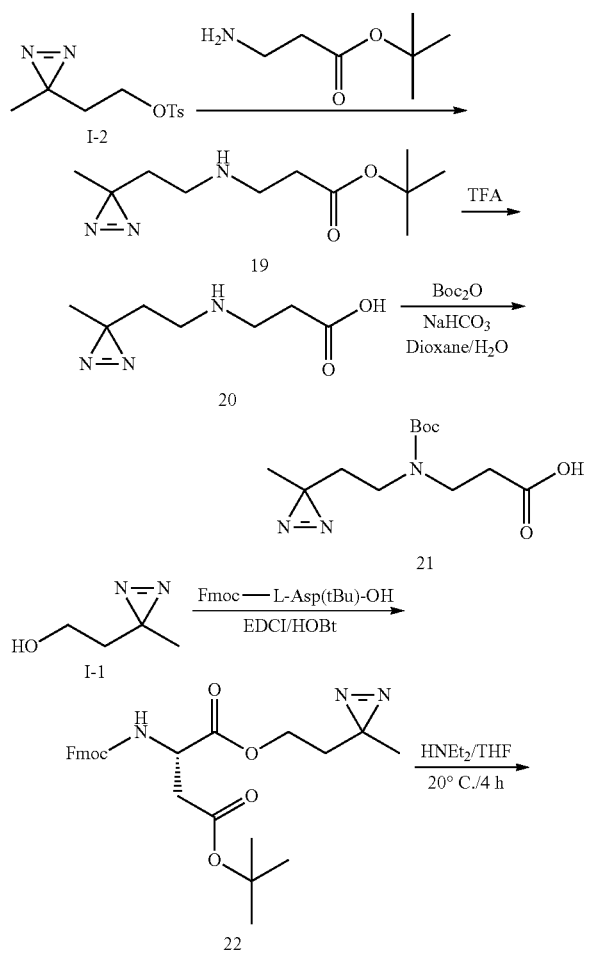

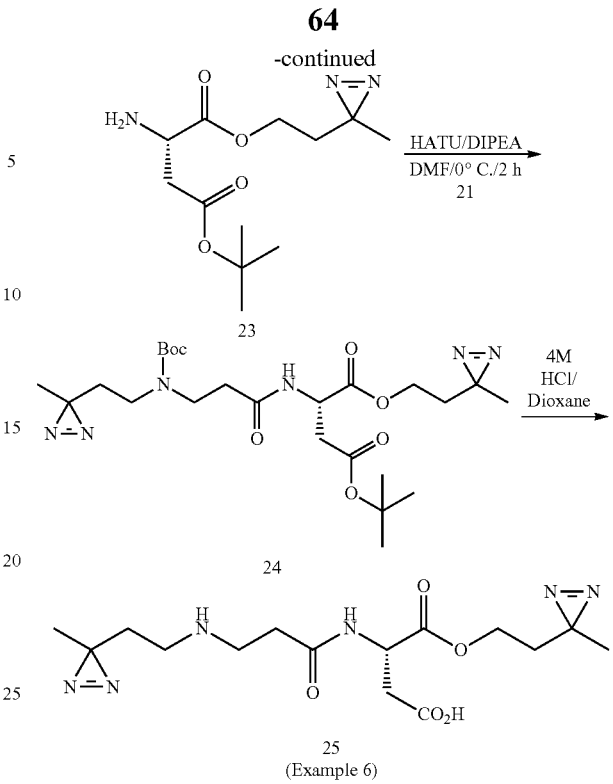

Compound 19

To a stirred 0° C. solution of intermediate (I-2) (2.30 g, 9.04 mmol) and tert-butyl 3-aminopropanoate (5.25 g, 36.18 mmol) in MeCN (30 mL) was added K$_2$CO$_3$ (12.50 g, 90.45 mmol). The mixture was stirred for 16 h at 60° C. before being concentrated under reduced pressure. The residue was diluted with water (100 mL), extracted with EtOAc (3×100 mL). The combined organic layers were washed with water (3×100 mL), saturated brine (200 mL) and dried over anhydrous Na$_2$SO$_4$. After filtration, the filtrate was concentrated under reduced pressure and the residue purified by silica gel column chromatography, eluted with PE/EtOAc (3:1) to afford compound (19) (1.5 g) as a colorless oil.

ESI-MS m/z=228.5[M+H]$^+$.

Compound 20

To a stirred solution of compound (19) (1.50 g, 6.6 mmol) in DCM (10 mL) was added TFA (10 mL). The mixture was stirred for 6 h at 20° C. before being concentrated under reduced pressure to give compound (20) which was used for the next step without further purification ESI-MS m/z=172.2 [M+H]$^+$.

Compound 21

To a stirred 0° C. mixture of compound (20) (1 g, 5.84 mmol) in 1,4-dioxane (50 mL) and saturated aqueous NaHCO$_3$ (50 mL) was added di-tert-butyl dicarbonate (1.91 g, 8.75 mmol) in portions. The mixture was subsequently stirred for 16 h at 20° C. before being concentrated under reduced pressure. The residue was extracted with EtOAc (2×100 mL) which was discarded and the remaining solution acidified to pH 6 with 1M HCl. The resulting mixture was extracted with EtOAc (3×300 mL). The combined organic layers were washed with water (2×300 mL) and dried over anhydrous Na$_2$SO$_4$. After filtration, the filtrate was concentrated under reduced pressure and the residue purified using reverse phase silica gel chromatography using the following conditions: Column, C18 silica gel; mobile phase, A: 0.05% formic acid in water, B: MeCN, 10% to 100% gradient in 25 min; detector, UV 200 nm to afford compound (21) (1 g) as a colorless oil.

ESI-MS m/z=272.3 [M+H]$^+$; 294.2[M+Na]$^+$.

Compound 22

To a stirred 0° C. solution of compound (21) (3 g, 7.29 mmol) in DMF (100 mL) were added intermediate (I-1) (0.80 g, 8.02 mmol), DIPEA (1884.68 mg, 14.58 mmol), HOBT (197.04 mg, 1.46 mmol) and EDCI (1471.46 mg, 9.48 mmol). The resulting mixture was stirred for 16 h at 20° C. before being diluted with water (300 mL) and extracted with EtOAc (3×300 mL). The combined organic layers were washed with water (2×300 mL), saturated aqueous NaCl (300 mL) and dried over anhydrous Na$_2$SO$_4$. After filtration, the filtrate was concentrated under reduced pressure and the residue purified by silica gel column chromatography, eluted with PE/EtOAc (4:1) to afford compound (22) (3 g) as an off-white solid.

ESI-MS m/z=494 [M+H]$^+$; 516[M+Na]$^+$.

$^1$H NMR: (400 MHz, Chloroform-d) δ, ppm, 7.79 (d, J=7.5 Hz, 2H), 7.63 (dd, J=7.9, 2.8 Hz, 2H), 7.43 (t, J=7.5 Hz, 2H), 7.38-7.31 (m, 2H), 5.86 (d, J=8.7 Hz, 1H), 4.64 (dt, J=8.9, 4.5 Hz, 1H), 4.48-4.33 (m, 2H), 4.28 (t, J=7.3 Hz, 1H), 4.15 (qd, J=7.2, 6.5, 2.0 Hz, 2H), 2.95 (ddd, J=84.3, 17.1, 4.5 Hz, 2H), 1.72 (td, J=6.3, 3.2 Hz, 2H), 1.48 (s, 9H), 1.08 (s, 3H).

Compound 23

Diethylamine (15 mL) was added dropwise to a stirred 0° C. solution of compound (22) (2 g, 4.05 mmol) in THF (30 ml). The mixture was stirred for 4 h at 20° C. before being concentrated under reduced pressure. The residue was purified by silica gel column chromatography, eluted with PE/EtOAc (10:1), then DCM/MeOH (7:1) to afford compound (23) (1 g) as a light yellow oil.

ESI-MS m/z=272.2 [M+H]$^+$.

Compound 24

To a 0° C. stirred solution of compound (23) (600 mg, 2.21 mmol) and compound (21) (600 mg, 2.21 mmol) in DMF (5 mL) were added DIPEA (857.44 mg, 6.63 mmol) and HATU (1261.28 mg, 3.32 mmol). The mixture was stirred at 0° C. for 2 h before being diluted with water (50 mL) and extracted with EtOAc (3×30 mL). The combined organic layers were washed with water (3×30 mL), saturated brine (50 mL) and dried over anhydrous Na$_2$SO$_4$.

After filtration, the filtrate was concentrated under reduced pressure and the residue purified by reverse phase silica gel chromatography using the following conditions: column, C18 silica gel; mobile phase, A: 0.05% formic acid in water, B: MeCN, 30 min 0-100% B, detector, UV 200 nm to afford compound (24) (800 mg) as a light yellow oil.

ESI-MS m/z=525.3 [M+H]$^+$; 547.3[M+Na]$^+$.

Compound 25 (Example 6)

To a 0° C. stirred solution of compound (24) (800 mg, 1.53 mmol) in 1,4-dioxane (10 mL) was added 4M HCl in 1,4-dioxane (20 mL) dropwise. The resulting mixture was stirred for 6 h at 20° C. before being concentrated under reduced pressure to afford compound (25) (Example 6) (550 mg) as a light yellow oil.

ESI-MS m/z=369.0 [M+H]$^+$.

$^1$H-NMR: (400 MHz, Methanol-d4): δ, ppm, 4.85-4.75 (m, 1H), 4.20-4.00 (m, 2H), 3.30 (dt, J=6.4, 3.0 Hz, 2H), 3.15-3.00 (m, 2H), 3.00-2.80 (m, 2H), 2.74 (dtd, J=12.6, 6.3, 2.7 Hz, 2H), 1.80-1.73 (m, 2H), 1.71 (ddt, J=8.3, 6.7, 2.5 Hz, 1H), 1.11 (s, 3H), 1.09-1.01 (m, 3H).

Synthesis of Compound 29 (Example 7)

Example 7 was synthesized according to the scheme below:

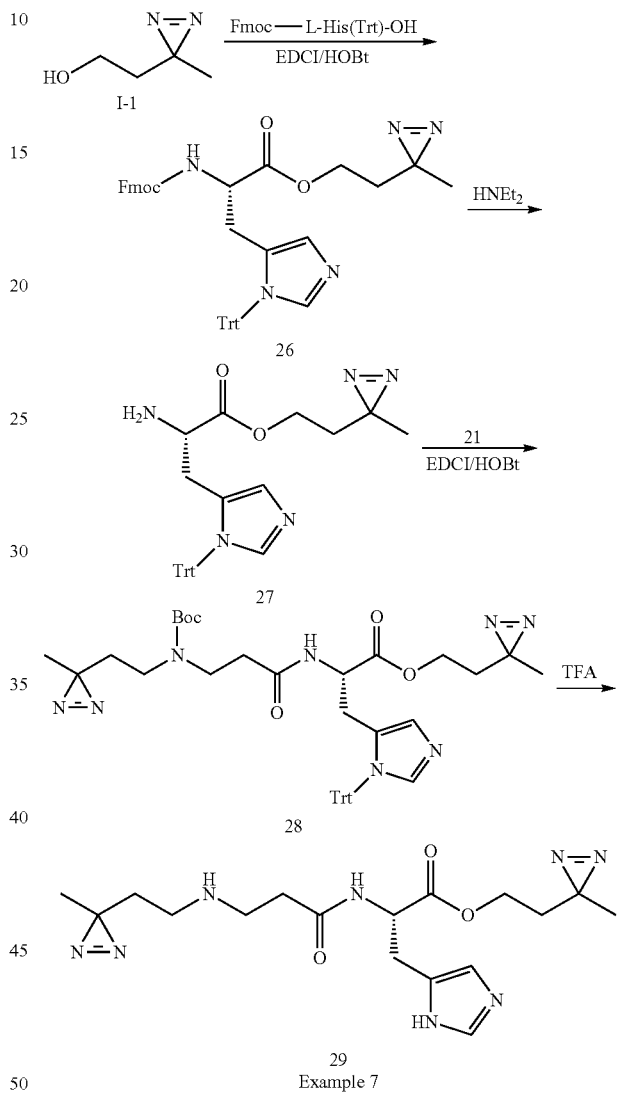

29
Example 7

Compound 26

EDCI (361 mg, 1.88 mmol) was added to Fmoc-L-His (Trt)-OH (774.7 mg, 1.25 mmol), intermediate (I-1) (250 mg, 2.5 mmol) and N,N-dimethylaminopyridine (5 mg, 0.125 mmol) in DCM (15 mL). The mixture was stirred at room temperature for 2 h protected from light before being diluted with DCM (50 mL), washed with water (20 mL), and saturated brine (10 mL). The organic layer was dried over anhydrous sodium sulfate, filtered and evaporated. The residue was purified using silica gel chromatography to give compound (26) (841 mg).

m/z (ES+), [M+H]$^+$=702.

Compound 27

Compound (26) (841 mg, 1.2 mmol) was dissolved in 10% diethylamine in THF (10 mL) and stirred at room temperature for 2 h protected from light. The mixture was concentrated under reduced pressure and the residue purified using silica gel chromatography to obtain compound (27) (420 mg) as a yellow solid.

m/z (ES+), [M+H]$^+$=480.

$^1$H NMR: (300 MHz, Chloroform-d) δ, ppm, 7.79 (d, J=7.5 Hz, 2H), 7.63 (d, J=7.4 Hz, 2H), 7.43 (t, J=7.4 Hz, 2H), 7.38-7.31 (m, 2H), 4.43 (d, J=7.8 Hz, 3H), 4.25 (t, J=6.9 Hz, 1H), 4.11 (t, J=6.3 Hz, 2H), 3.15 (s, 2H), 1.73 (t, J=6.2 Hz, 3H), 1.65-1.50 (m, 3H), 1.46 (s, 11H).

Compound 28

A mixture of compound (27) (420 mg, 0.88 mmol), compound (21) (271 mg, 1.00 mmol), PyBOP (0.91 g, 1.75 mmol) and DIPEA (338.6 mg, 2.63 mmol) in DMF (10 mL) was stirred at room temperature overnight protected from light. The mixture was quenched and extracted with ethyl acetate. The organic layer was washed with saturated brine, dried over anhydrous sodium sulfate and concentrated under reduced pressure to give compound (28) (490 mg).

m/z (ES+), [M+H]$^+$=733.

Compound 29 (Example 7)

To a 0° C. solution of compound (28) (490 mg, 0.67 mmol) in DCM (10 mL) was added TFA (5 mL). The mixture was stirred at 0° C. for 2 h followed by room temperature for 2 h while being protected from light. The mixture was concentrated under reduced pressure and the residue purified by preparative HPLC, column: XBridge Prep Phenyl OBD column 19×150 mm, 5 µm; Mobile Phase A: Water (0.05% TFA), Mobile Phase B: MeCN; Flow rate: 20 mL/min; Gradient: 15% B to 15% B in 7 min; 254/220 nm; Rt: 4.92 min to afford compound (29) (Example 7) (62.7 mg) as a colorless oil after freeze-drying.

m/z (ES+), [M+H]$^+$=391.

$^1$H NMR: (300 MHz, Methanol-d4) δ, ppm, 8.88 (d, J=1.4 Hz, 1H), 7.42 (d, J=1.4 Hz, 1H), 4.87-4.80 (m, 2H), 4.13 (t, J=6.1 Hz, 2H), 3.39 (dd, J=15.5, 6.0 Hz, 1H), 3.30-3.15 (m, 3H), 3.10-2.95 (m, 2H), 2.74 (dt, J=7.3, 3.4 Hz, 2H), 1.84-1.65 (m, 4H), 1.08 (d, J=13.2 Hz, 6H).

Synthesis of Compound 33 (Example 8)

Example 8 was synthesized according to the scheme below:

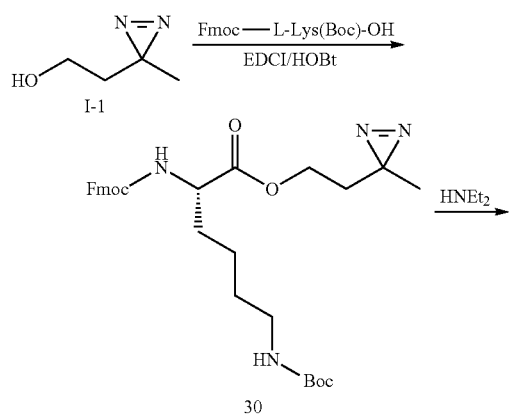

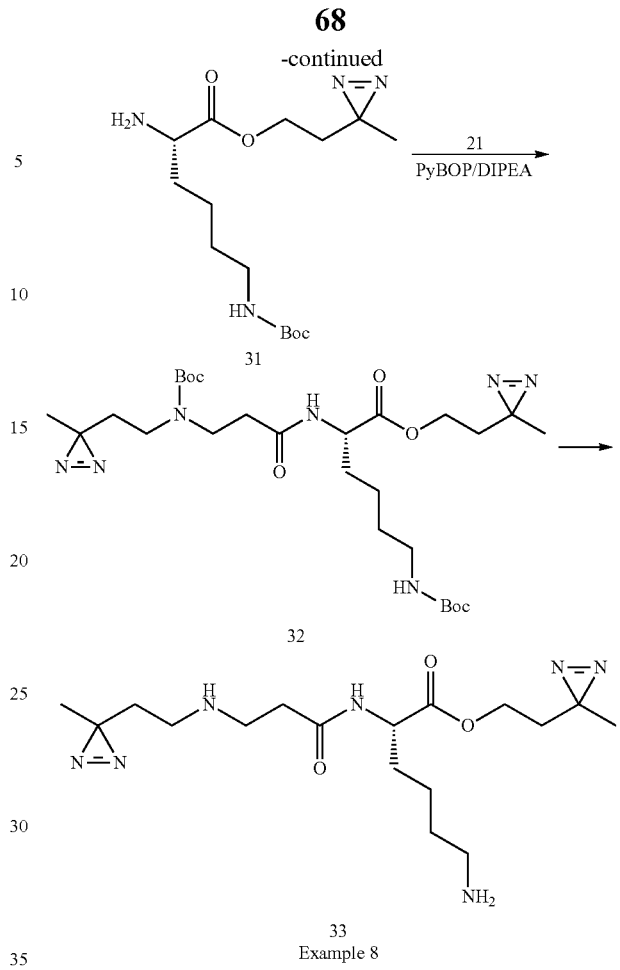

Compound 30

EDCI (361 mg, 1.88 mmol) was added to Fmoc-L-Lys (Boc)-OH (585.7 mg, 1.25 mmol), intermediate (I-1) (250 mg, 2.5 mmol) and N,N-dimethylaminopyridine (5 mg, 0.13 mmol) in DCM (15 mL). The mixture was stirred at room temperature for 2 h protected from light before being diluted with DCM (50 mL), washed with water (20 mL) and saturated brine (10 mL). The organic layer was dried over anhydrous sodium sulfate, filtered and concentrated under reduced pressure. The residue was purified using silica gel chromatography to give compound (30) (717 mg).

m/z (ES+), [M+Na]$^+$=573.

Compound 31

Compound (30) (717 mg, 1.31 mmol) was dissolved in 10% diethylamine in THF (10 mL) and the mixture stirred at room temperature for 2 h protected from light. The mixture was concentrated under reduced pressure and the residue purified using silica gel chromatography to obtain compound (31) (240 mg) as a yellow solid.

m/z (ES+), [M+H]$^+$=329.

Compound 32

A solution of compound (31) (240 mg, 0.73 mmol), compound (21) (271 mg, 1.00 mmol), PyBOP (0.76 g, 1.46 mmol), and DIPEA (282 mg, 2.19 mmol) in DMF (10 mL) was stirred at room temperature overnight protected from light. The mixture was quenched with water and extracted with EtOAc. The organic layer was washed with saturated brine and dried over anhydrous sodium sulfate before being concentrated under reduced pressure to give compound (32) (620 mg).

m/z (ES+), [M+H]$^+$=582.

Compound 33 (Example 8)

To a 0° C. solution of compound (32) (620 mg, 1.07 mmol) in DCM (10 mL) was added TFA (5 mL). The mixture was stirred at 0° C. for 2 h followed by room temperature for 2 h while being protected from light. The mixture was concentrated under reduced pressure and the residue purified by preparative HPLC, column: XBridge Prep Phenyl OBD column 19×150 mm, 5 μm Mobile Phase A: Water (0.05% TFA), Mobile Phase B: MeCN; Flow rate: 20 mL/min; Gradient: 15% B to 15% B in 7 min; 254/220 nm; Rt: 4.92 min to afford compound (33) (Example 8) (47.7 mg) as a colorless oil after freeze-drying.

m/z (ES+), [M+H]$^+$=382.

$^1$H NMR: (300 MHz, Methanol-d4) δ, ppm, 4.44 (s, 1H), 4.09 (s, 2H), 2.98 (dt, J=25.9, 7.8 Hz, 4H), 2.73 (t, J=6.0 Hz, 2H), 1.94 (s, 1H), 1.85-1.58 (m, 6H), 1.51 (d, J=8.0 Hz, 2H), 1.06 (dd, J=9.3, 2.0 Hz, 5H).

Synthesis of Compound 37 (Example 9)

Example 9 was synthesized according to the scheme below:

water (2×100 mL), saturated brine (100 mL) and dried over anhydrous Na$_2$SO$_4$. After filtration, the filtrate was concentrated under reduced pressure and the residue purified using silica gel column chromatography, eluted with PE/EtOAc (3:1) to afford compound (34) (2 g) as a light yellow solid.

ESI-MS m/z=493 [M+H]$^+$; 515 [M+Na]$^+$.

Compound 35

To a 0° C. stirred solution of compound (34) (600 mg, 1.25 mmol) in THF (15 mL) was added diethylamine (15 mL). The mixture was stirred for 4 hours at 20° C. before being concentrated under reduced pressure. The residue was purified using silica gel column chromatography, eluted with PE/EtOAc=10:1 then DCM/MeOH (10:1) to afford compound (35) (300 mg) as a light yellow oil.

ESI-MS m/z=271.4 [M+H]$^+$.

Compound 36

To a 0° C. stirred solution of compound (21) (300 mg, 1.11 mmol) and compound (35) (300 mg, 1.11 mmol) in DMF (5.00 mL) was added DIPEA (428.72 mg, 3.32 mmol) and HATU (630.64 mg, 1.66 mmol) in portions. The mixture was stirred for 2 hours at 0° C. before being concentrated under reduced pressure and the residue purified by reverse phase silica gel chromatography using the following conditions: Column, C18 silica gel; mobile phase, A: 0.5%

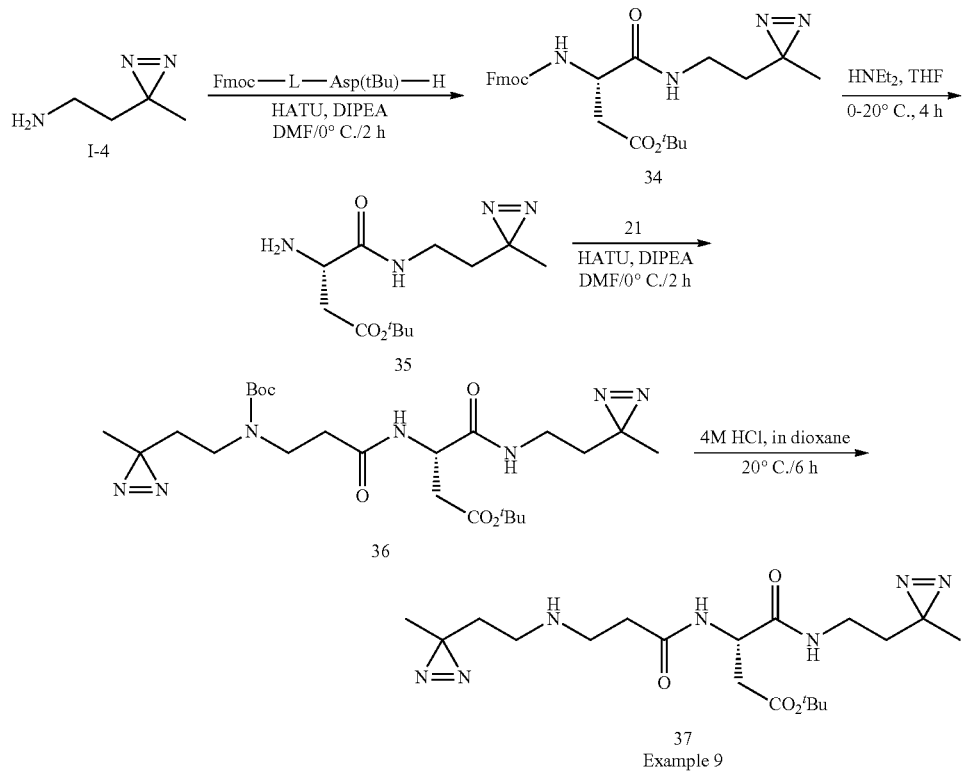

Compound 34

To a 0° C. stirred solution of (2S)-4-(tert-butoxy)-2-([[(9H-fluoren-9-yl)methoxy]carbonyl]amino)-4-oxobutanoic acid (6.23 g, 15.13 mmol) and intermediate (I-4) (1.50 g, 15.13 mmol) in DMF (50 mL) was added DIPEA (11.73 g, 90.78 mmol) and HATU (8.63 g, 22.69 mmol) in portions. The mixture was stirred for 2 h at 0° C. before being diluted with water (100 mL) and extracted with EtOAc (3×100 mL). The organic layer was washed with NH$_4$HCO$_3$ in water, 0-100 B % in 30 min, B: MeCN, detector: UV 200 nm, 60% B to afford compound (36) (300 mg) as a colorless oil.

ESI-MS m/z=524.4 [M+H]$^+$; 546.3 [M+Na]$^+$.

Compound 37 (Example 9)

A solution of compound (36) (180 mg, 34.40 mmol) in 4M HCl in 1,4-dioxane (4.0 mL) was stirred at 20° C. The mixture was concentrated under reduced pressure and the residue purified by reverse phase silica gel chromatography using the following conditions: Column, C18 silica gel; mobile phase, A: 0.01% HCl in water; B: MeCN, 0% to 100% gradient in 25 min; detector, UV 200 nm to afford compound (37) (Example 9) (144 mg, 99.78%) as a light yellow semi-solid.

ESI-MS m/z=368.1 [M+H]$^+$.

$^1$H-NMR: (400 MHz, Methanol-d4): δ, ppm, 4.71 (dd, J=8.3, 5.3 Hz, 1H), 3.29 (d, J=6.2 Hz, 2H), 3.17 (hept, J=6.8 Hz, 2H), 3.08-3.02 (m, 2H), 2.88 (dd, J=16.9, 5.3 Hz, 1H), 2.79-2.66 (m, 3H), 1.81-1.69 (m, 2H), 1.55 (t, J=7.1 Hz, 2H), 1.11 (s, 3H), 1.04 (s, 3H).

Synthesis of Compound 43 (Example 10)

Example 10 was synthesized according to the scheme below:

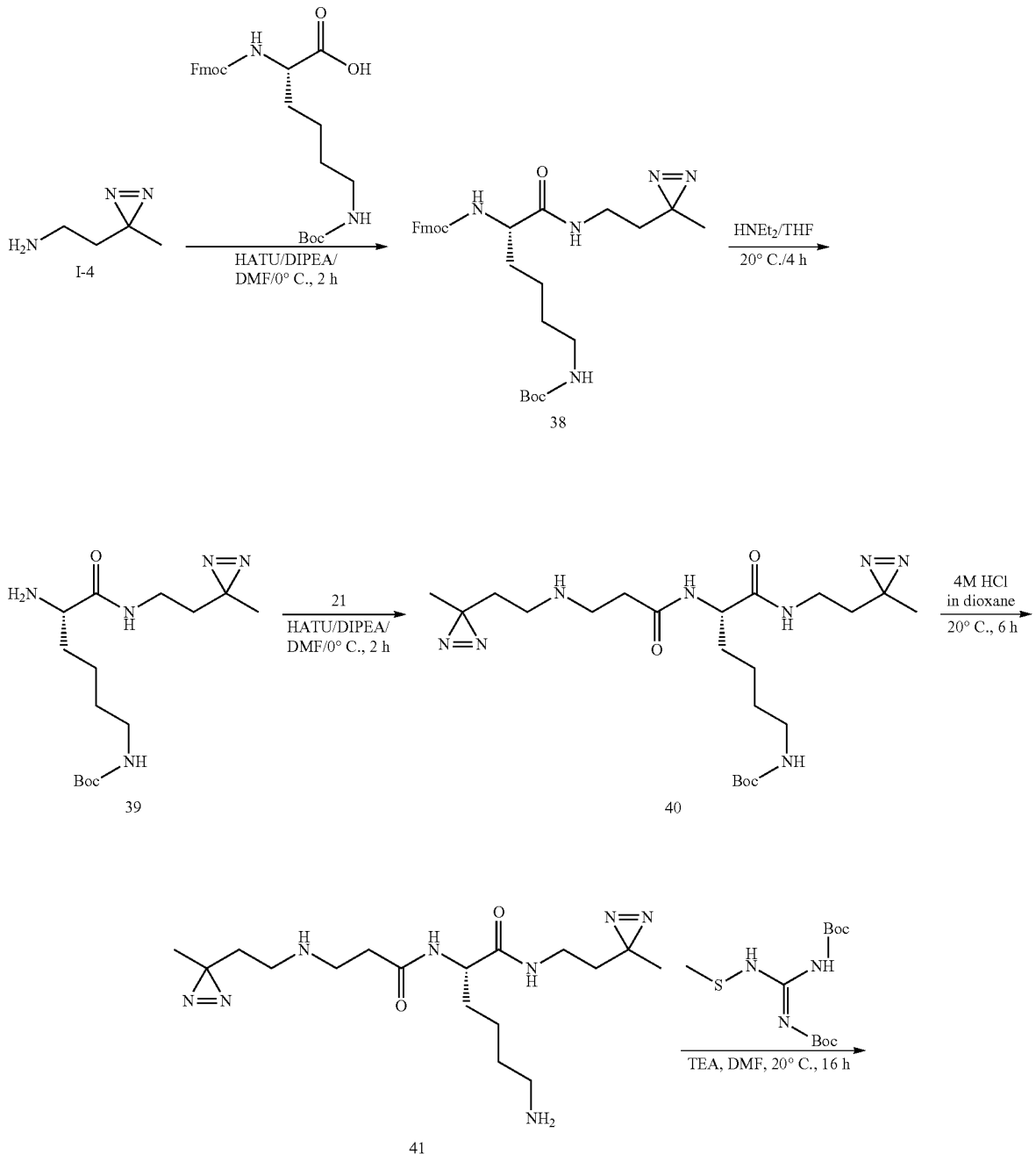

-continued

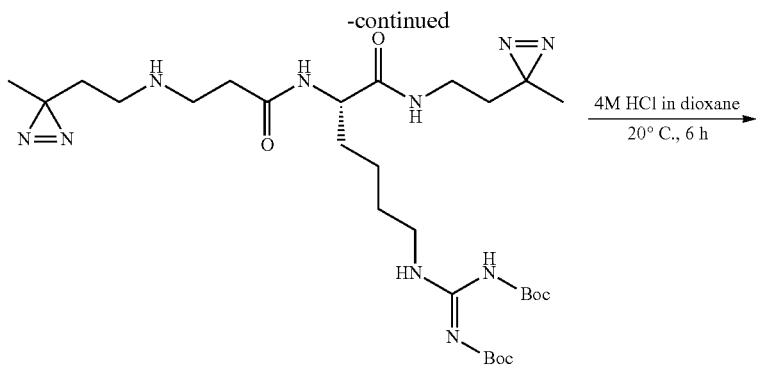

42

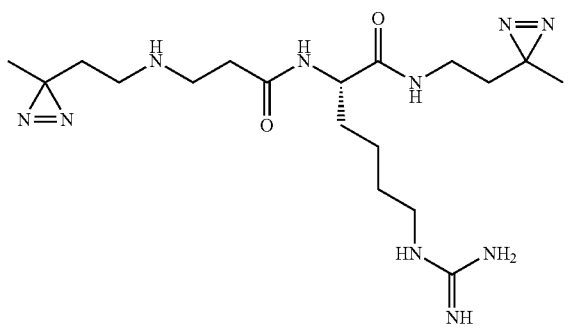

43
Example 10

Compound 38

To a 0° C. stirred solution of intermediate (I-4) (800 mg, 4.10 mmol) and (2S)-6-[[(tert-butoxy)carbonyl]amino]-2-([[(9H-fluoren-9-yl)methoxy]carbonyl]amino)hexanoic acid (1920.83 mg, 4.10 mmol) in DMF (10 mL) was added DIPEA (3179.01 mg, 24.6 mmol) and HATU (2026.08 mg, 5.33 mmol). The mixture was stirred for 2 h at 0° C. before being diluted with water (200 mL) and extracted with EtOAc (3×100 mL). The combined organic layers were washed with water (2×100 mL), saturated brine (200 mL) and dried over anhydrous $Na_2SO_4$. After filtration, the filtrate was concentrated under reduced pressure and the residue purified by reverse phase silica gel chromatography using the following conditions: Column, C18 silica gel; mobile phase, A: 0.05% $NH_4HCO_3$ in water; B: MeCN, detector: 200 nm, 80% B to afford compound (38) (1.2 g) as a light yellow solid.

ESI-MS m/z=572.4 $[M+Na]^+$.

Compound 39

To a solution of compound (38) (600 mg, 1091.56 mmol) in THF (60 mL) was added diethylamine (30 mL). The resulting mixture was stirred for 4 h at 20° C. before being concentrated under reduced pressure. The residue was purified by silica gel column chromatography, eluted with PE/EtOAc (10:1) then DCM/MeOH (7:1) to afford compound (39) (300 mg) as a colorless oil.

ESI-MS m/z=328.2$[M+H]^+$.

Compound 40

To a 0° C. stirred solution of compound (21) (248.59 mg, 0.92 mmol) and compound (39) (300 mg, 0.92 mmol) in DMF (5 mL) were added DIPEA (355.25 mg, 2.75 mmol) and HATU (522.57 mg, 1.37 mmol). The mixture was stirred for 2 h at 0° C. before being concentrated under reduced pressure and the residue purified by reverse phase silica gel chromatography using the following conditions: Column, C18 silica gel; mobile phase, A: 0.05% $NH_4HCO_3$ in water; B: MeCN, detector, 200 nm; 10% to 80% gradient in 20 min to afford compound (40) (300 mg) as a colorless oil.

ESI-MS m/z=581.4 $[M+H]^+$.

Compound 41

Compound (40) (300 mg) was stirred for 6 h at 20° C. in 4M HCl in 1,4-dioxane (15 mL).

The resulting mixture was concentrated under reduced pressure to afford compound (41) which was used for the next step without further purification.

ESI-MS m/z=381.3 $[M+H]^+$.

Compound 42

To a 0° C. stirred solution of compound (41) (290 mg, 0.76 mmol) and tert-butyl N-[(1E)-[[(tert-butoxy)carbonyl]amino][(methylsulfanyl)amino]methylidene]carbamate (465.51 mg, 1.52 mmol) in DMF (5.00 mL) was added TEA (0.23 g, 2.27 mmol) and N,N-dimethylaminopyridine (18.62 mg, 0.15 mmol) in portions. The mixture was stirred overnight at 20° C. before being concentrated under reduced pressure and the residue purified by reverse phase silica gel chromatography using the following conditions: Column, C18 silica gel; mobile phase, A: 0.05% formic acid in water, B: MeCN, detector, UV 254 nm, 10% to 90% gradient in 25 min to afford compound (42) (200 mg) as a yellow oil.

ESI-MS m/z=623.5 $[M+H]^+$.

Compound 43 (Example 10)

Compound (42) (200 mg, 0.32 mmol) in 4M HCl in 1,4-dioxane (5 mL) was stirred for 6 h at 20° C. The mixture was concentrated under reduced pressure and the residue purified by reverse phase silica gel chromatography using the following conditions: Column, C18 silica gel; mobile phase, A: 0.01% HCl in water B: MeCN; 0% to 100% gradient in 30 min; detector, UV 200 nm to afford compound (43) (Example 10) (83 mg) as a light yellow semi-solid.

ESI-MS m/z=423.3 [M+H]+

$^1$H NMR: (400 MHz, Methanol-d4); δ, ppm, 4.25-4.34 (m, 1H), 3.30-3.24 (m, 2H), 3.26-3.09 (m, 4H), 3.09-3.01 (m, 2H), 2.78 (td, J=6.4, 3.3 Hz, 2H), 1.94-1.81 (s, 1H), 1.81-1.70 (m, 3H), 1.70-1.61 (m, 2H), 1.60-1.33 (m, 4H), 1.11 (s, 3H), 1.05 (s, 3H).

Synthesis of Compound 45 (Example 11)

Example 11 was synthesized according to the scheme below:

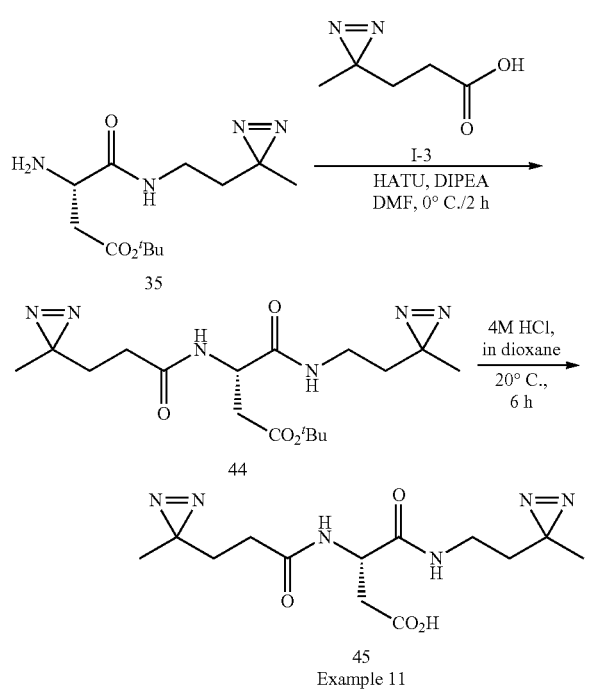

Compound 44

To a 0° C. stirred solution of intermediate (I-3) (94.79 mg, 0.74 mmol) and compound (35) (200 mg, 0.74 mmol) in DMF (2 mL) was added DIPEA (382.47 mg, 2.96 mmol) and HATU (365.74 mg, 0.96 mmol). The mixture was stirred for 2 h at 0° C., concentrated under reduced pressure and the residue purified by reverse phase silica gel chromatography using the following conditions: Column, C18 silica gel; mobile phase, A: 0.05% NH$_4$HCO$_3$ in water; B: MeCN, 70% B to afford compound (44) (300 mg) as a light yellow oil.

ESI-MS m/z=381.2 [M+H]+.

Compound 45 (Example 11)

Compound (44) (100 mg, 0.53 mmol) in 4M HCl in dioxane (5 mL) was stirred for 6 h at 20° C. The resulting mixture was concentrated under vacuum and the residue purified by reverse phase silica gel chromatography using the following conditions: Column, C18 silica gel; mobile phase, A: 0.01% formic acid in water; B: MeCN, 10% to 60% gradient in 20 min; detector, UV 200 nm to give compound (45) (Example 11) (53 mg) as white solid.

ESI-MS m/z=325.15 [M+H]+.

$^1$H-NMR: (300 MHz, DMSO-d6) δ, ppm, 12.3 (s, 1H), 8.15 (d, J=8.0 Hz, 1H), 7.83 (t, J=5.7 Hz, 1H), 4.51 (td, J=7.9, 5.8 Hz, 1H), 3.07-2.93 (m, 2H), 2.66 (dd, J=16.4, 5.9 Hz, 1H), 2.50-2.38 (m, 1H), 2.03 (dd, J=8.5, 7.1 Hz, 2H), 1.61-1.49 (m, 2H), 1.42 (t, J=7.2 Hz, 2H), 0.99 (d, J=3.8 Hz, 6H).

Synthesis of Compound 49 (Example 12)

Example 12 was synthesized according to the scheme below:

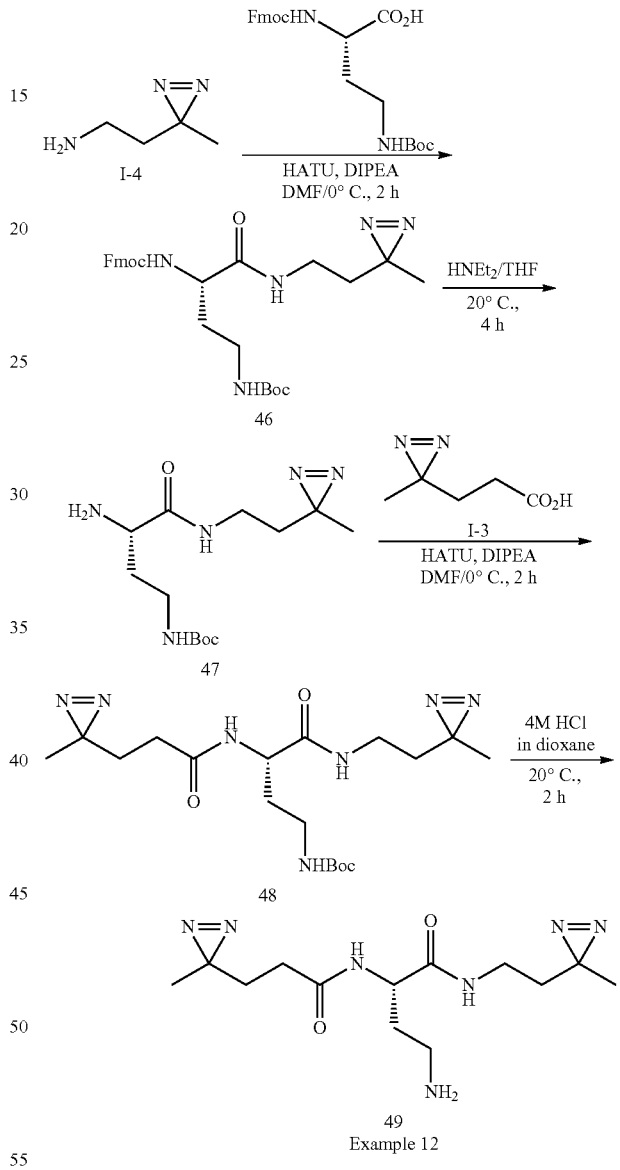

Compound 46

To a 0° C. stirred solution of intermediate (I-4) (800 mg, 8.07 mmol) and (2S)-4-[[(tert-butoxy)carbonyl]amino]-2-([[(9H-fluoren-9-yl)methoxy]carbonyl]amino)butanoic acid (3.55 g, 8.07 mmol) in DMF (10.00 mL) was added DIPEA (3.13 g, 24.21 mmol) and HATU (4.60 g, 12.10 mmol). The mixture was stirred for 2 h at 0° C. before being diluted with water (100 mL) and extracted with EtOAc (3×100 mL). The combined organic layers were washed with water (2×200 mL) and dried over anhydrous Na$_2$SO$_4$. After filtration, the filtrate was concentrated under reduced pressure and the residue purified by silica gel column chromatography, eluted with PE/EtOAc (3:1) to afford compound (46) (1 g) as a white solid.

ESI-MS m/z=522.3 [M+H]+.

Compound 47

Compound (46) (1 g, 1.92 mmol) and diethylamine (4 mL) in THE (20 mL) were stirred for 4 h at 20° C. The mixture was concentrated under reduced pressure and the residue purified by silica gel column chromatography, eluted with PE/EtOAc (10:1), then DCM/MeOH (7:1) to afford compound (47) (300 mg) as a light yellow oil.

ESI-MS m/z=300.4 [M+H]+.

Compound 48

To a 0° C. stirred solution of compound (47) (300 mg, 1.0 mmol) and intermediate (I-3) (128.4 mg, 1.0 mmol) in DMF (5.00 mL) was added HATU (495.33 mg, 1.30 mmol) and DIPEA (388.54 mg, 3.01 mmol). The mixture was stirred for 2 h at 0° C. before being concentrated under reduced pressure and the residue purified by reverse phase silica gel chromatography using the following conditions: Column, C18 silica gel; mobile phase, A: 0.05% $NH_4HCO_3$ in water; B: MeCN, detector: UV 200 nm, 0-100% B in 25 min, 50% B to afford compound (48) (300 mg) as a colorless oil.

ESI-MS m/z=410.3 [M+H]+.

Compound 49 (Example 12)

Compound (48) (300 mg, 0.73 mmol) in 4M HCl in dioxane (3 ml) was stirred for 2 h at 20° C. The mixture was concentrated under reduced pressure and the residue purified by reverse phase silica gel chromatography using the following conditions: Column, C18 silica gel; mobile phase, A: 0.05% $NH_4HCO_3$ in water; B: MeCN, 10% to 70% gradient; detector, UV 200 nm to compound (49) (Example 12) (206.8 mg) as a white solid.

ESI-MS m/z=310.2 [M+H]+.

1H-NMR: (400 MHz, Methanol-d4) δ, ppm, 4.47 (dd, J=8.4, 5.7 Hz, 1H), 3.19 (td, J=7.0, 3.1 Hz, 2H), 3.14-2.99 (m, 2H), 2.31-2.11 (m, 3H), 2.07-1.93 (m, 1H), 1.74 (t, J=7.5 Hz, 2H), 1.63-1.53 (m, 2H), 1.05 (d, J=3.4 Hz, 6H).

Synthesis of Compound 52 (Example 13)

Example 13 was synthesized according to the scheme below:

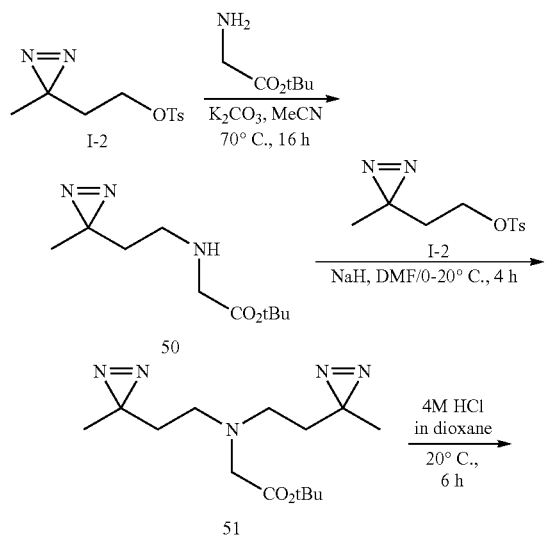

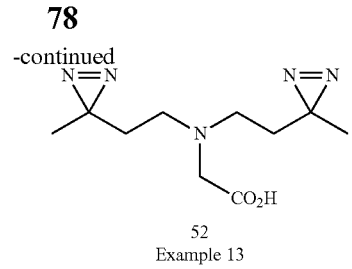

Example 13

Compound 50

To a room temperature stirred solution of intermediate (I-2) (2 g, 7.87 mmol) and tert-butyl 2-aminoacetate hydrochloride (3.09 g, 23.59 mmol) in MeCN (20 mL) was added $K_2CO_3$ (6.53 g, 47.33 mmol) The mixture stirred at 70° C. for 16 h before being concentrated under reduced pressure, diluted with water (200 mL) and extracted with EtOAc (3×200 mL). The combined organic layers were washed with water (2×300 mL), dried over anhydrous $Na_2SO_4$, filtered and the filtrate concentrated under reduced pressure. The residue was purified by silica gel chromatography eluted with PE/EtOAc (3:1) to afford compound (50) (1.2 g) as a light yellow oil.

ESI-MS m/z=214.3 [M+H]+.

Compound 51

To a 0° C. stirred solution of compound (50) (1.2 g, 5.63 mmol) in DMF (10 mL) was added NaH (0.68 g, 17.10 mmol) in portions. The mixture was stirred for 0.5 h at 0° C. before intermediate (I-2) (1.43 g, 5.63 mmol) in DMF (3 mL) was dropwise. The resulting mixture was stirred for 4 h at 20° C. before being quenched at 0° C. with sat aqueous $NH_4C_1$ (40 mL).

The mixture was extracted with EtOAc (3×30 mL), the combined organic layers washed with water (2×40 mL) and dried over anhydrous $Na_2SO_4$. After filtration, the filtrate was concentrated under reduced pressure and the residue purified by reverse phase silica gel chromatography using the following conditions: Column, C18 silica gel; mobile phase, A: 0.05% $NH_4HCO_3$ water, B: MeCN, 0% to 100% gradient in 25 min; detector, UV 200 nm to afford compound (51) (300 mg) as a light yellow oil.

ESI-MS m/z=296.2 [M+H]+.

Compound 52 (Example 13)

Compound (51) (200 mg, 0.68 mmol) in 4M HCl in dioxane (10 mL) was stirred for 6 h at 20° C. The mixture was concentrated under reduced pressure and the residue purified by preparative HPLC using the following conditions: Column: SunFire Prep C18 OBD Column 19×150 mm, 5 µm; Mobile Phase A: Water (0.1% formic acid), Mobile Phase B: MeCN; Flow rate: 25 mL/min; Gradient: 5% B to 25% B in 8 min; 254/220 nm; Rt: 7.23 min to afford compound (52) (Example 13) (53 mg) as a colorless oil.

ESI-MS m/z=240.2 [M+H]+.

1H-NMR: (300 MHz, Methanol-d4): δ, ppm, 3.54 (s, 2H), 3.13-3.01 (m, 4H), 1.79-1.68 (m, 4H), 1.08 (s, 6H).

Synthesis of Compound 54 (Example 14)

Example 14 was synthesized according to the scheme below:

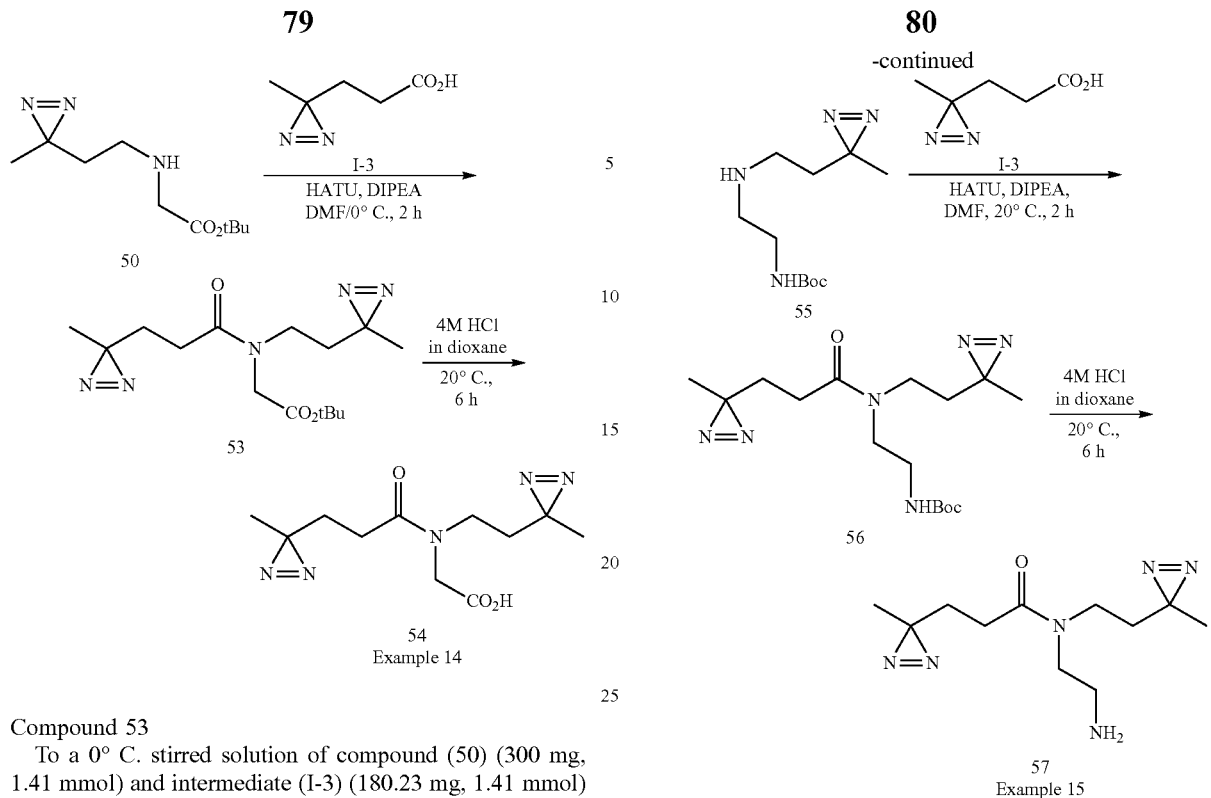

54
Example 14

Compound 53

To a 0° C. stirred solution of compound (50) (300 mg, 1.41 mmol) and intermediate (I-3) (180.23 mg, 1.41 mmol) in DMF (5.00 mL) was added DIPEA (545.38 mg, 4.22 mmol) and HATU (802.24 mg, 2.11 mmol). The mixture was stirred for 2 h at 0° C. before being concentrated under reduced pressure and the residue purified by reverse phase silica gel chromatography using the following conditions: Column, C18 silica gel; mobile phase, A: $NH_4HCO_3$ in water; B: MeCN, detector, UV 200 nm. 0-100% B in 25 min, 50% B to afford compound (53) (200 mg) as light yellow oil.

ESI-MS m/z=324.3[M+H]+.

Compound 54 (Example 14)

To a 0° C. stirred solution compound (53) (200 mg, 0.62 mmol) in 1,4-dioxane was added 4M HCl in 1,4-dioxane. The mixture was stirred for 6 h at 20° C. before being concentrated under reduced pressure and the residue purified by reverse phase silica gel chromatography using the following conditions: Column, C18 silica gel; mobile phase, A: 0.1% formic acid in water; B: MeCN, 10% to 70% gradient in 20 min; detector, UV 200 nm to afford compound (54) (Example 14) (50 mg) as a white solid.

ESI-MS m/z=268.2 [M+H]+, 290.1 [M+Na]+

$^1$H-NMR: (300 MHz, DMSO-d6) δ, ppm, 4.11 (s, 1H), 3.91 (s, 1H), 3.25 (dd, J=15.3, 7.7 Hz, 2H), 2.27 (t, J=7.5 Hz, 1H), 2.08 (dd, J=8.6, 6.3 Hz, 1H), 1.72-1.40 (m, 4H), 1.18-0.55 (m, 6H).

Synthesis of Compound 57 (Example 15)

Example 15 was synthesized according to the scheme below:

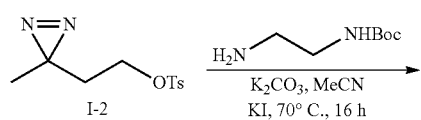

Compound 55

To a 0° C. stirred solution of tert-butyl N-(2-aminoethyl) carbamate (630.03 mg, 3.93 mmol) and intermediate (I-2) (500 mg, 1.97 mmol) in MeCN (20 mL) was added $K_2CO_3$ (543.44 mg, 3.99 mmol) and KI (32.63 mg, 0.2 mmol). The mixture was stirred for 16 h at 70° C. before being concentrated under reduced pressure, diluted with water (20 mL) and extracted with EtOAc (3×20 mL). The combined organic layers were washed with water (20 mL), dried over anhydrous $Na_2SO_4$ and after filtration the filtrate was concentrated under reduced pressure. The residue was purified by silica gel column chromatography, eluted with PE/EtOAc (1:1) to afford compound (55) (280 mg) as a light yellow oil.

ESI-MS m/z=243.3 [M+H]$^+$.

Compound 56

To a 0° C. stirred solution of intermediate (I-3) (148.05 mg, 1.16 mmol) and compound (55) (280 mg, 1.16 mmol) in DMF (2 mL) was added DIPEA (448.01 mg, 3.47 mmol) and HATU (571.15 mg, 1.50 mmol). The mixture was stirred for 2 h at 20° C. before being concentrated under reduced pressure. The residue was purified by reverse phase silica gel chromatography using the following conditions: Column, C18 silica gel; mobile phase, A: $NH_4HCO_3$ in water, B: MeCN, detector, 200 nm, 70% B to afford compound (56) (270 mg) as a colorless oil.

ESI-MS m/z=353.3 [M+H]+.

Compound 57 (Example 15)

4M HCl in 1,4-dioxane (6 mL) was added dropwise to a 0° C. stirred solution of compound (56) (200 mg) in 1,4-dioxane. The mixture was stirred for 6 h at 20° C. before being concentrated under vacuum to afford compound (57) (Example 15) (100 mg) as a colorless oil.

ESI-MS m/z=253.2 [M+H]$^+$.

¹H-NMR: (300 MHz, Methanol-d4): δ, ppm, 3.66-3.54 (m, 2H), 3.46-3.32 (m, 2H), 3.23-3.01 (q, J=7.1, 5.9 Hz, 2H), 2.28 (q, J=7.5 Hz, 2H), 1.81-1.70 (m, 2H), 1.70-1.51 (m, 2H), 1.14-1.01 (m, 6H).

Synthesis of Compound 60 (Example 16)

Example 16 was synthesized according to the scheme below:

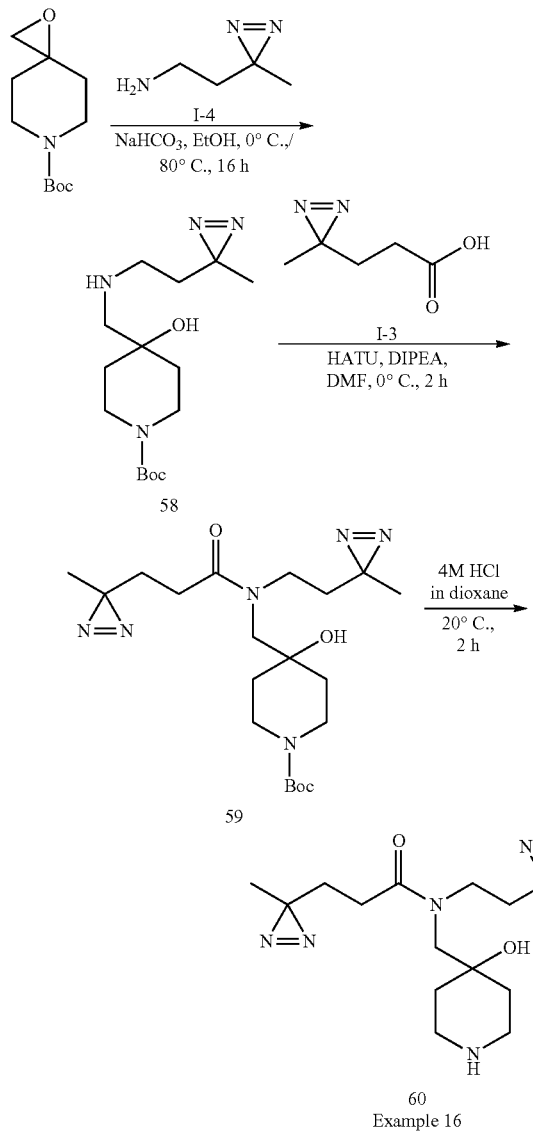

Compound 58

To a 0° C. stirred solution of tert-butyl 1-oxa-6-azaspiro[2.5]octane-6-carboxylate (600 mg, 2.81 mmol) and intermediate (I-4) (278.90 mg, 2.81 mmol) in ethanol (50 mL) was added NaHCO$_3$ (708.88 mg, 8.44 mmol) in portions. The mixture was stirred for 16 h at 80° C. before being concentrated under reduced pressure. The residue was purified by reverse phase silica gel chromatography using the following conditions: Column, C18 silica gel; mobile phase, A: 0.05% formic acid in water; B: MeCN, detector, UV 200 nm, 20% B to afford compound (58) (500 mg) as a yellow oil.

ESI-MS m/z=313.4 [M+H]$^+$.

Compound 59

To a 0° C. stirred solution intermediate (I-3) (236.4 mg, 1.85 mmol) and compound (58) (524 mg, 1.68 mmol) in DMF (5 mL) was added DIPEA (650 mg, 5.04 mmol) and HATU (829.07 mg, 2.18 mmol). The mixture was stirred for 2 h at 0° C. before being concentrated under reduced pressure. The residue was purified by reverse phase silica gel chromatography using the following conditions: Column, C18 silica gel; mobile phase, A: 0.05% formic acid in water, B: MeCN, detector, UV 254 nm, 0-100% B in 30 min to afford compound (59) (300 mg) as a colorless oil.

ESI-MS m/z=445.3 [M+Na]$^+$.

Compound 60 (Example 16)

4M HCl in 1,4-dioxane (4 mL) was added dropwise to a 0° C. stirred solution of compound (59) (200 mg, 0.47 mmol) in MeCN. The mixture was stirred for 2 h at 20° C. before being concentrated under reduced pressure. The residue was purified by reverse phase silica gel chromatography using the following conditions: Column, C18 silica gel; mobile phase, A: 0.05% formic acid in water, B: MeCN, detector, UV 200 nm, 0-100% in 25 min, 20% B to afford compound (60) (Example 16) (100 mg) as a colorless oil.

ESI-MS m/z=323.2 [M+H]$^+$.

¹H-NMR: (400 MHz, Methanol-d4): δ, ppm, 8.56 (s, 1H), 3.52 (q, J=7.6 Hz, 4H), 3.24 (dd, J=7.2, 4.0 Hz, 4H), 2.30 (dt, J=14.6, 7.3 Hz, 2H), 1.76 (td, J=7.6, 3.6 Hz, 6H), 1.69-1.56 (m, 2H), 1.10-1.01 (m, 6H).

Synthesis of Compound 64 (Example 17)

Example 17 was synthesized according to the scheme below:

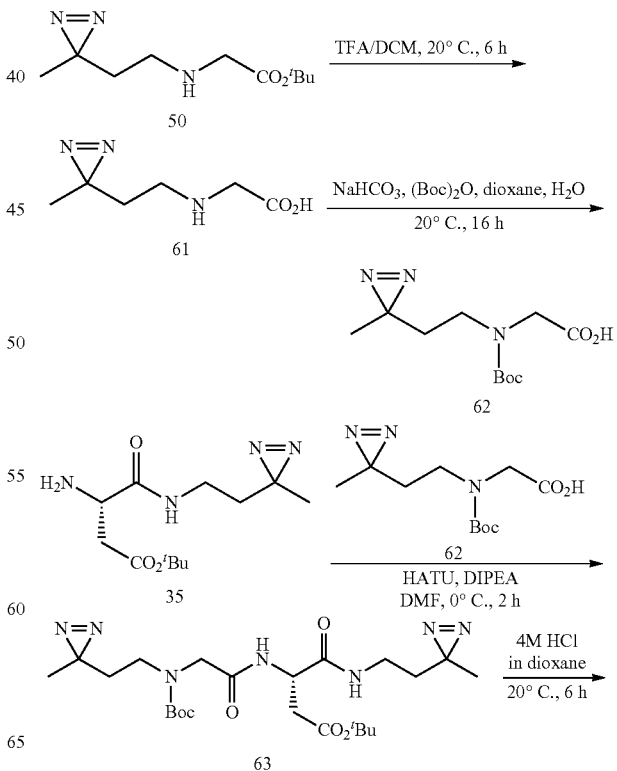

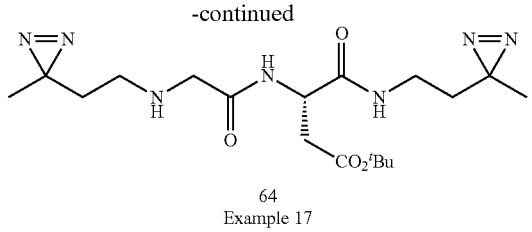

64
Example 17

Compound 61

To a stirred solution of compound (50) (750 mg) in DCM (15 mL) was added TFA (15 mL) at 20° C. The mixture was stirred for 6 h at 20° C. before being concentrated under reduced pressure to afford compound (61) which was used for the next steps without further purification.

ESI-MS m/z=158.2 [M+H]⁺.

Compound 62

To a 0° C. stirred solution of compound (61) (750 mg, 0.48 mol) in 1,4-dioxane (10 mL) and saturated aqueous NaHCO₃ (10 mL) was added di-tert-butyl dicarbonate (2.3 g, 10.75 mmol) in portions. The resulting mixture was stirred for 16 h at 20° C. before being neutralized to pH 6-7 with 1M HCl. The aqueous layer was extracted with EtOAc (3×50 mL), the combined organic layers were washed with water (3×50 mL), saturated brine (100 mL) and dried over anhydrous Na₂SO₄. After filtration, the filtrate was concentrated under reduced pressure and the residue purified by reverse phase silica gel chromatography using the following conditions: Column, C18 silica gel; mobile phase, A: 0.05% formic acid in water; B: MeCN, 0%-100% gradient in 30 min, UV 200 nm to afford compound (62) (250 mg) as a light yellow oil.

ESI-MS m/z=258.2 [M+H]⁺.

Compound 63

To a 0° C. stirred solution of compound (62) (237.94 mg, 0.93 mmol) and compound (35) (250 mg, 0.93 mmol) in DMF (5 mL) was added DIPEA (358.57 mg, 2.77 mmol) and HATU (457.12 mg, 1.2 mmol) in portions. The mixture was stirred for 2 h at 20° C. before being concentrated under reduced pressure and the residue purified by reverse phase silica gel chromatography using the following conditions: Column, C18 silica gel; mobile phase, A: 0.05% formic acid in water; B: MeCN, 0% to 100% gradient in 30 min; detector, UV 200 nm to afford compound (63) (380 mg) as a light yellow oil.

ESI-MS m/z=510.3 [M+H]⁺.

Compound 64 (Example 17)

4M HCl in 1,4-dioxane (3 mL) was added dropwise to a 0° C. stirred solution of compound (63) (200 mg, 0.39 mmol) in 1,4-dioxane. The mixture was stirred for 6 h at 20° C. before being concentrated under reduced pressure. The residue was purified by reverse phase silica gel chromatography using the following conditions: Column, C18 silica gel; mobile phase, A: 0.05% acetic acid in water; B: MeCN, 20% B to afford compound (64) (Example 17) (75 mg) as a white solid.

ESI-MS m/z=354.2 [M+H]⁺.

¹H-NMR: (400 MHz, Methanol-d4): δ, ppm, 4.69 (dd, J=7.6, 5.5 Hz, 1H), 3.64-3.51 (m, 2H), 3.17 (h, J=6.5 Hz, 2H), 2.84-2.58 (m, 4H), 1.60 (dt, J=43.4, 7.6 Hz, 2H), 1.55 (dt, 2H), 1.06 (d, J=12.6 Hz, 6H).

Synthesis of Compound 68 (Example 18)

Example 18 was synthesized according to the scheme below:

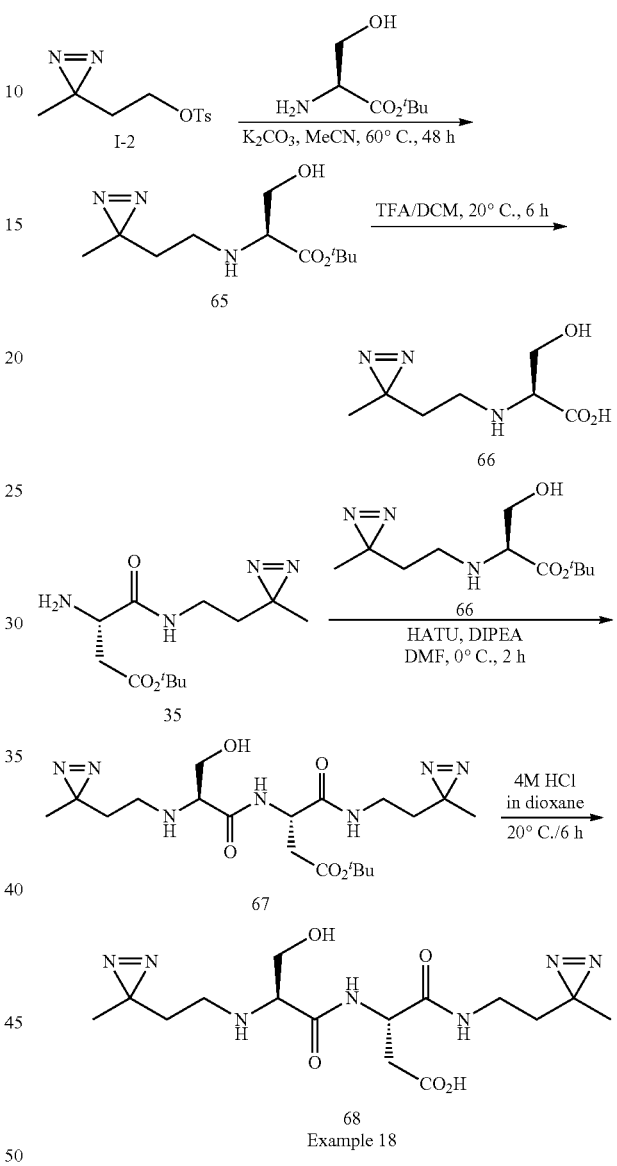

68
Example 18

Compound 65

To a 0° C. stirred solution of intermediate (I-2) (1 g, 3.93 mmol) and tert-butyl (2S)-2-amino-3-hydroxypropanoate (633.9 mg, 3.93 mmol) in MeCN (100 mL) was added K₂CO₃ (1.09 g, 7.86 mmol). The mixture stirred for 48 h at 60° C. before being concentrated under reduced pressure, diluted with water (100 mL) and extracted with EtOAc (3×100 mL). The combined organic layers were washed with water (2×200 mL), dried over anhydrous Na₂SO₄ and after filtration, the filtrate concentrated under reduced pressure. The residue was purified by reverse phase silica gel chromatography using the following conditions: Column, C18 silica gel; mobile phase, A: 0.05% formic acid in water; B: MeCN, 10% to 90% gradient in 25 min; detector, UV 200 nm. to afford compound (65) (0.50 g) as a yellow oil.

ESI-MS m/z=244.4 [M+H]+.

Compound 66

TFA (15 mL) was added dropwise to a 0° C. stirred solution of compound (65) (0.50 g, 2.05 mmol) in DCM (15 mL). The mixture stirred for 6 h at 20° C. before being concentrated under reduced pressure to afford compound (66) which was used for the next step without further purification.

ESI-MS m/z=188.2 [M+H]+.

Compound 67

To a 0° C. stirred solution of compound (66) (55.38 mg, 0.3 mmol) and compound (35) (80 mg, 0.3 mmol) in DMF (2 mL) was added DIPEA (114.74 mg, 0.89 mmol) and HATU (146.28 mg, 0.39 mmol). The mixture was stirred for 2 h at 0° C. before being concentrated under reduced pressure and the residue purified by reverse phase silica gel chromatography using the following conditions: Column, C18 silica gel; mobile phase, A: 0.05% formic acid in water; B: MeCN, 10% to 50% gradient in 20 min; detector, UV 200 nm to afford compound (67) (70 mg) as a white solid.

ESI-MS m/z=440.2 [M+H]+.

Compound 68 (Example 18)

4M HCl in 1,4-dioxane (2 mL) was added dropwise to a stirred solution of compound (67) (70 mg, 0.16 mmol) at 20° C. The mixture was stirred for 6 h at 20° C. before being concentrated under reduced pressure. The residue was purified by reverse phase silica gel chromatography using the following conditions: Column, C18 silica gel; mobile phase, A: 0.05% formic acid in water; B: 10% to 90% gradient in 25 min; detector, UV 200 nm, 15% B to afford compound (68) (Example 18) (51 mg) as a white solid.

ESI-MS m/z=384.2 [M+H]+.

1H-NMR: (300 MHz, DMSO-d6): δ, ppm, 8.23 (d, J=8.5 Hz, 1H), 7.87 (t, J=5.7 Hz, 1H), 5.01 (s, 1H), 4.70-4.40 (m, 1H), 3.47 (d, J=6.3 Hz, 2H), 3.09 (t, J=6.2 Hz, 1H), 2.99 (q, J=6.7 Hz, 2H), 2.69 (dd, J=16.4, 5.5 Hz, 1H), 2.62-2.51 (m, 1H), 2.37 (ddt, J=23.5, 12.0, 6.3 Hz, 2H), 1.60-1.32 (m, 4H), 1.00 (s, 6H).

Synthesis of Compound 73 (Example 19)

Example 19 was synthesized according to the scheme below:

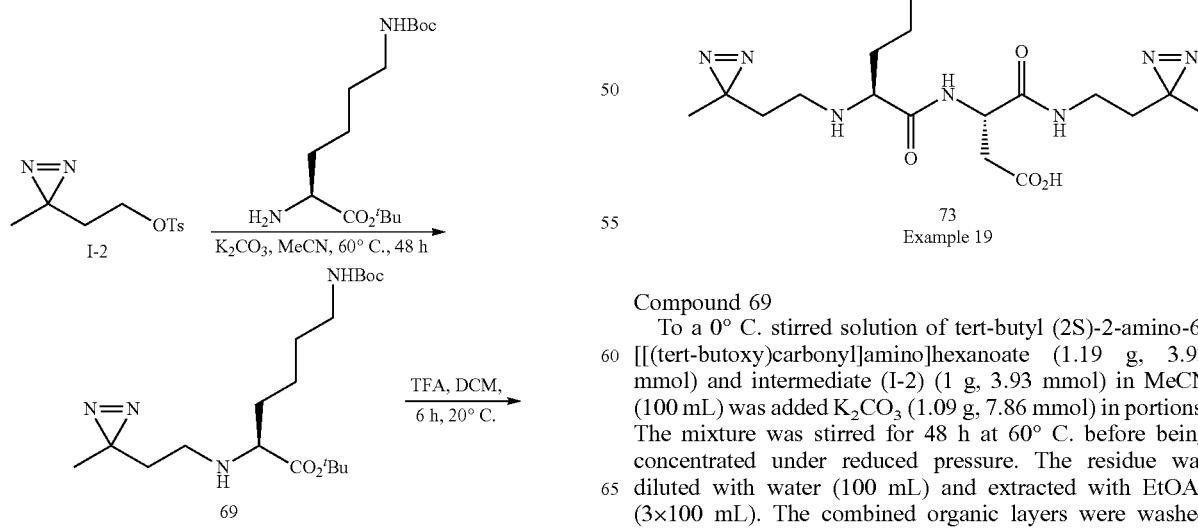

Compound 69

To a 0° C. stirred solution of tert-butyl (2S)-2-amino-6-[[(tert-butoxy)carbonyl]amino]hexanoate (1.19 g, 3.93 mmol) and intermediate (I-2) (1 g, 3.93 mmol) in MeCN (100 mL) was added K2CO3 (1.09 g, 7.86 mmol) in portions. The mixture was stirred for 48 h at 60° C. before being concentrated under reduced pressure. The residue was diluted with water (100 mL) and extracted with EtOAc (3×100 mL). The combined organic layers were washed with water (2×200 mL), dried over anhydrous Na2SO4 and after filtration, the filtrate was concentrated under reduced pressure. The residue was purified by silica gel column chromatography, eluted with PE/EtOAc (5:1 to 3:1) to afford compound (69) (1 g) as a light yellow oil.

ESI-MS m/z=385.2 [M+H]$^+$.

Compound 70

TFA (30 mL) was added dropwise to a 0° C. stirred solution of compound (69) (570 mg) in DCM (30 mL). The mixture was stirred for 6 h at 20° C. before being concentrated under reduced pressure to afford (compound 70) which was used for the next step without further purification.

ESI-MS m/z=229.2 [M+H]+.

Compound 71

To a 0° C. stirred solution of compound (70) (1 g, 4.38 mmol) in 1,4-dioxane (30 mL) was added saturated aqueous NaHCO$_3$ (30 mL) and di-tert-butyl dicarbonate (955.98 mg, 4.38 mmol) in portions. The resulting mixture was stirred for 16 h at 25° C. before being neutralized to pH 6-7 with 1M HCl. The aqueous layer was extracted with EtOAc (3×50 mL) and the combined organic layers washed with water (2×100 mL), dried over anhydrous Na$_2$SO$_4$ and after filtration, the filtrate was concentrated under reduced pressure. The residue was purified by reverse phase silica gel chromatography using the following conditions: Column, C18 silica gel; mobile phase, A: 0.05% formic acid in water; B: MeCN, 10% to 50% gradient in 20 min; detector, UV 200 nm to afford compound (71) (200 mg) as a light yellow oil.

ESI-MS m/z=329.3 [M+H]$^+$.

Compound 72

To a 0° C. stirred solution of compound (71) (170 mg, 0.52 mmol) and compound (35) (153.93 mg, 0.57 mmol) in DMF (3 mL) were added HATU (236.19 mg, 0.62 mmol) and DIPEA (200.7 mg, 1.55 mmol) in portions. The mixture was stirred for 2 h at 0° C. before being concentrated under reduced pressure. The residue was purified by reverse phase silica gel chromatography using the following conditions: Column, C18 silica gel; mobile phase, A: 0.05% formic acid in water; B: MeCN, 10% to 80% gradient in 20 min; detector, UV 200 nm to afford compound (72) (100 mg) as a light yellow oil.

ESI-MS m/z=581.6 [M+H]$^+$.

Compound 73 (Example 19)

4M HCl in 1,4-dioxane (4 mL) was added dropwise to a 20° C. stirred solution of compound (72) (100 mg, 0.17 mmol) in 1,4-dioxane. The mixture was stirred for 6 h at 20° C. before being concentrated under reduced pressure. The residue was purified by preparative HPLC using the following conditions: Column: SunFire C18 OBD Prep Column, 100 Å, 5 μm, 19 mm×250 mm; Mobile Phase A: Water (0.1% formic acid), Mobile Phase B: MeCN; Flow rate: 25 mL/min; Gradient: 1% B to 1% B in 7 min; 200 nm; Rt: 5.6 min) to afford compound (73) (Example 19) (34.6 mg) as a white solid.

ESI-MS m/z=425.25 [M+H]$^+$.

$^1$H-NMR (300 MHz, Methanol-d4): δ, ppm, 4.72 (dd, J=8.7, 4.9 Hz, 1H), 3.56 (s, 1H), 3.29-3.03 (m, 2H), 2.97 (t, J=7.1 Hz, 2H), 2.86 (m, 4H), 1.89-1.75 (m, 2H), 1.77-1.44 (m, 8H), 1.06 (d, J=5.6 Hz, 6H).

Synthesis of Compound 75 (Example 20)

Example 20 was synthesized according to the scheme below:

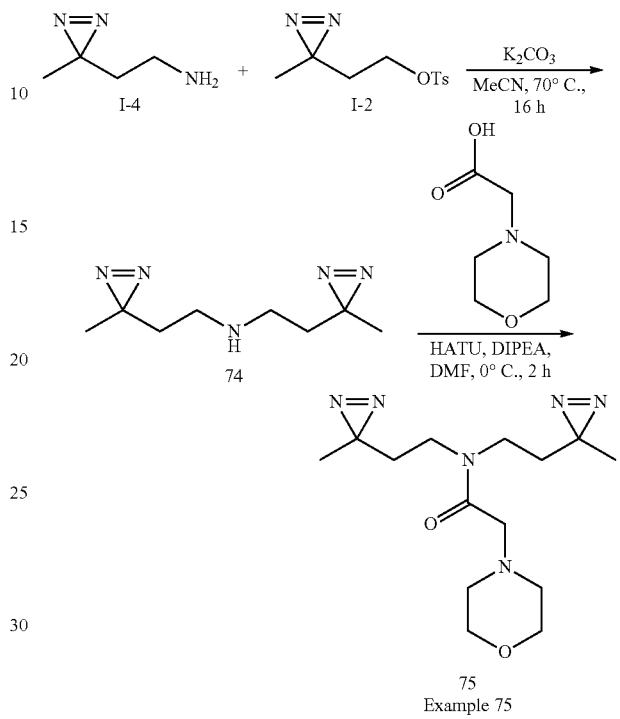

75
Example 75

Compound 74

To a room temperature stirred solution of intermediate (I-2) (1.41 g, 5.55 mmol) in MeCN (20 mL) was added intermediate (I-4) (500 mg, 5.04 mmol) and K$_2$CO$_3$ (2.11 g, 15.13 mmol) in portions. The mixture was stirred for 16 h at 70° C. and after cooling to room temperature concentrated under reduced pressure. The residue was diluted with water (100 mL) and extracted with EtOAc (3×100 mL). The combined organic layers were washed with water (2×200 mL), dried over anhydrous Na$_2$SO$_4$ and after filtration, the filtrate was concentrated under reduced pressure to afford compound (74) which was used for the next step without further purification.

ESI-MS m/z=182.2 [M+H]$^+$.

Compound 75 (Example 20)

To a 0° C. stirred solution of morpholin-4-ylacetic acid (286.47 mg, 1.97 mmol) in DMF (2 mL) was added compound (74) (300 mg, 1.79 mmol), DIPEA (695.62 mg, 5.38 mmol) and HATU (886.82 mg, 2.33 mmol) in portions. The mixture was stirred for 2 h at 0° C. before being concentrated under reduced pressure. The residue was purified by preparative HPLC using the following conditions (Column: XBridge Prep OBD C18 Column 19×250 mm, 5 μm; Mobile Phase A: Water (10 mmol/L NH$_4$HCO$_3$), Mobile Phase B: MeCN; Flow rate: 25 mL/min; Gradient: 32% B to 40% B in 12 min; 220/200 nm; Rt: 9.98 min) to afford compound (75) (Example 20) (16.6 mg) as a colorless oil.

ESI-MS m/z=309.15 [M+H]$^+$.

¹H-NMR: (400 MHz, Methanol-d4): δ, ppm, 3.79-3.65 (m, 4H), 3.48-3.38 (m, 2H), 3.31 (s, 2H), 3.23 (s, 2H), 2.51 (t, J=4.7 Hz, 4H), 1.73-1.63 (m, 2H), 1.58-1.48 (m, 2H), 1.08 (s, 3H), 1.05 (s, 3H).

Synthesis of Compound 78 (Example 21)

Example 21 was synthesized according to the scheme below:

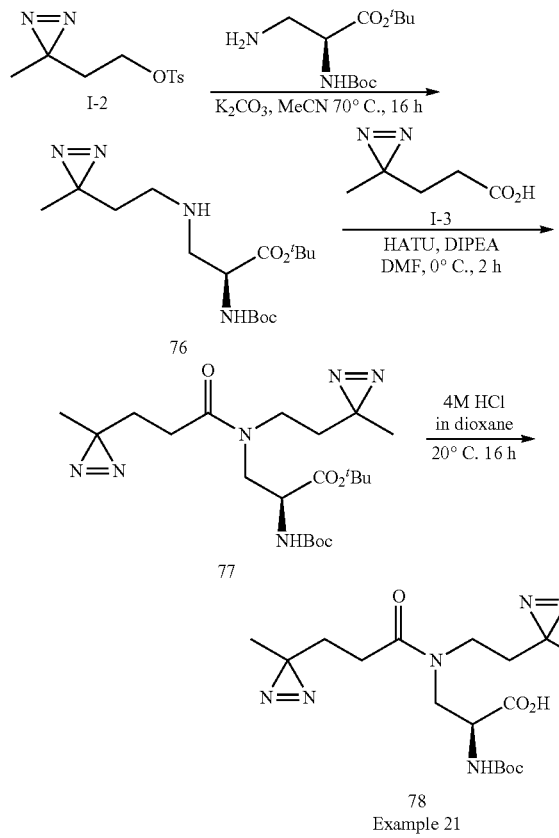

Compound 76

To a room temperature stirred solution of intermediate (I-2) (500 mg, 1.967 mmol) in MeCN (10 mL) was added tert-butyl (2S)-3-amino-2-[(tert-butoxycarbonyl)amino]propanoate (511.86 mg, 1.97 mmol) and K₂CO₃ (815.21 mg, 5.9 mmol) in portions. The mixture was stirred for 16 h at 70° C. before being allowed to cool to room temperature and concentrated under reduced pressure. The residue was diluted with water (50 mL) and the aqueous layer extracted with EtOAc (3×50 mL). The combined organic layers were washed with water (2×100 mL), dried over anhydrous Na₂SO₄ and after filtration, the filtrate concentrated under reduced pressure to afford compound (76) which was used in the next step without further purification.

ESI-MS m/z=343.5 [M+H]⁺.

Compound 77

To a 0° C. stirred solution of compound (76) (800 mg, 2.34 mmol) in DMF (5 mL) was added intermediate (I-3) (329.27 mg, 2.57 mmol), DIPEA (905.8 mg, 7.01 mmol) and HATU (1065.94 mg, 2.80 mmol) in portions. The mixture was stirred for 2 h at 0° C. before being concentrated under reduced pressure and the residue purified by reverse phase silica gel chromatography using the following conditions: Column, C18 silica gel; mobile phase A: 0.1% formic acid in water, mobile phase B: MeCN; 0% to 100% gradient in 30 min; detector, UV 220 nm, 70% B to afford compound (77) (200 mg) as a colorless oil.

ESI-MS m/z=453.4 [M+H]⁺.

Compound 78 (Example 21)

4M HCl in 1,4-dioxane (20 mL) was added to a 20° C. solution of compound (77) (200 mg, 0.44 mmol) in 1,4-dioxane. The mixture was stirred for 6 h at 20° C. before being concentrated under reduced pressure. The residue was purified by reverse phase silica gel chromatography using the following conditions: Column, C18 silica gel; mobile phase, A: 0.1% formic acid in water, B: MeCN; detector, UV 200 nm, 10% to 100% gradient in 30 min, 20% B to afford compound (78) (Example 21) (40.1 mg) as a white solid.

ESI-MS m/z=297.15 [M+H]⁺.

¹H-NMR (300 MHz, DMSO-d6): δ, ppm, 7.89 (d, J=6.9 Hz, 1H), 4.12 (p, J=6.8, 6.4 Hz, 1H), 2.99 (dd, J=11.8, 5.8 Hz, 1H), 2.85-2.67 (m, 3H), 2.09 (t, J=7.7 Hz, 2H), 1.64-1.47 (m, 4H), 1.01 (d, J=10.1 Hz, 6H).

Synthesis of Compound 81 (Example 22)

Example 22 was synthesized according to the scheme below:

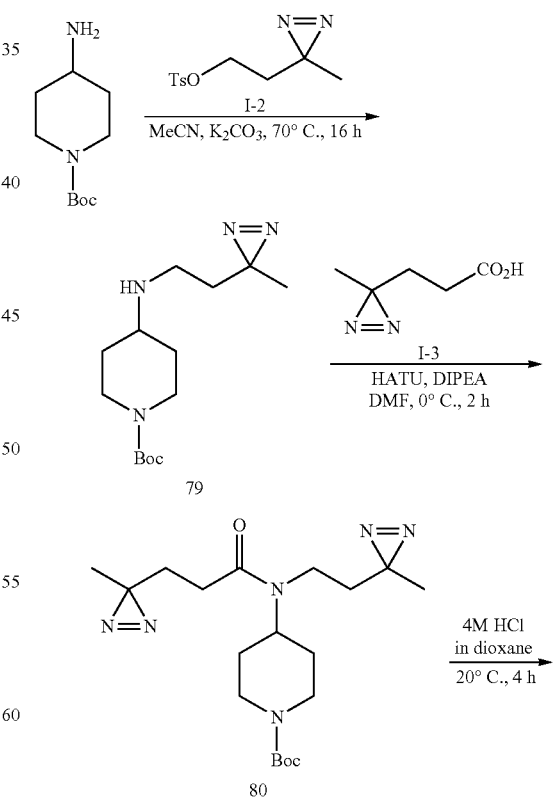

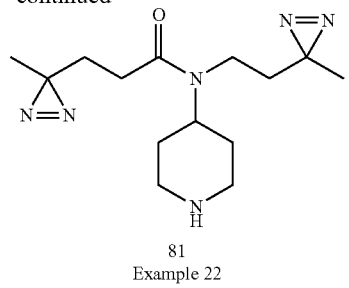

81
Example 22

Compound 79

To a room temperature stirred solution of intermediate (I-2) (507.88 mg, 2.0 mmol) in MeCN (40 mL) was added tert-butyl 4-aminopiperidine-1-carboxylate (400 mg, 2.0 mmol) and $K_2CO_3$ (828.07 mg, 5.99 mmol) in portions. The mixture was stirred for 16 h at 70° C. before being cooled to room temperature and concentrated under reduced pressure.

The residue was diluted with water (50 mL) and extracted with EtOAc (3×50 mL). The combined organic layers were washed with water (2×100 mL), dried over anhydrous $Na_2SO_4$ and after filtration, the filtrate was concentrated under reduced pressure to afford compound (79) which was used in the next step without further purification.

ESI-MS m/z=283.3 $[M+H]^+$.

Compound 80

To a 0° C. stirred solution of compound (79) (600 mg, 2.13 mmol) in DMF (5 mL) was added intermediate (I-3) (299.47 mg, 2.34 mmol), DIPEA (823.82 mg, 6.37 mmol) and HATU (1.05 g, 2.76 mmol) in portions. The mixture was stirred for 2 h at 0° C. before being concentrated under reduced pressure. The residue was purified by reverse phase silica gel chromatography using the following conditions: Column, C18 silica gel; mobile phase, A: 0.1% formic acid in water, B: 0% to 100% gradient in 30 min; detector, UV 220 nm, 60% to afford compound (80) (300 mg) as a colorless oil.

ESI-MS m/z=415.3 $[M+Na]^+$

Compound 81 (Example 22)

4M HCl in 1,4-dioxane (20 mL) was added dropwise to room temperature solution of compound (80) (300 mg) and stirred for 4 h at 20° C. The mixture was concentrated under reduced pressure and the residue purified by reverse phase silica gel chromatography using the following conditions: Column, C18 silica gel; mobile phase, A: 0.1% formic acid in water, B: MeCN, detector, UV 220 nm, 0% to 100% gradient in 30 min, 20% to afford compound (81) (Example 22) (200 mg) as a colorless oil.

ESI-MS m/z=293.2 $[M+H]^+$ $^1$H-NMR (300 MHz, Methanol-d4): δ, ppm, 8.55 (s, 1H), 4.12-3.95 (m, 1H), 3.51-3.39 (m, 2H), 3.31-3.18 (m, 2H), 3.16-2.95 (m, 2H) 2.37-2.25 (m, 1H), 2.25-2.09 (m, 2H), 2.01-1.81 (m, 3H), 1.73 (q, J=7.3 Hz, 2H), 1.69-1.48 (m, 2H), 1.14-0.99 (m, 6H).

Synthesis of Compound 84 (Example 23)

Example 23 was synthesized according to the scheme below:

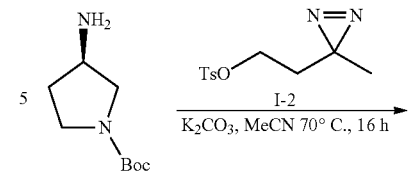

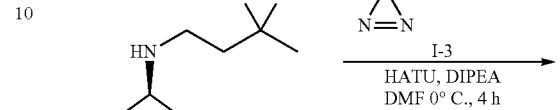

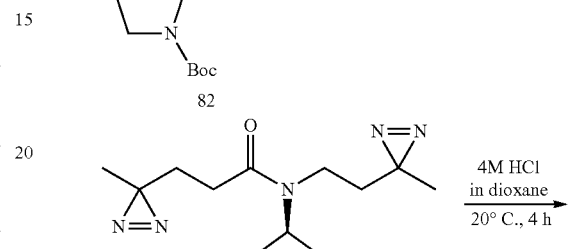

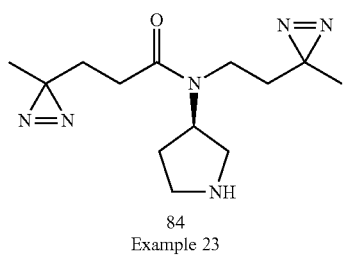

84
Example 23

Compound 82

To a room temperature stirred solution of intermediate (I-2) (600.75 mg, 2.36 mmol) in MeCN (40 mL) was added tert-butyl (3R)-3-aminopyrrolidine-1-carboxylate (400 mg, 2.15 mmol) and $K_2CO_3$ (890.43 mg, 6.44 mmol) in portions. The mixture was stirred for 16 h at 70° C. before being cooled down to room temperature and concentrated under reduced pressure. The residue was diluted with water (100 mL) and extracted with EtOAc (3×50 mL). The combined organic layers were washed with water (2×100 mL), dried over anhydrous $Na_2SO_4$ and after filtration, the filtrate concentrated under reduced pressure to afford compound (82) which was used in the next step without further purification.

ESI-MS m/z=257.1 $[M+H]^+$.

Compound 83

To a 0° C. stirred solution of intermediate (I-3) (315.12 mg, 2.46 mmol) in DMF (5 mL) was added compound (82) (600 mg, 2.24 mmol), DIPEA (866.88 mg, 6.71 mmol) and HATU (1105.15 mg, 2.91 mmol) in portions. The mixture was stirred for 16 h at 0° C. before being concentrated under reduced pressure. The residue was purified by reverse phase silica gel chromatography using the following conditions: Column, C18 silica gel; mobile phase, A: 0.1% formic acid in water, B: MeCN; detector, UV 220 nm, 0% to 100% gradient in 30 min, 70% to afford compound (83) (200 mg) as a colorless oil.

ESI-MS m/z=412.9 $[M+H]^+$.

Compound 84 (Example 23)

4M HCl in 1,4-dioxane (15 mL) was added to a 20° C. solution of compound (83) (200 mg, 0.53 mmol) in 1,4-dioxane. The mixture was stirred for 4 h at 20° C. before being concentrated under reduced pressure. The residue was purified by reverse phase silica gel chromatography using the following conditions: Column, C18 silica gel; mobile phase, A: 0.1% formic acid in water, B: MeCN; detector, UV 254 nm, 0% to 100% gradient in 30 min, 20% to afford compound (84) (Example 23) (100 mg) as a light yellow oil.

ESI-MS m/z=279.20 [M+H]$^+$ $^1$H-NMR: (300 MHz, Methanol-d4): δ, ppm, 8.56 (s, 1H), 4.27-3.89 (m, 1H), 3.81-3.62 (m, 1H), 3.54-3.43 (dd, J=12.4, 3.6 Hz, 1H), 3.42-3.35 (t, J=7.7 Hz, 4H), 3.21-3.07 (m, 1H), 2.41 (m, 1H), 2.30-2.10 (m, 3H), 1.84-1.72 (m, 2H), 1.71-1.51 (m, 2H), 1.11 (s, 3H), 1.04 (s, 3H).

Methods for Evaluating Compounds:

Porcine Eye Corneal Flattening Assay

Porcine whole globes in saline at 4° C. were warmed to room temperature. The corneas were then de-epithelialized with a dulled scalpel blade and the eyes placed into custom movable eye holders in a horizontal position with the cornea facing upward. The eye holders were then positioned inside an enclosed chamber that allows for the control of atmosphere, temperature and humidity (typically a water bath at 37.0° C.). IOP is maintained at a constant pressure by the insertion of a blood bank buffered saline line from an IV bag at a standard height inserted into each eye via a syringe needle. 5% Dextran T500 in blood bank buffered saline is dropped onto the surface of the cornea of each eye every 90 sec for 2 hours to allow the eyes to stabilize. The dextran drops were discontinued and a solution of a test compound held in place by a small rubber O-ring on the center of the cornea is allowed to soak into the corneal surface of the test eye. After a set soaking time (typically 10 minutes) the O-ring is removed and any excess test solution washed away with saline. The test eye is then orientated in a vertical position and the pre-treatment surface keratometry of the cornea measured using a Pentacam® HR device fine cornea 100 scan. The eye is then returned to the horizontal position and a specific pattern of UVA light at 365 nm is administered to the cornea over a desired dosing period. After a further 1.5 hours during which the 5% dextran drops are resumed the eye is orientated back to the vertical position and the post-treatment surface keratometry of the cornea measured using a Pentacam® HR device fine cornea 100 scan as before. The difference map between the pre and post treatment corneal images is obtained and the overall change in keratometry (Km) of the central 3 mm zone recorded as a change in diopters.

The following notes provide further clarification regarding certain steps in the assay:

(1) After warming the porcine globes in saline to room temperature, eyes were either immediately placed into custom movable eye holders with the cornea facing upward or were first de-epithelialized with a dulled scalpel blade before being placed in the holder.

(2) IOP as used herein refers to "intra ocular pressure". IOP was maintained by inserting a blood bank buffered saline line from an IV bag at a standard height into each eye via a needle.

(3) 0.5% to 10% (typically 5%) Dextran T500 in blood bank buffered saline was dropped onto the cornea of each eye every 90 sec for 2 hours to allow the eyes to stabilize. The test eye is then orientated in a vertical position and a pre-treatment surface keratometry scan of the cornea taken using a Pentacam® HR device (fine cornea 100 scan). The eye is then returned to the horizontal position and the dextran drops replaced by a solution of the test compound (typically 0.22% w/v in saline) held in place by a small rubber O-ring on the center of the cornea.

(4) After a set soaking time 5-30 minutes (typically 10 minutes) the O-ring is removed and excess test solution washed away with saline.

Representative porcine corneal flattening data* for selected examples of the present disclosure are listed in Table B-1, below:

TABLE B-1

| Example # | Compound # | Refractive Change (D) |
|---|---|---|
| 1 | Compound 2 | −0.32 |
| 10 | Compound | −0.64 |

*UVA light administered in a 4 mm circle at 365 nm, 30 mW/cm$^2$ irradiance, continuous wave (CW), for 8.1 min, 15 J total dose under a normal (21% O$_2$) atmosphere at 37.0° C.

Porcine Eye Corneal Stiffening Assay

Porcine whole globes in saline at 4° C. were warmed to room temperature. The eyes were either immediately placed into custom movable eye holders in a horizontal position with the cornea facing upward or were first de-epithelialized with a dulled scalpel blade before being placed in the holder. The eye holders were then positioned inside an enclosed chamber that allows for the control of atmosphere, temperature and humidity (typically a water bath at 37.0° C.). A solution of test compound held in place by a small rubber O-ring on the center of the cornea is then allowed to soak into the cornea surface of the test eye. After a set soaking time (typically 10 minutes) the O-ring is removed and any excess test solution washed away with saline. A specific pattern of UVA light at 365 nm is administered to the test eye cornea over a desired dosing period. A corneal flap of desired thickness (typically 200 μm is then excised from the eyes using a femtosecond laser (Zeimer, LDV1). The corneal flap is placed in saline at ambient temperature for 20 minutes and then mounted onto a biaxial extensiometer (CellScale Biotester5000, Waterloo, ON), using biorake attachments (5 tines spanning a width of 3.5 mm). The corneal flap is stretched at a constant rate of 4 μm/s in saline at 37° C. until sample failure. The maximum slope of the force vs distance curve is calculated and compared to that obtained from an untreated cornea.

The following notes provide further clarification regarding certain steps in the assay:

(1) A solution of the test compound (typically 0.22% w/v in saline) is held in place by a small rubber O-ring on the center of the cornea is then allowed to soak into the cornea surface of the test eye. After a set soaking time of 5-30 minutes (typically 10 minutes) the O-ring is removed and any excess test solution washed away with saline.

(2) A corneal flap of desired thickness and diameter (typically 200 μm thick by 8 mm diameter) is then excised from the eyes using a femtosecond laser (Zeimer, LDV1). The corneal flap is either placed in saline at ambient temperature for 20 minutes and then mounted in saline onto a biaxial extensiometer (CellScale Biotester5000, Waterloo, ON) or mounted directly onto the tester in 5% Dextran T500/saline.

(3) Biorake attachments (5 tines spanning a width of 3.5 mm) are used to hold the flap as it is stretched at 37° C.

and a constant rate of 4 μm/s in both X (5 N load cell) and Y (10 N load cell) directions simultaneously.

(4) The maximum slope of the force vs distance curve corresponds to the stiffening value. It is compared to that obtained from an untreated cornea.

Representative porcine stiffening data** for selected examples of the present disclosure are listed in Table C-1, below:

TABLE C-1

| Example # | Name/ID # | Max slope |
|---|---|---|
| 1 | Compound 2 | 11.28 |
| 6 | Compound 25 | 10.88# |
| 10 | Compound 43 | 10.14# |
| 13 | Compound 52 | 12.38 |
| 14 | Compound 54 | 10.5#, 10.66 |
| 17 | Compound 64 | 10.13 |
| 23 | Compound 84 | 10.68# |

**UVA light administered in a 9 mm circle at 365 nm, 30 mW/cm² irradiance, continuous wave (CW), for 8.1 min, 15 J total dose under a normal (21% O₂) atmosphere at 37.0° C. Untreated cornea max slope value = 10.1
eyes were not de-epithelialized prior to treatment.

A number of embodiments of the invention have been described. Nevertheless, it will be understood that various modifications may be made without departing from the spirit and scope of the invention. Accordingly, other embodiments are within the scope of the following claims

What is claimed is:
1. A compound of Formula II

$$\text{(II)}$$

or a pharmaceutically acceptable salt thereof, wherein:
   each of $B^1$ and $B^2$ is independently —$Z^1$—$Z^2$—$Z^3$, wherein:
      $Z^1$ is $C_{1-3}$ alkylene;
      $Z^2$ is a bond; and
      $Z^3$ is H;
   each of $E^1$ and $Q^1$ is $C_1$-$C_6$ alkylene, which is optionally substituted with 1-3 $R^a$;
   each occurrence of $R^2$ is independently selected from the group consisting of:
      (i) $R^a$;
      (ii) $C_1$-$C_6$ alkyl, which is substituted with 1-3 $R^a$;
      (iii) $L^2$-heterocyclyl, wherein the heterocyclyl includes from 3-10 ring atoms, wherein from 1-3 ring atoms are heteroatoms, each independently selected from the group consisting of N($R^d$), O, and S; and wherein one or more of the heterocyclyl ring carbon atoms are optionally substituted with from 1-4 independently selected $R^b$,
      (iv) $L^2$-$C_6$-$C_{10}$ aryl, which is optionally substituted with from 1-4 $R^c$;
      (v) $L^2$-heteroaryl, wherein the heteroaryl includes from 5-10 ring atoms, wherein from 1-4 ring atoms are heteroatoms, each independently selected from the group consisting of N, N($R^d$), O, and S, and wherein one or more of the heteroaryl ring carbon atoms are optionally substituted with from 1-4 independently selected $R^c$; and
      (vi) H; or
      (vii) $R^2$ and $R^{d1}$, in the —C(=O)CH($R^2$)N($R^{d1}$)— group, combine to form a ring including from 5-8 ring atoms, wherein the ring includes: (a) from 3-6 ring carbon atoms (in addition to CH($R^2$)), each of which is substituted with from 1-2 substituents independently selected from H and $C_{1-3}$ alkyl; and (b) from 0-3 ring heteroatoms (in addition to the nitrogen atom attached to $R^{d1}$), which are each independently selected from the group consisting of N($R^{d1}$), O, and S;
   each occurrence of $R^a$ is independently selected from the group consisting of: —OH; —SH; —F; —Cl; —Br; —NR$^e$R$^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R"); —S(O)$_{1-2}$(NR'R"); —S(O)$_{0-2}$($C_{1-4}$ alkyl); cyano; —NR'C(=NR')NR'R"; and $C_{3-6}$ cycloalkyl optionally substituted with from 1-4 independently selected $R^b$;
   each occurrence of $R^b$ is independently selected from the group consisting of: —OH; —SH; —F; —Cl; —Br; —NR$^e$R$^f$; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R"); oxo; —S(O)$_{1-2}$(NR'R"); —S(O)$_{0-2}$($C_{1-4}$ alkyl); cyano; —NR'C(=NR')NR'R"; and $C_{3-6}$ cycloalkyl optionally substituted with from 1-4 independently selected $C_{1-4}$ alkyl;
   each occurrence of $R^c$ is independently selected from the group consisting of: —OH; —SH; —F; —Cl; —Br; —NR$^e$R$^f$; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R"); —S(O)$_{1-2}$(NR'R"); —S(O)$_{0-2}$($C_{1-4}$ alkyl); cyano; —NR'C(=NR')NR'R"; and $C_{3-6}$ cycloalkyl optionally substituted with from 1-4 independently selected $C_{1-4}$ alkyl;
   each occurrence of $R^d$ is selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R"); —S(O)$_{1-2}$(NR'R"); —S(O)$_{1-2}$($C_{1-4}$ alkyl); —OH; and $C_{1-4}$ alkoxy;
   each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R"); —S(O)$_{1-2}$(NR'R"); —S(O)$_{1-2}$($C_{1-4}$ alkyl); —OH; and $C_{1-4}$ alkoxy; and
   each occurrence of R' and R" is independently selected from the group consisting of: H and $C_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R"), which are each independently selected from the group consisting of N($R^4$), O, and S;
   each occurrence of $R^{d1}$ is selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R')(R"); —S(O)$_{1-2}$(NR'R"); —S(O)$_{1-2}$($C_{1-4}$ alkyl); —OH; and $C_{1-4}$ alkoxy; or $R^2$ and $R^{d1}$, in the —C(=O)CH (R²)N(R^{d1})— group, combine to form a ring including from 5-8 ring atoms as defined above;

each of L² in each occurrence is independently a single bond or a $C_1$-$C_6$ alkylene optionally substituted with 1-3 substituents independently selected from oxo and R^a; and F¹ is —N(R^{d1})—, —O—, or —S—; and each of H¹, G¹, L¹, and M¹ is independently selected from:
a bond;
—N(R^{d1})—,
—O—;
$S(O)_p$, wherein p is 0, 1, or 2;
C(=O);
C(=S);
CHR₂;
—C(=O)CH(R²)N(R^{d1})—; and
—C(=O)CH(R²)CH₂N(R^{d1})—.

2. The compound according to claim 1, wherein each of L¹ and M¹ is a bond; each of G¹ and H¹ is a bond; and F¹ is —N(R⁴)— or —O—.

3. The compound according to claim 1, wherein each occurrence of R² independently is selected from:
H;
$C_1$-$C_6$ alkyl optionally substituted with 1-2 substituents selected from —NH₂, —OH, —SH, —SMe, —NH(C=NH)NH₂, CO₂H, and CO₂NH₂;
($C_1$-$C_6$ alkylene)-phenyl, optionally substituted with 1-2-OH;
($C_1$-$C_6$ alkylene)-indolyl; and
($C_1$-$C_6$ alkylene)-imidazolyl; or
R² and R^{d1}, in the —CH(R²)N(R^{d1})— group, combine to form a pyrrolidine ring.

4. The compound according to claim 1, wherein each of B¹ and B² is independently selected from CH₃.

5. The compound according to claim 1, wherein each occurrence of R^{d1} is H.

6. The compound according to claim 1, wherein the compound is a compound of formula (II-a), Formula (II-c1), Formula (II-c2), Formula (II-d), or Formula (II-e):

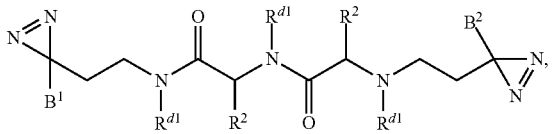
(II-a)

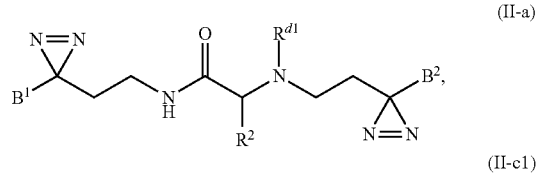
(II-c1)

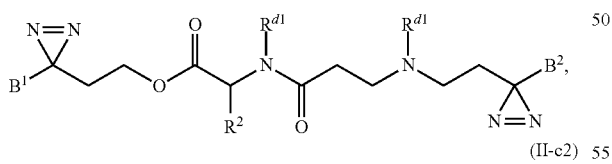
(II-c2)

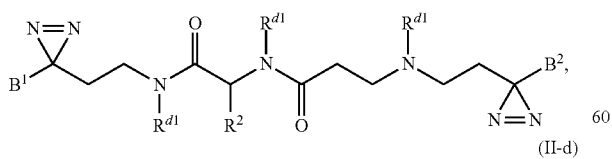
(II-d)

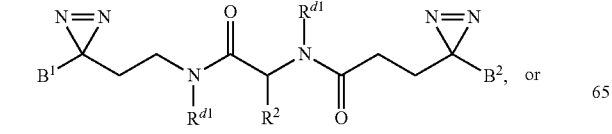
, or (II-e)

[structure]

or a pharmaceutically acceptable salt thereof.

7. The compound according to claim 1, wherein each occurrence of R² is independently selected from:
H;

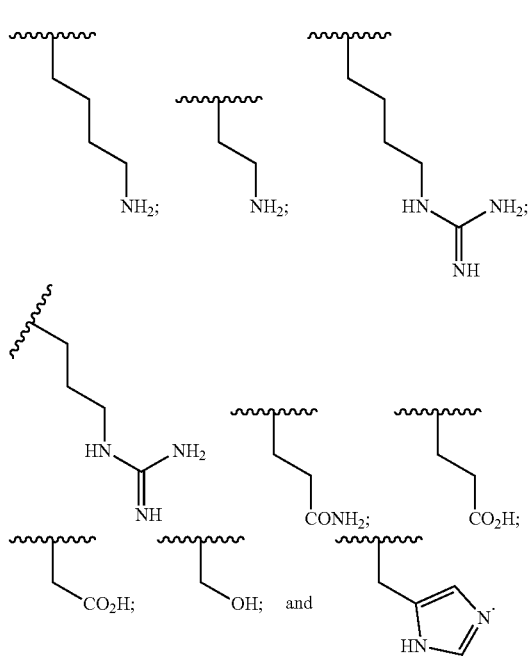

8. The compound according to claim 1, wherein:
each of E¹ and Q¹ is independently $C_1$-$C_6$ alkylene;
R² is independently selected from the group consisting of:
(i) $C_1$-$C_6$ alkyl, which is substituted with 1 R^a; and
(ii) H;
R^a is independently selected from the group consisting of:
—C(=O)OH and —NR'C(=NR')NR'R";
each occurrence of R' and R" is H;
each occurrence of R^{d1} is H; and
each of H¹, G¹, L¹, and M¹ is independently selected from:
a bond;
—C(=O)CH(R²)N(R^{d1})—; and
—C(=O)CH(R²)CH₂N(R^{d1})—.

9. A pharmaceutical composition comprising a compound of claim 1, or a pharmaceutically acceptable salt thereof, and a pharmaceutically acceptable excipient.

10. A method for applying treatment to a cornea of an eye, comprising:
administering a compound of claim 1, or a pharmaceutically acceptable salt thereof, to the cornea of a subject in need thereof; and
applying an electromagnetic radiation to the cornea, thereby generating cross-linking in the cornea.

11. A compound of Formula (III):

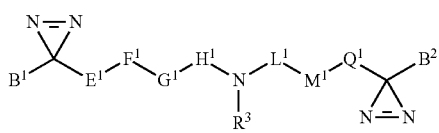

or a pharmaceutically acceptable salt thereof,
wherein:
each of $B^1$ and $B^2$ is independently —$Z^1$—$Z^2$—$Z^3$, wherein:
$Z^1$ is $C_{1-3}$ alkylene;
$Z^2$ is a bond; and
$Z^3$ is H;
each of $E^1$, $F^1$, $H^1$, $L^1$, $M^1$, and $Q^1$ is independently selected from:
a bond; and
$C_1$-$C_6$ alkylene;
provided that at least one of $E^1$ and $F^1$ is $C_1$-$C_6$ alkylene;
$G^1$ is a bond or C(=O);

$R^3$ is selected from the group consisting of:
(i) $C_1$-$C_6$ alkyl, which is substituted with 1 $R^a$; and
(ii) $L^3$-heterocyclyl, wherein the heterocyclyl includes from 5-6 ring atoms, wherein from 1-3 ring atoms are selected from the group consisting of $N(R^d)$ and O;
each occurrence of $R^a$ is —C(=O)OH;
each occurrence of $R^d$ is H; and
each $L^3$ is a bond.

12. The compound according to claim 11, wherein $F^1$, $G^1$, $H^1$, $L^1$, and $M^1$ is a bond.

13. The compound according to claim 11, wherein is $C_1$-$C_6$ alkyl, is substituted with $CO_2H$.

14. The compound according to claim 11, wherein $R^3$ is $L^3$-heterocyclyl, wherein the heterocyclyl is selected from the group consisting of pyrrolidinyl, piperidinyl and morpholinyl.

15. The compound according to claim 11, wherein each of $B^1$ and $B^2$ is independently selected from $CH_3$.

16. The compound according to claim 11, wherein $F^1$, $H^1$, $L^1$, and $M^1$ is a bond; and $G^1$ is C(=O).

17. A compound selected from the following:

| Example # | Compound | Name/ID # |
|---|---|---|
| 1 | | Compound 2 |
| 2 | | Compound 6 |
| 3 | | Compound 10 |
| 4 | | Compound 14 |
| 5 | | Compound 18 |

-continued
| Example # | Compound | Name/ID # |
|---|---|---|
| 6 | 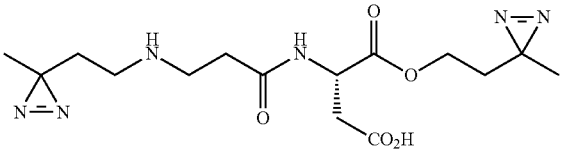 | Compound 25 |
| 7 | 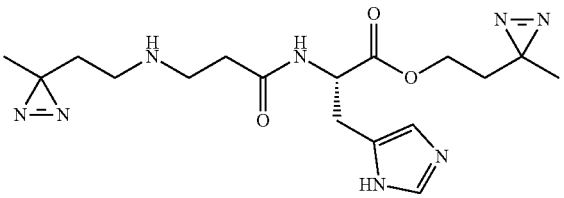 | Compound 29 |
| 8 | 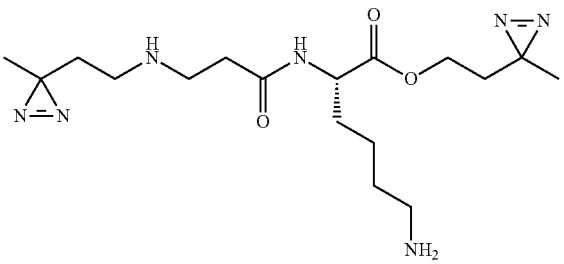 | Compound 33 |
| 9 | 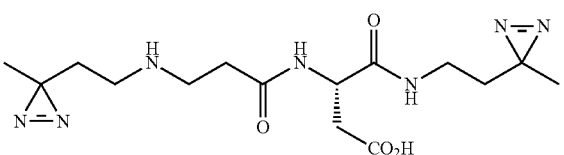 | Compound 37 |
| 10 | 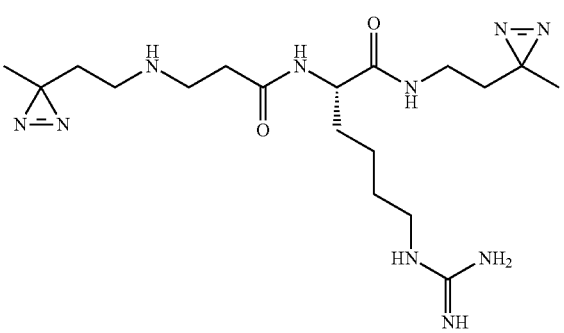 | Compound 43 |
| 11 | 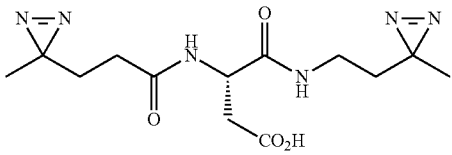 | Compound 45 |
| 12 | 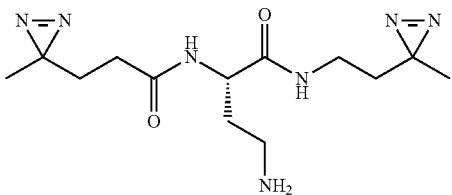 | Compound 49 |

| Example # | Compound | Name/ID # |
|---|---|---|
| 13 | 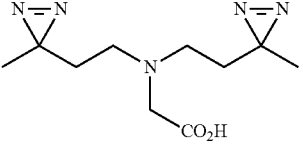 | Compound 52 |
| 14 | 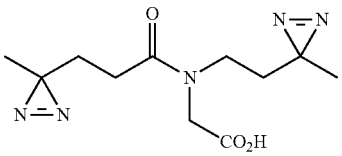 | Compound 54 |
| 15 | 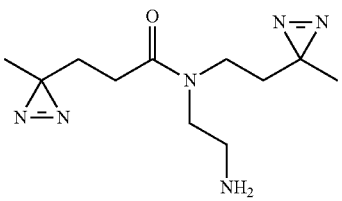 | Compound 57 |
| 16 | 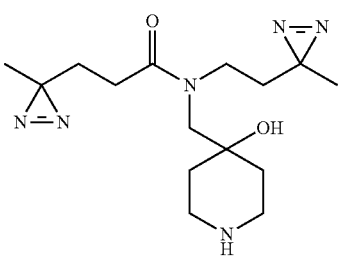 | Compound 60 |
| 17 | 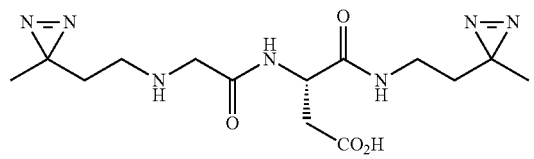 | Compound 64 |
| 18 | 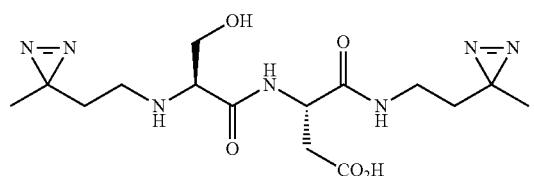 | Compound 68 |
| 19 | 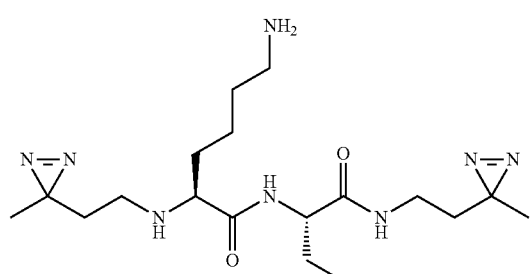 | Compound 73 |

-continued

| Example # | Compound | Name/ID # |
|---|---|---|
| 20 | | Compound 75 |
| 21 | | Compound 78 |
| 22 | | Compound 81 |
| 23 | | Compound 84 | or a pharmaceutically acceptable salt thereof.

\* \* \* \* \*